(12) United States Patent
Greenway et al.

(10) Patent No.: US 11,767,497 B2
(45) Date of Patent: Sep. 26, 2023

(54) SYSTEM AND METHOD FOR GENERATING AND TESTING TISSUE

(71) Applicant: Propria LLC, Branford, CT (US)

(72) Inventors: Warren Greenway, Cedar Creek, TX (US); Darren Harris, La Vernia, TX (US); Aydin Akyol, Hawthorne, CA (US)

(73) Assignee: Propria LLC

(*) Notice: Subject to any disclaimer, the term of this patent is extended or adjusted under 35 U.S.C. 154(b) by 311 days.

(21) Appl. No.: 16/941,255

(22) Filed: Jul. 28, 2020

(65) Prior Publication Data

US 2021/0024862 A1  Jan. 28, 2021

Related U.S. Application Data

(60) Provisional application No. 62/879,525, filed on Jul. 28, 2019.

(51) Int. Cl.
| | |
|---|---|
| *C12M 3/00* | (2006.01) |
| *C12M 1/00* | (2006.01) |
| *C12N 5/00* | (2006.01) |
| *C12M 1/26* | (2006.01) |
| *C12M 1/12* | (2006.01) |

(52) U.S. Cl.
CPC ............ *C12M 21/08* (2013.01); *C12M 23/38* (2013.01); *C12M 25/02* (2013.01); *C12M 25/14* (2013.01); *C12M 33/04* (2013.01); *C12N 5/0068* (2013.01)

(58) Field of Classification Search
CPC .............................. C12M 25/14; C12M 21/08
See application file for complete search history.

(56) References Cited

U.S. PATENT DOCUMENTS

| | | | |
|---|---|---|---|
| 4,201,845 A | * | 5/1980 | Feder .................... C12M 29/04 |
| | | | 435/297.2 |
| 5,139,951 A | | 8/1992 | Butz et al. |
| 5,501,971 A | | 3/1996 | Freedman et al. |
| (Continued) | | | |

OTHER PUBLICATIONS

International Search Report and Written Opinion issued in International Application No. PCT/US20/43904 dated Dec. 18, 2020.

*Primary Examiner* — Nathan A Bowers
(74) *Attorney, Agent, or Firm* — The Belles Group, P.C.

(57) ABSTRACT

Systems, devices, and methods for producing a tissue specimen and performing subsequent biomechanical testing thereof to quantify various biological/physiological properties and characteristics. The system may include a bioreactor device for producing the tissue specimen which includes a packaged/sealed seeding cup containing a scaffold in a sterile environment amenable to seeding with cells. After seeding, the cup may be stored in a standard laboratory culture tray for incubation. The produced tissue specimen may next be transferred to a testing instrument under control of a microcontroller which automatically performs a series of tests on the tissue and generates testing data communicated to an external electronic device which can operably interact with and control operation in part of the testing instrument via software. Tissue integrity in the instrument may be maintained by sterile fluid circulation and heating systems. The system advantageously provides efficient and reproducible tissue growth and analysis.

15 Claims, 43 Drawing Sheets

(56) References Cited

U.S. PATENT DOCUMENTS

| | | | |
|---|---|---|---|
| 5,843,766 A * | 12/1998 | Applegate | C12M 25/02 |
| | | | 435/297.5 |
| 6,040,153 A * | 3/2000 | Lemonnier | C12M 41/36 |
| | | | 435/305.4 |
| 7,186,548 B2 | 3/2007 | Li | |
| 9,751,084 B2 * | 9/2017 | Greenizen | B01L 3/5085 |
| 2007/0166817 A1 | 7/2007 | Wilkes et al. | |
| 2011/0212500 A1 | 9/2011 | Boronyak et al. | |
| 2015/0064780 A1 | 3/2015 | Hopkins et al. | |
| 2018/0073964 A1 | 3/2018 | McCormick | |
| 2018/0216057 A1 | 8/2018 | Campbell et al. | |
| 2018/0313811 A1 | 11/2018 | Ali | |
| 2019/0105021 A1 | 4/2019 | Von Bueren et al. | |
| 2019/0218501 A1 | 7/2019 | Kamen et al. | |
| 2020/0166439 A1 | 5/2020 | Marsch | |
| 2022/0143602 A1 * | 5/2022 | Sims | B01L 3/50855 |

* cited by examiner

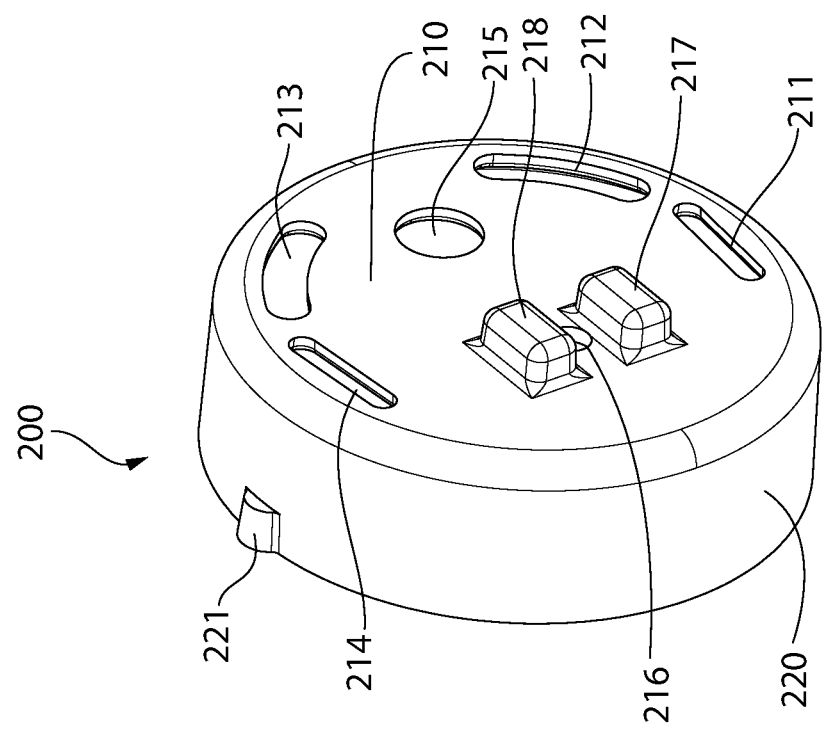
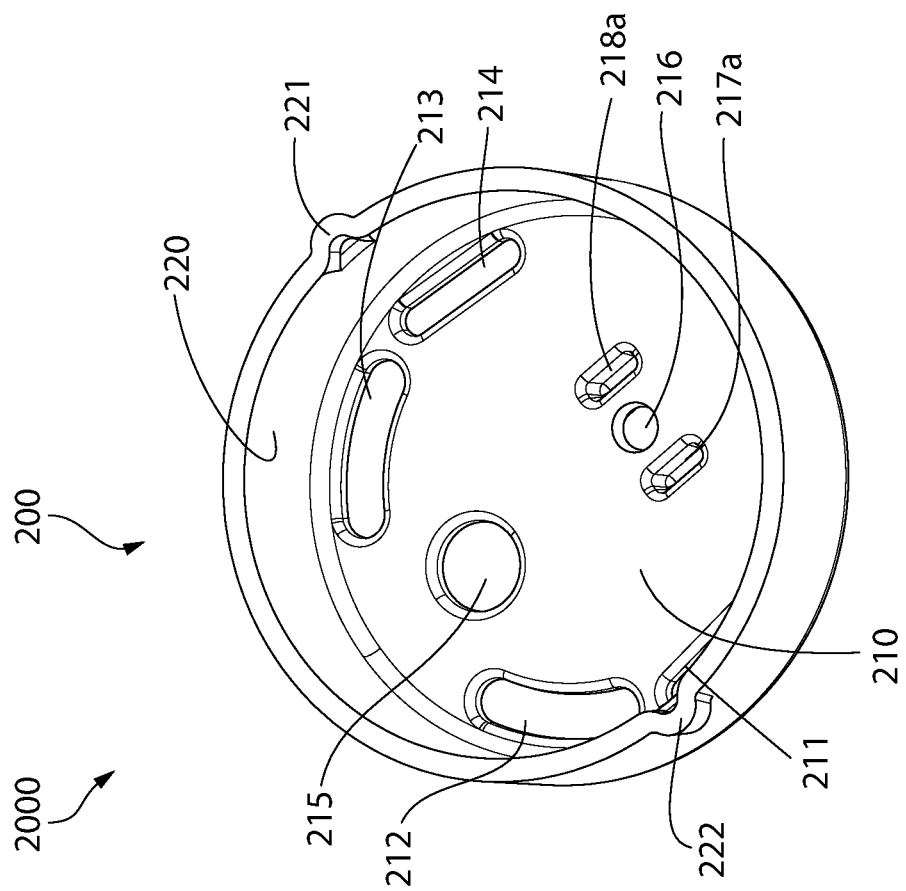
FIG. 2B
FIG. 2A

Cassete resting in pod bath

Clip "grabbed" by the cantilever

Clip "grabbed" but arms still engaged

Clip "grabbed" and arms disengaged
Clip now rests fully on the cantilever

SYSTEM AND METHOD FOR GENERATING AND TESTING TISSUE

CROSS-REFERENCE TO RELATED APPLICATIONS

The present application claims the benefit of U.S. Provisional Patent Application Ser. No. 62/879,525, filed Jul. 28, 2019, the disclosure of which is incorporated herein by reference.

BACKGROUND

Tissue engineering is an important technology and tool used in medical diagnostics and treatment. However, regenerated tissue and other engineering principles have a limited use in diagnostic and clinical applications. Due to the specialized techniques, high costs, and delicacy of generated tissue, it remains challenging to scale up engineered tissue applications for wide-spread practical use in basic science and clinical uses.

Biomechanical tissue generation and testing systems also typically require mounting of a tissue specimen by direct manual handling and manipulation of the tissue in order to hook, tie, or otherwise fasten the specimen to a force transducing system. To perform this successfully, this process requires a higher level of training, practice, and skill than typical lab technicians possess. A tissue can be damaged during manual mounting, leading to experimental artifacts and contributing to experimental error. Tissue damage during manual mounting can also completely destroy a tissue specimen or damage the testing instrument, leading to lost productivity and added expense. Additionally, it is also time consuming and error prone.

Thus, there is a need to provide a cost-effective, user-friendly, reliable and standardized system for carrying out tissue production and analysis.

BRIEF SUMMARY

The present invention relates in part to a bioreactor device and related systems and methods to generate a biologically viable tissue specimen or construct. The present invention additionally relates in part to a biomechanical testing system and related methods to characterize the produced tissue construct and to study basic biological/physiological characteristics thereof, characterize biologically active compound affects on the tissue construct, and detect, assess, and treat organ pathologies.

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

It should be understood that the detailed description and specific examples, while indicating the typical embodiments of the invention, are intended for purposes of illustration only and are not intended to limit the scope of the invention.

BRIEF DESCRIPTION OF THE DRAWINGS

The detailed description of the invention will be better understood when read in conjunction with the appended drawings. It should be understood, however, that the invention is not limited to the precise arrangements and instrumentalities of the embodiments shown in the drawings. Many embodiments of the present invention include a liquid. The liquid has been omitted from most of the figures to depict the structure of the present invention with greater clarity.

FIG. 1A depicts a bottom perspective view of a consumable bioreactor device and respective components according to one embodiment. FIG. 1B is a top perspective view thereof. FIG. 1C is a top exploded perspective view thereof. FIG. 1D is a bottom exploded perspective view.

FIGS. 2A-2B depict a mask structure according to one embodiment. FIG. 2A depicts a top perspective view of a mask structure according to one embodiment. FIG. 2B is a bottom perspective view thereof.

FIG. 3A depicts a top perspective view of a cassette according to one embodiment. FIG. 3B is a bottom perspective view. FIG. 3C is a cross section top perspective view.

FIG. 4A depicts a cross section side perspective view of a support apparatus according to one embodiment. FIG. 4B is a top perspective view and includes a cassette.

FIG. 6A depicts a top perspective view of a biomedical instrument, or biomechanical testing system, according to one embodiment. FIG. 6B is a bottom perspective view.

FIGS. 11-16 depict an example of how to seed the tissue scaffold within a bioreactor device.

FIG. 11 depicts a top perspective view of the bioreactor device according to one embodiment with the lid being taken off.

FIG. 13A depicts a side exploded view of the bioreactor device according to one embodiment having a pipette tip inserted through the media hole penetrating the media exchange region, and aspirating or dispensing sterile liquid. FIG. 13B is a side exploded view of the bioreactor device according to one embodiment having a pipette tip inserted through the media hole penetrating the media exchange region, and where the sterile liquid has been aspirated and the only remaining sterile liquid which remains is below the scaffold.

FIG. 15 depicts a top perspective view of a consumable bioreactor device and respective components according to one embodiment where forceps are used to lift the mask out from the seeding cup.

FIG. 16 depicts a top perspective view of a consumable bioreactor device and respective components according to one embodiment where forceps are used to lift the cassette out from the seeding cup.

FIG. 19A depicts a side perspective view of assembly process for insertion of hydrogel peg into the cassette frame and floating clip. FIG. 19B is an exploded side view perspective of insertion of hydrogel peg into the cassette frame where the hydrogel is entering into the slot. FIG. 19C is an exploded side view perspective of insertion of hydrogel peg into the cassette frame where the hydrogel has entered into the slot.

FIG. 28A depicts an exploded side view perspective of the interface between the cassette, detachable clip and cantilever. FIG. 28B is an exploded side view perspective of the interface between the cassette, detachable clip and cantilever where the cantilever traverses towards the detachable clip. FIG. 28C is an exploded side view perspective of the interface between the cassette, detachable clip and cantilever where the cantilever has reached the detachable clip.

In FIG. 33A, the force transducer is shown with lateral movement. In FIG. 33B, the force transducer is shown without lateral movement.

All figures are schematic and not necessarily to scale. Any reference to a figure by a whole number which contains multiple figures sharing the same number but with different alphabetical suffixes (e.g. FIGS. 1A, 1B, etc.) shall be construed as a reference to all those figures unless explicitly described otherwise. In addition, a reference herein indicating that a particular component or feature is shown in a specific figure does not necessarily mean that the same component or feature does not appear in additional figures not referenced.

DETAILED DESCRIPTION

Figure 1B:
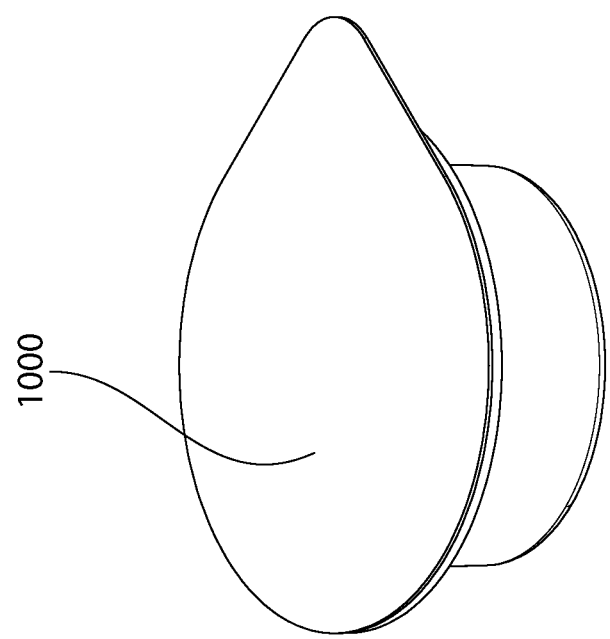
FIGS. 1A-1D depict a consumable bioreactor device and respective components according to one embodiment.
Figure 1A:
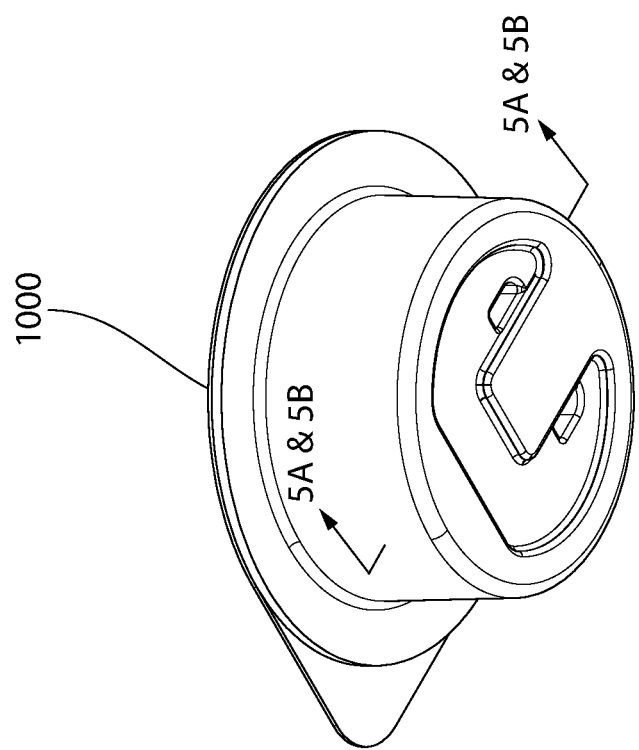
Figure 1C:
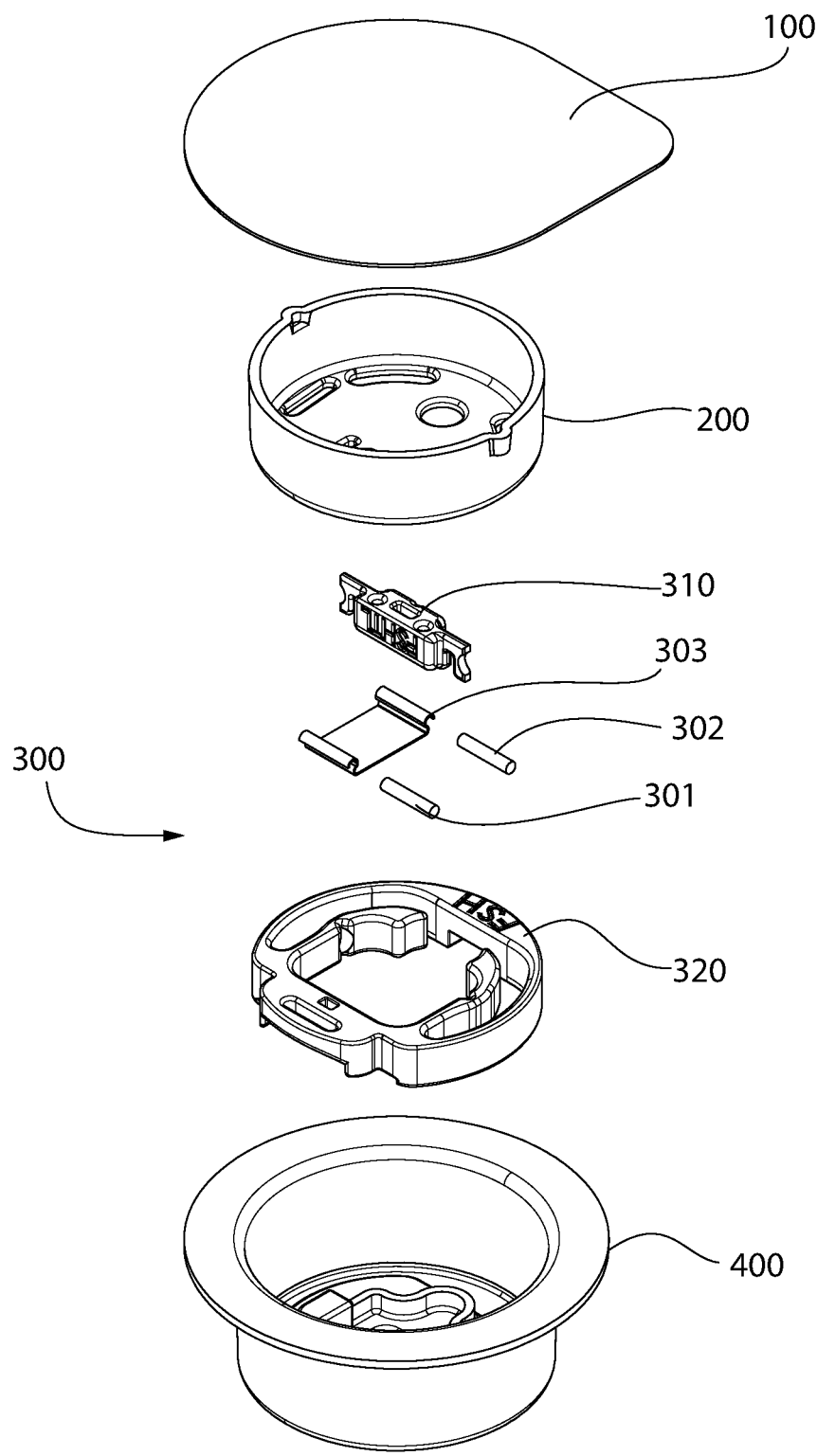

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other applications and methods. It is to be understood that the invention is not limited in its application to the details of any particular embodiment shown. The terminology used herein is for the purpose of description and not to limit the invention, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", "containing", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight of the total composition. Reference to a molecule, or to molecules, being present at a "wt. %" refers to the amount of that molecule, or molecules, present in the composition based on the total weight of the composition.

According to the present application, use of the term "about" in conjunction with a numeral value refers to a value that may be +/−5% of that numeral. As used herein, the term "substantially free" is intended to mean an amount less than about 5.0 weight %, less than 3.0 weight %, 1.0 wt. %; preferably less than about 0.5 wt. %, and more preferably less than about 0.25 wt. % of the composition.

Unless defined otherwise, all technical and scientific terms used herein have the same meanings as commonly understood by one of ordinary skill in the art to which this invention belongs. All patents, patent applications, publications, and other references cited or referred to herein are incorporated by reference in their entireties for all purposes. In the event of a conflict in a definition in the present disclosure and that of a cited reference, the present disclosure controls.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such. Terms such as "attached," "affixed," "connected," "coupled," "interconnected," "secured" and other similar terms refer to a relationship wherein structures are secured or attached to one another either directly or indirectly through intervening structures, as well as both movable or rigid attachments or relationships, unless expressly described otherwise.

The discussion herein describes and illustrates some possible non-limiting combinations of features that may exist alone or in other combinations of features. Furthermore, as used herein, the term "or" is to be interpreted as a logical operator that results in true whenever one or more of its operands are true.

The disclosure set forth in U.S. Patent Pub. No. 2018/0216057 is hereby incorporated by reference in its entirety.

The present invention relates in part to a packaged bioreactor device and subsequent systems and methods to generate a biologically viable tissue construct. The present invention additionally relates in part to a cooperatively configured biomedical/physiological tissue testing instrument and subsequent systems and methods to characterize the produced tissue construct and methods to study basic biological phenomena, characterize biologically active compounds, and detect, assess, and treat organ pathologies. The systems and methods described herein advantageously allow analysis of tissue in a reproducible manner such that the level of training required to successfully prepare, process, and analyze the tissue sample is significantly diminished. As further described herein, this in part is achieved by a pre-packaged hermetically sealed tissue preparation device containing sterile tissue scaffold and an automatically operated testing instrument under the control of a programmable microcontroller. Furthermore, the systems and methods allows for retainment of the tested tissue sample for additional testing at a later time. These aspects and features of the present disclosure are further described below.

Packaged Bioreactor Device

General reference is made below to FIGS. 1-5B and 11-18, with emphasis on specific figures as indicated for portions of the description.

Figure 20A:
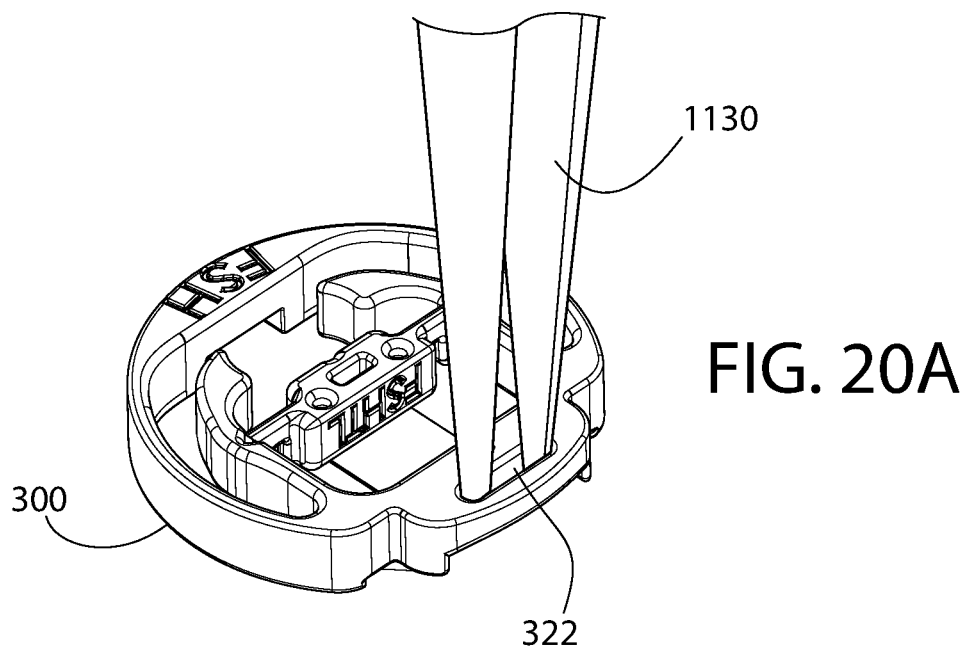
FIG. 20A depicts forceps grasping the cassette through the grasping slot.
Figure 20B:
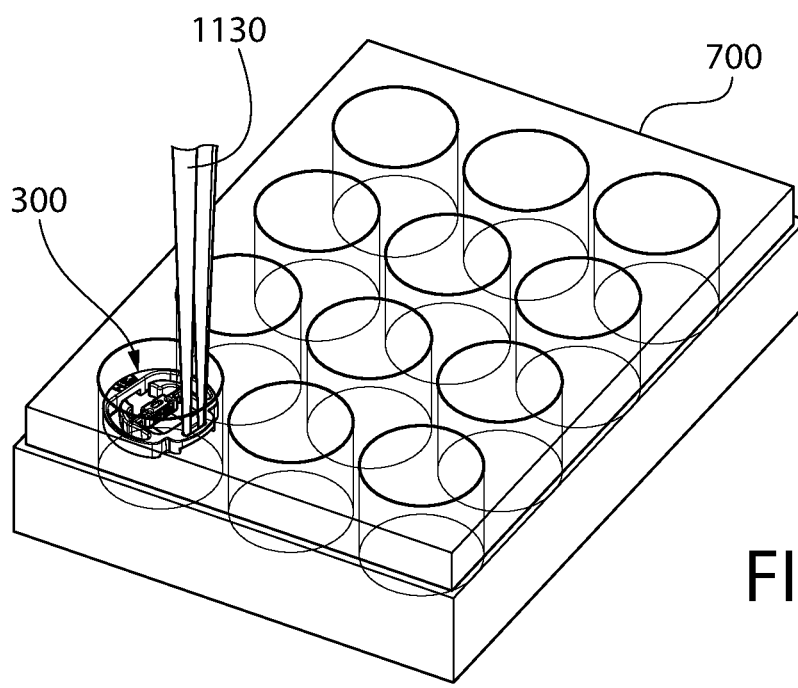
FIG. 20B depicts placement of the cassette within a 12 well plate with use of forceps.

In certain embodiments, the bioreactor device 1000 may include a hermetically sealed, sterile, and pre-packaged tissue scaffold for implantation with living cells and growing a tissue specimen amenable to analysis and testing as further described herein. The device packaging may be opened so that the tissue scaffold may be accessed and seeded with eukaryotic cells, allowed to incubate for tissue formation, and the grown tissue specimen then analyzed Referring specifically to FIGS. 1A-5B, the bioreactor device 1000 is sized to be compatible with standard tissue culture well-plates and in a non-limiting preferred embodiment, the device is sized to be compatible with a standard 12-well tissue plate. In one embodiment, as shown in FIG. 20B, placement of the cassette 300 into a 12 well or cell culture dish 700 may be utilized. The cassette may then be incubated under intended conditions, such as testing conditions. Transfer of the cassette 300 from the bioreactor device 1000 to the testing instrument 2000 may be made by use of forceps 1130 being placed into and engaging the grasping slot 322 of the cassette 300. Other modes of handling and transferring the cassette 300 may be used.

As exemplified in FIGS. 1C-1D and 4A-5B, the bioreactor device 1000 can comprise a cup lid 100, a mask 200, a cassette 300 with a sterile and decellularized tissue scaffold 303 and detachable 310, and a support apparatus having a cup-shaped body defining a structure such as a seeding cup 400. The cup 400 includes a bottom, a top, and an internal cavity 450 extending between the bottom and top in which the removable mask and cassette reside. Cup 400 may have a generally cylindrical body and includes bottom wall 451 defining a closed bottom, annular top edge 452 which defines an open top and may include an outwardly flared lip 402, and a cylindrical side wall 401 extending upwards from the bottom wall to the top edge. An interior fluid retention wall 421 extending upwards from the bottom wall. Retention wall 421 may completely surround the tissue scaffold 303 and may have a continuous structure for retaining sterile fluid such a buffered saline to at least partially immerse the tissue scaffold and specimen therein to preserve their viability. The fluid retention wall is spaced radially inwards from the sidewall and defines an annular mounting recess 430 formed between the side wall of the cup and retention wall which receives a peripheral portion of cassette frame 320 of the cassette 300 at least partially therein to detachably mount the cassette to the cup.

The bottom wall 451 further defines a centrally located seeding trough 410 positioned below tissue scaffold 303 and media exchange region 420 between the fluid retention wall 421 and seeding trough. Region 420 may completely surround or surround the seeding trough for a majority of the perimeter of the trough. The bottom of seeding trough 410 defines a first floor (e.g. surface) 454 which is deeper and located at a lower elevation than a second floor (e.g. surface) defined by media exchange region 453. Advantageously, this elevation differential allows the sterile fluid to be extracted from the media exchange region 420 during the process of seeding the tissue scaffold 303 down to the fluid level within the seeding trough 410 which retains the fluid to keep the tissue scaffold and specimen in a wetted condition by the sterile buffered saline solution/fluid (see, e.g. FIGS. 13A-B. This ensures that the user-introduced tissue seeds (i.e. cells) remain concentrated on the tissue scaffold during the desired incubation period rather than floating away from towards portions beyond the seeding trough.

With continuing general reference to FIGS. 1-5B and 11-18, the scaffold 303 may be fastened to the cassette frame 320 and clip 310 through positive-locking interaction with the hydrogel locking pegs (or hydrogel inserts) 301, 302. The hydrogel may be made of any expandable hydrogel. In certain embodiments, the hydrogel is made of glycol. In further embodiments, the hydrogel is made of polyethylene glycol (PEG). The positive lock may be made by having rounded enlarged recesses formed by locking slots incorporated into the cassette frame 320 which are dimensioned to allow the hydrogel locking pegs 301, 302 to expand after insertion to positively lock the tissue scaffold into place on clips 310, 315 as further described herein.

Figure 19A:
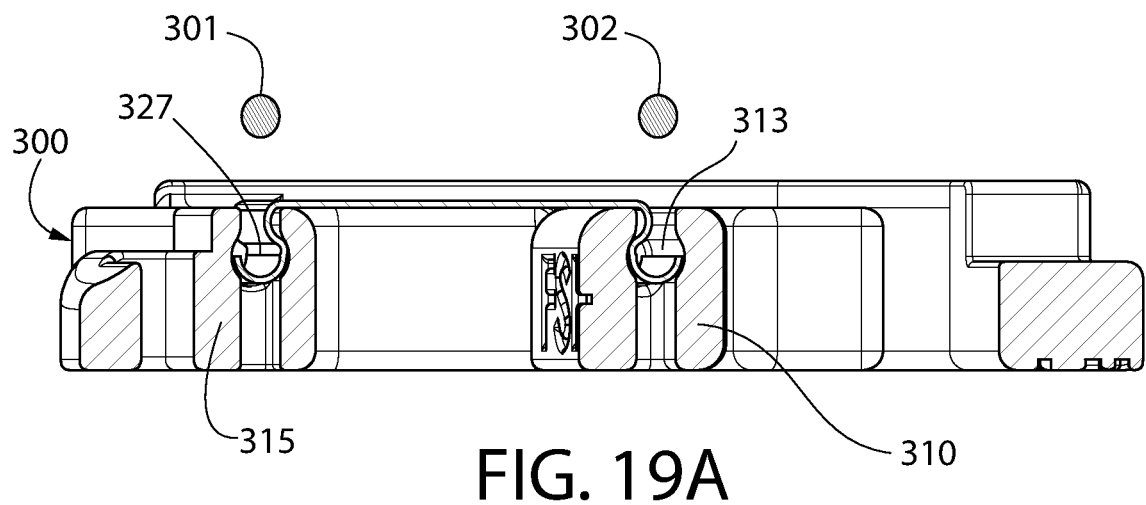
FIGS. 19A-19C depict the assembly process for insertion of hydrogel peg into the cassette frame and floating clip.
Figure 19B:
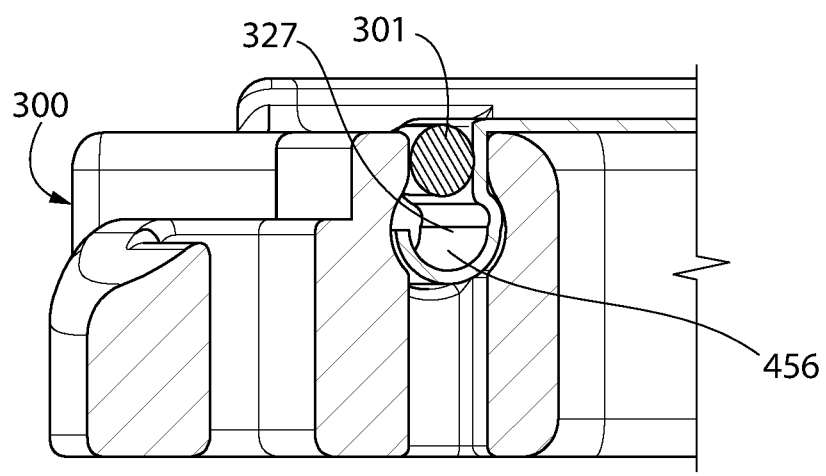
Figure 19C:
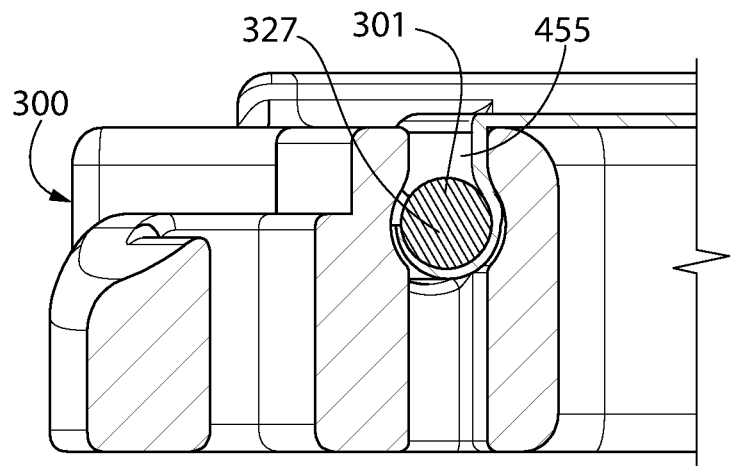

In non-limiting preferred embodiments, the hydrogel locking pegs 301 and 302 are changeable from a shrunken diameter when the pegs are in a dehydrated condition to a larger enlarged diameter when the pegs are hydrated. The locking slots 327 are formed in and defined by floating clip 310 and detachable fixed clip 315 disposed on the cassette frame 320. The first and second ends of the tissue scaffold 303 are each fixedly coupled to the fixed and floating clips 315, 310 by a hydrogel locking peg arranged in locking slots 327 which may be considered light-bulb shaped in some non-limiting embodiments shown in FIGS. 19A-C. Such locking slots may include an upper narrow throat portion 455 which opens into a lower diametrically enlarged circular seating portion 456 in which the locking pegs are positioned when the tissue scaffold is locked to the clips.

The device according to claim 17 or 18, wherein the locking pegs are in the hydrated condition when positioned in the circular seating portion of the locking slots. In certain embodiments, the locking pegs 301 and 302 can pass through the narrow throat portion 455 in locking slots 327 of the cassette frame 320 (i.e. clips 310, 315) into seating portion 456 when in the dehydrated condition with the shrunken diameter, but cannot pass back out through the throat portion when in the hydrated condition with the enlarged diameter. The swollen hydrogel pegs engage the walls of the clips 310, 315 to positively and rigidly lock the ends of the tissue scaffold to the clips and cassette 300. In certain embodiments, the cassette 300 is configured to hold the tissue scaffold 303 in an inverted suspended manner stretched between each clip (for example, the floating clip 310 and the fixed clip 315 on the cassette frame (see, e.g. FIGS. 13A-B) in which the tissue scaffold 303 is located below the clips proximate to and at least partially immersed in the sterile buffered saline fluid or solution within the seeding trough 410.

The lid 100 may be hermetically sealed the top of the cup 400 and be removable by the user in order to provide access to the cup cavity and tissue scaffold. Any suitable type of sealed lid may be used. In one non-limiting construction, the lid 100 may comprise a peel-able foil film adhesively adhered to the top of the cup 400 to hermetically seal and enclose the cup cavity 450 (see, e.g. FIGS. 4A and 11). For example, the foil lid od may be adhered to the outwardly turned/flared lip 402 at the top of the seeding cup 400 which forms a circumferentially-extending and laterally broadened sealing surface for improved adhesive engagement. The cup lid 100 creates a hermetic seal to ensure sterility of the internal components within the bioreactor cup cavity 450 (e.g. tissue scaffold, etc.). In certain embodiments, the cup lid 100 is made of foil or a plastic-lined foil. In other embodiments, the cup lid 100 could be made of a plastic, plastic derivative, a polymer film, or a thin sheet of at least partially flexible metal.

The bioreactor device 1000 preferably is configured to contain a sterile liquid or fluid 1120, such as a buffered saline solution, to preserve the tissue scaffold until seeding as described herein.

In some embodiments, the bioreactor device 1000 contains a barcode or other indicia for easy electronic identification and tracking of a particular tissue specimen. The bioreactor device 1000 including seeding cup 400, tissue scaffold 303, cassette 300, locking clips 310, 315, and mask 200 could be made of any suitable non-metallic and/or metallic material capable of maintaining a sterile environment within the cup and which is biomedically compatible/inert with respect to the tissue scaffold material. In one non-limiting example, the foregoing components may be formed of a suitable plastic material. The foregoing components can be produced through any suitable standard methods, such as without limitation injection molding, casting, extrusion, etc.

Figure 5A:
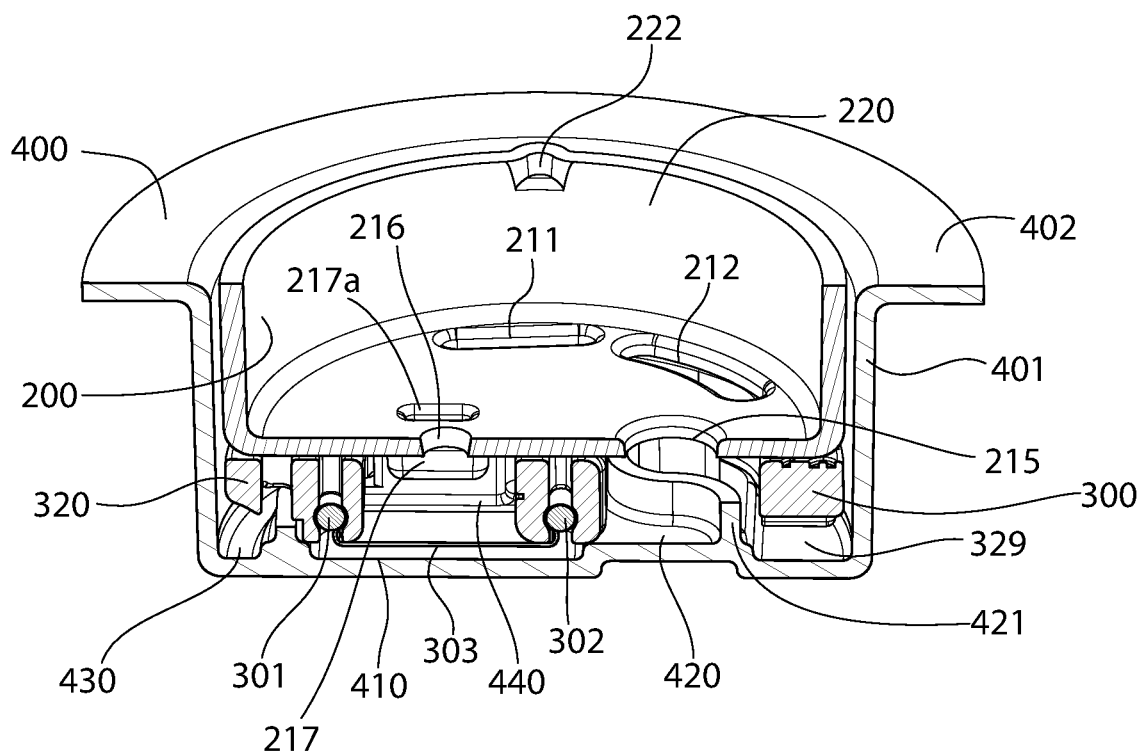
FIG. 5A depicts a cross section of a consumable bioreactor cup with a mask, cassette, and support apparatus according to one embodiment. A lid has been omitted.
Figure 12A:
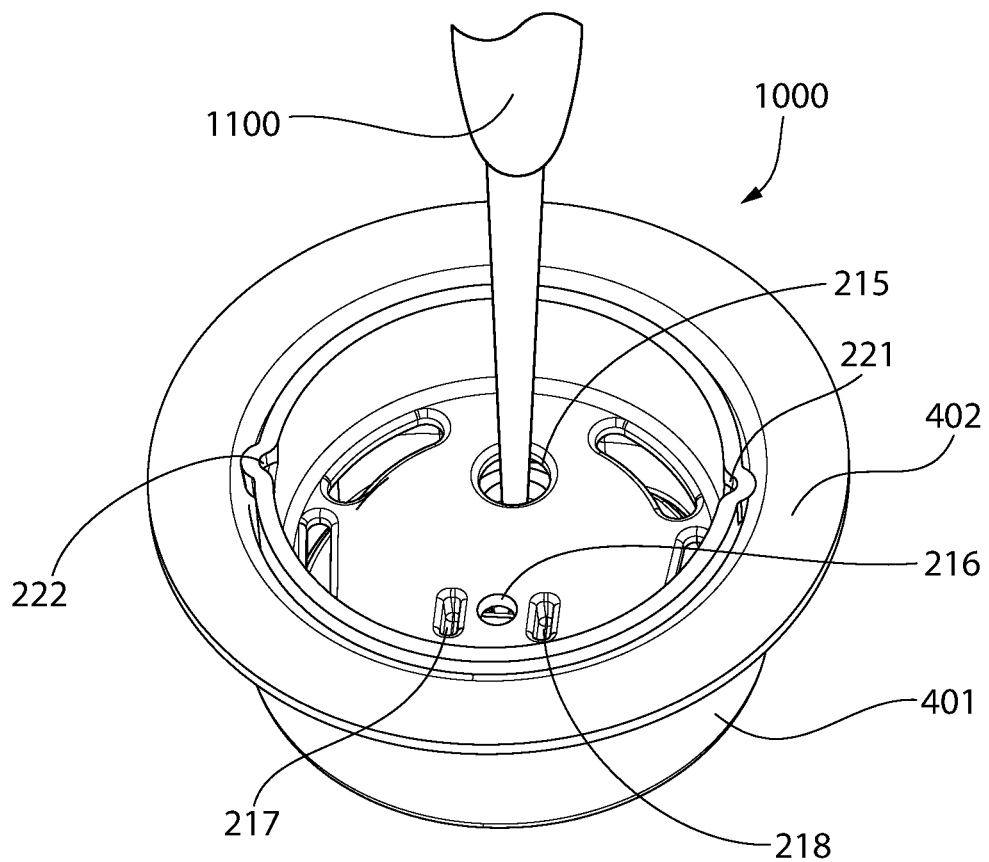
FIG. 12A depicts top perspective view of the bioreactor device according to one embodiment having a pipette tip inserted into the media hole.
Figure 12B:
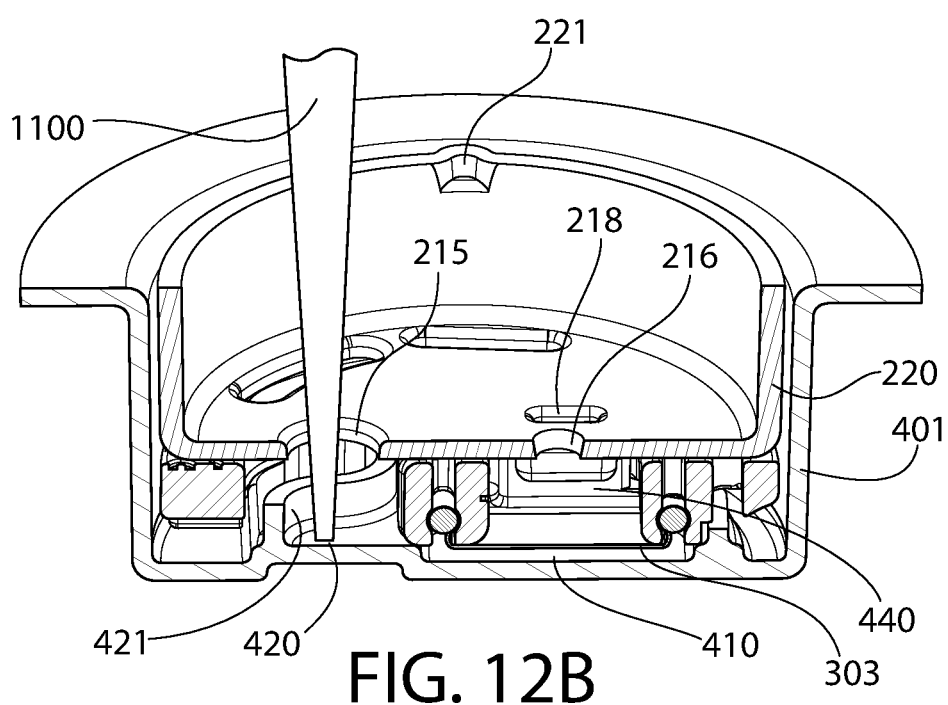
FIG. 12B is a cross sectioned side view perspective.
Figure 13A:
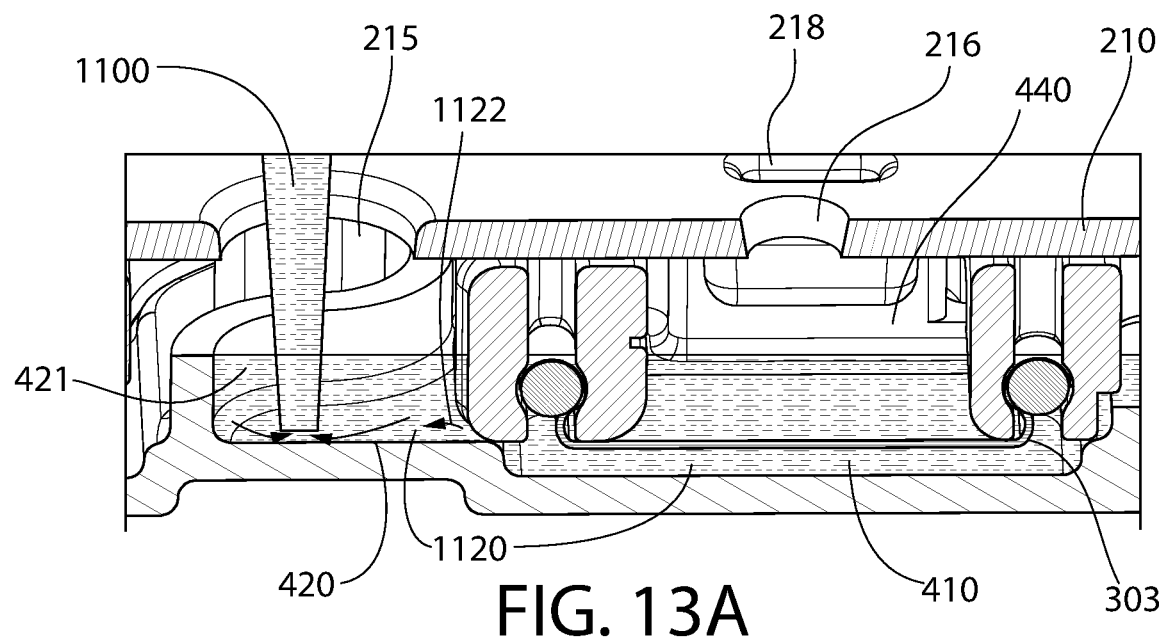
FIGS. 13A-B depict a side exploded view of the bioreactor device according to one embodiment having a pipette tip inserted through the media hole and penetrating the media exchange region.
Figure 13B:
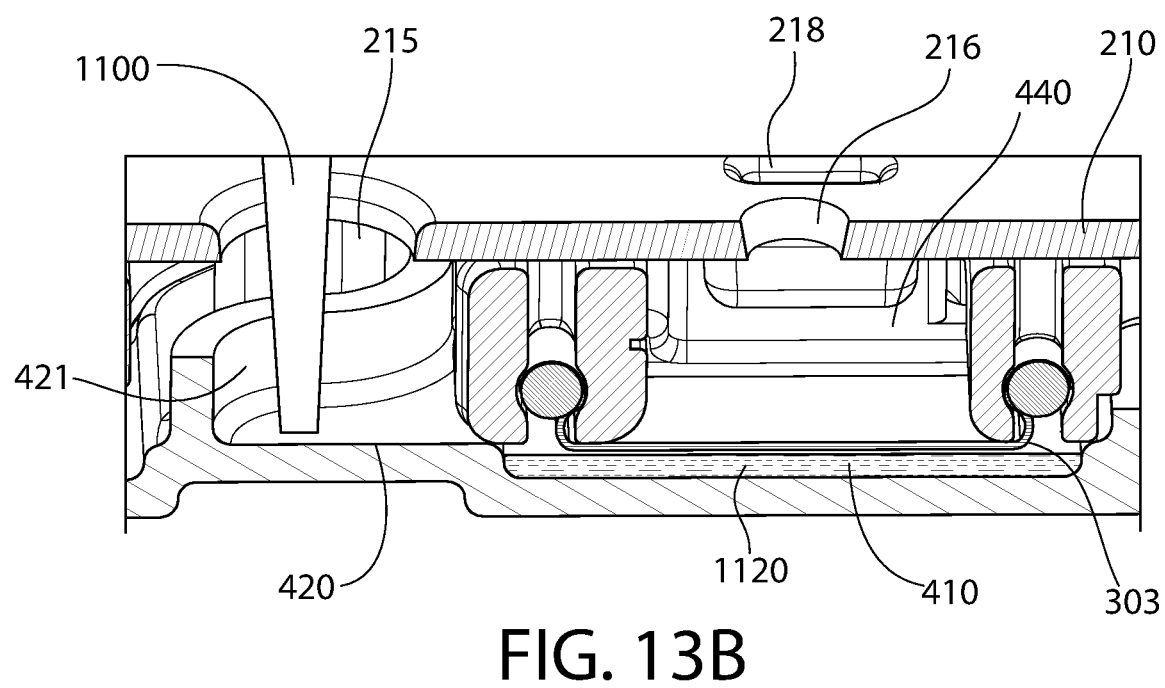

When all the bioreactor components are combined, the scaffold sits within the cup cavity 450 (For example, as shown in FIG. 5A). The mask 200 may be removably disposed in the cup cavity above the scaffold 303 (For example, as shown in FIG. 5A). The mask may include a plurality of through holes to access the tissue scaffold and portion of the cavity below the mask (For example, as shown in FIGS. 2A-2B and 5A). The sterile fluid 1120 may be disposed in the cavity of cup 400 at least below the mask 200, the tissue scaffold 303 at least partially immersed in the fluid (For example, as shown in FIGS. 13A-13B). In certain embodiments, the fluid 1120 below the mask 200 is accessible for aspiration through a media or aspiration hole 215, of the mask through holes which is laterally offset in position on the mask 200 from the tissue scaffold 303. The through holes may include a seeding hole 216 in the mask 200 which is positioned directly above the tissue scaffold 303 for introducing cells directly onto the scaffold through the seeding hole 216 (For example, as shown in FIGS. 12A-12B).

Mask

The structure of the mask 200 illustrated in FIGS. 2A and 2B depict a bottom wall 210 with the foregoing variety of through openings (first straight slot 211 for air exchange with portions of cup cavity 450 beneath the mask, first curved slot 212 for air exchange, second curved slot 213 for enabling mask removal, second straight slot 214 for air exchange, round media or aspiration hole 215 for sterile fluid media exchange, and round seeding hole 216), a pair of downwardly extending external anti-rotation protrusions 217, 218, and a cylindrical side wall 220 with a laterally extending first external retention protrusion 221 and a second external retention protrusion 222. As described elsewhere herein, the first protrusion 217 and second protrusion 218 each define an associated upwardly open removal recess 217*a*, 218*b* (FIG. 17) which are spaced to allow squeezed-together forceps to be inserted and then released thereby exerting an outward pressure within the recesses/protrusions 217, 218 which allow the mask 200 to be removed from the cup 400 (see, e.g. FIG. 15). The larger round media or aspiration hole 215 is not positioned above the tissue scaffold 303 to allow for easy exchange of media while reducing the risk of contacting and damaging the scaffold 303 when the aspiration pipette is inserted through the hole (see, e.g., FIG. 1C). A smaller aspiration hole 216 is positioned directly above the tissue scaffold 303 to allow easy direct thereto access for seeding. In certain embodiments, the smaller aspiration hole 216 is configured and sized to hold a specific standard pipette size at a set height over the scaffold to prevent contacting and damaging the same, and for forming an optimized seeding region.

On either side of the smaller hole 216 are the two downwardly extending protrusions, first anti-rotation protrusion 217 and second anti-rotation protrusion 218 that extend below the bottom wall 210 of the mask and sit on either side of the underlying scaffold 303. These protrusions 217, 218 prevent the cassette frame 320 and clips 310, 315 (supporting tissue scaffold 303) from rotating in the cup 400, restrict the flow and leakage of the seeding solution, and encourage beading and adherence of media to the lower mask surface 210. The cassette frame further comprises an attached or fixed clip 315 comprising locking slot 327. In some embodiments, the first anti-rotation protrusion 217 and second anti-rotation protrusion 218 each define an associated upwardly open removal recess 217*a*, 218*b* (FIG. 17) which are spaced to allow squeezed-together forceps to be inserted and then released thereby exerting an outward pressure within the recesses/protrusions 217, 218 which allow the mask 200 to be removed from the cup 400 (see, e.g. FIG. 15). In other embodiments, any other gripping device may be used such as a specialized tool created to fit into the first and second protrusions 217, 218. The two laterally extending external retention protrusions, first external retention protrusion 221 and second external retention protrusion 222 (see, e.g. FIG. 19A) arranged to engage the inside surface of cup 400 when the mask is inserted therein. In one embodiment, the retention protrusions may be diametrical opposed and formed on the top outwardly flared lip of the cup side wall 220. The first and second external retention protrusions, 221 and 222 respectively, create a frictional interference fit with the inside surface of the cup side wall 401 (see, e.g., FIG. 5A) and are locked into the bioreactor device 1000 by flexing the mask 200 into position. In certain embodiments, the side wall 220 may contain at least one external protrusion wherein the protrusion creates a geometric fit with the cup side wall 401. In certain non-limiting embodiments, the mask may comprise 2 to 6 external retention protrusions and between 1 and 6 holes.

Figure 1D:
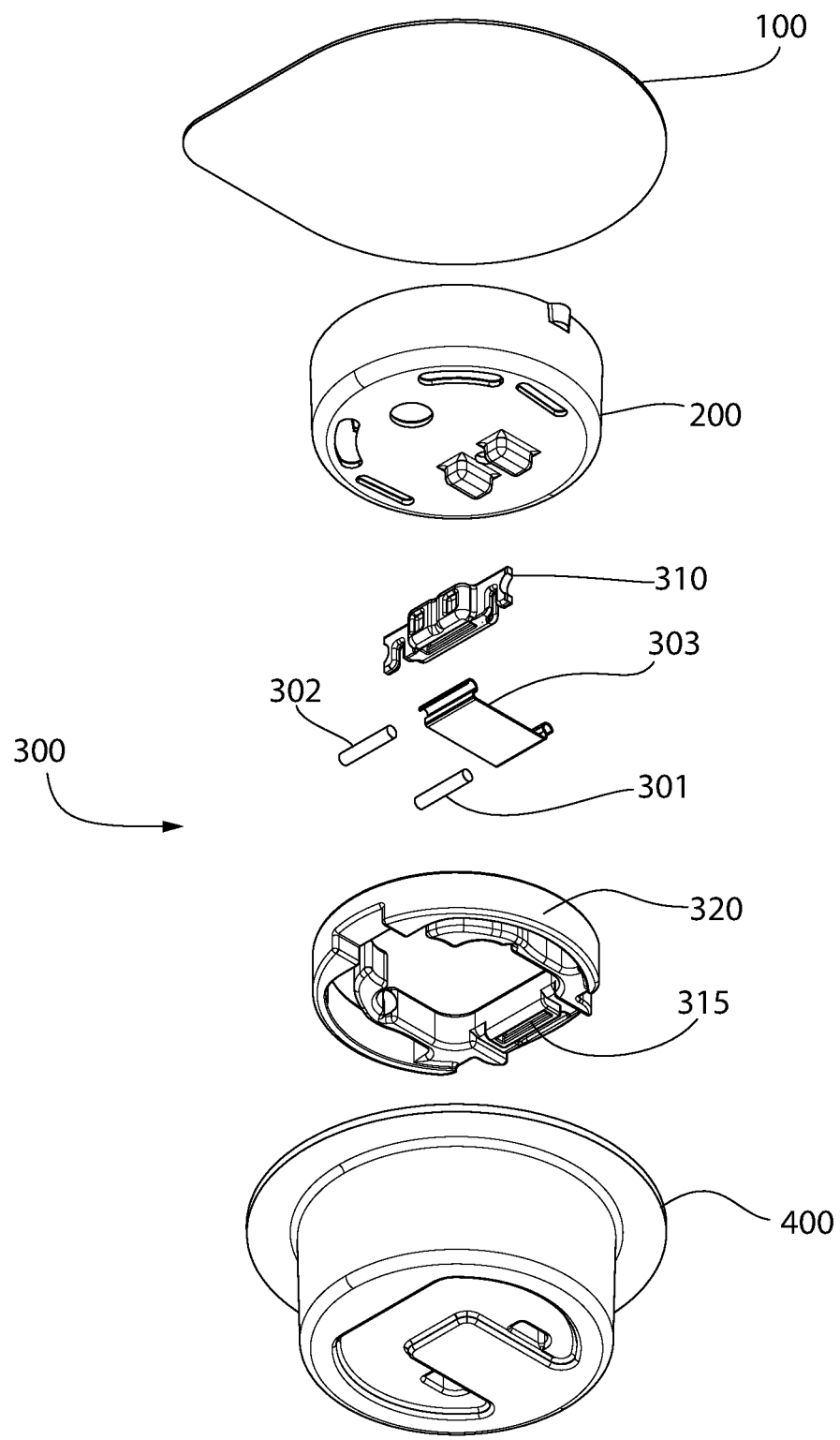

In certain embodiments, the mask 200 comprises bottom wall 210 forming a closed bottom and an upstanding cylindrical sidewall 220 configured to slideably engage a cylindrical sidewall of the cup 400 when the mask 200 is inserted therein (For example, as shown in FIGS. 1D, 2A, and 1D, 2A, and 1D, 2A, and 5A). The top of the mask 200 is open to provide access to the multiple through holes as described elsewhere herein.

Cassette

Figure 3A:
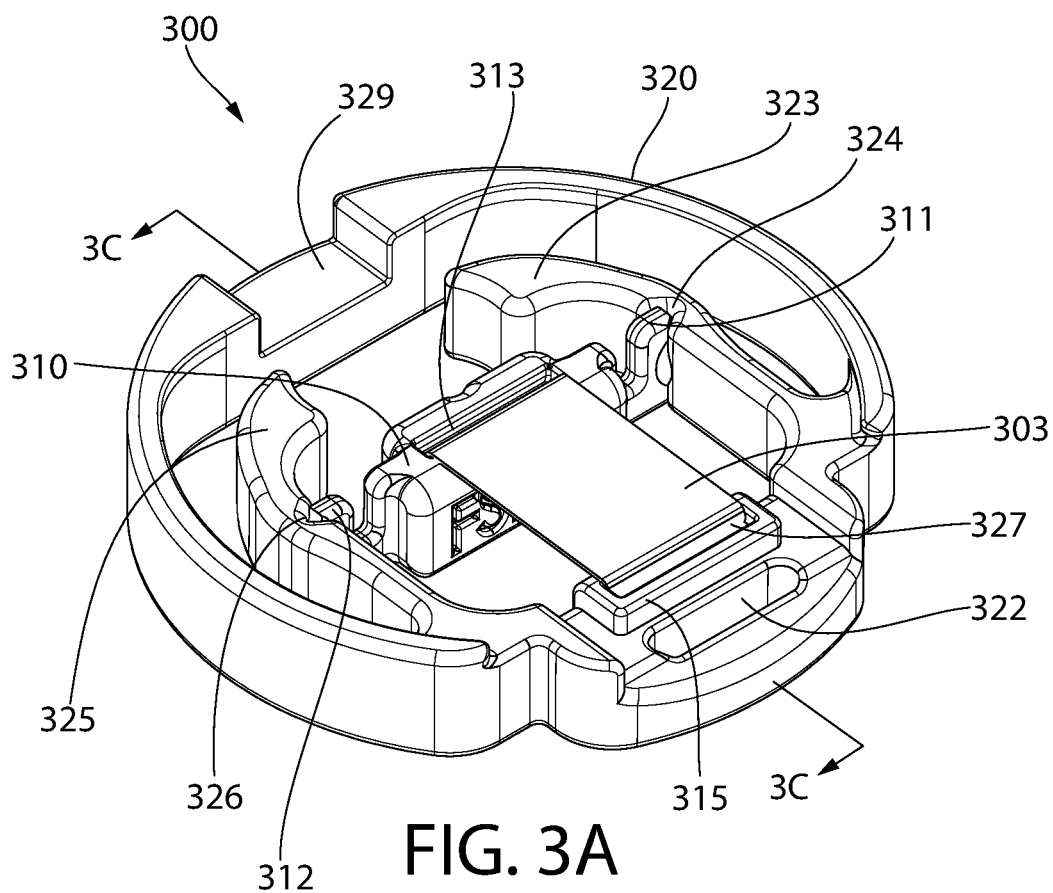
FIGS. 3A-3C depict a cassette according to one embodiment.
Figure 3B:
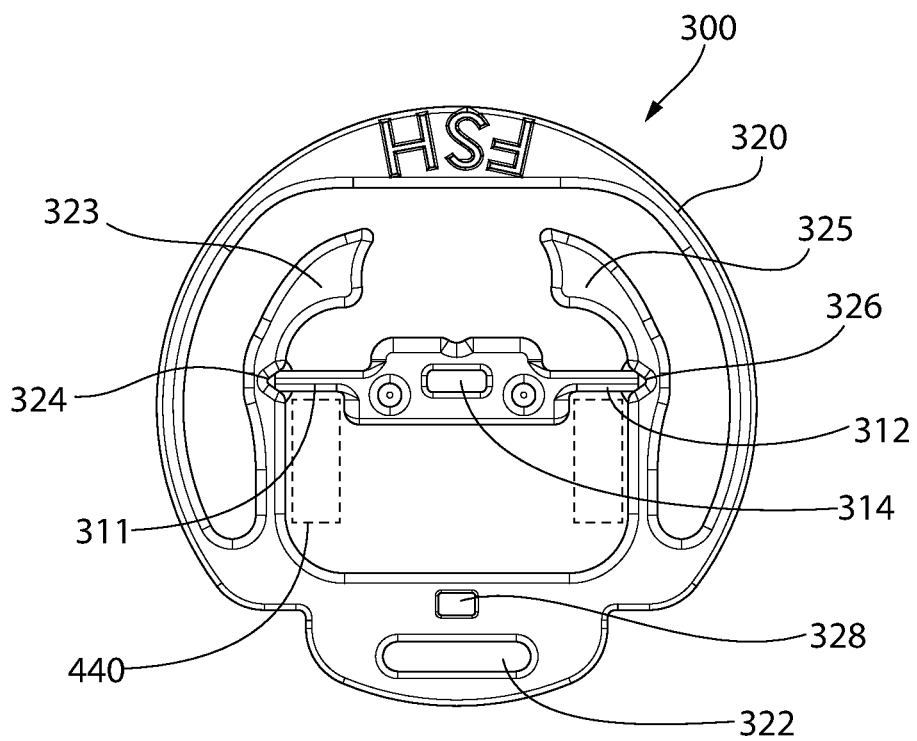
Figure 3C:
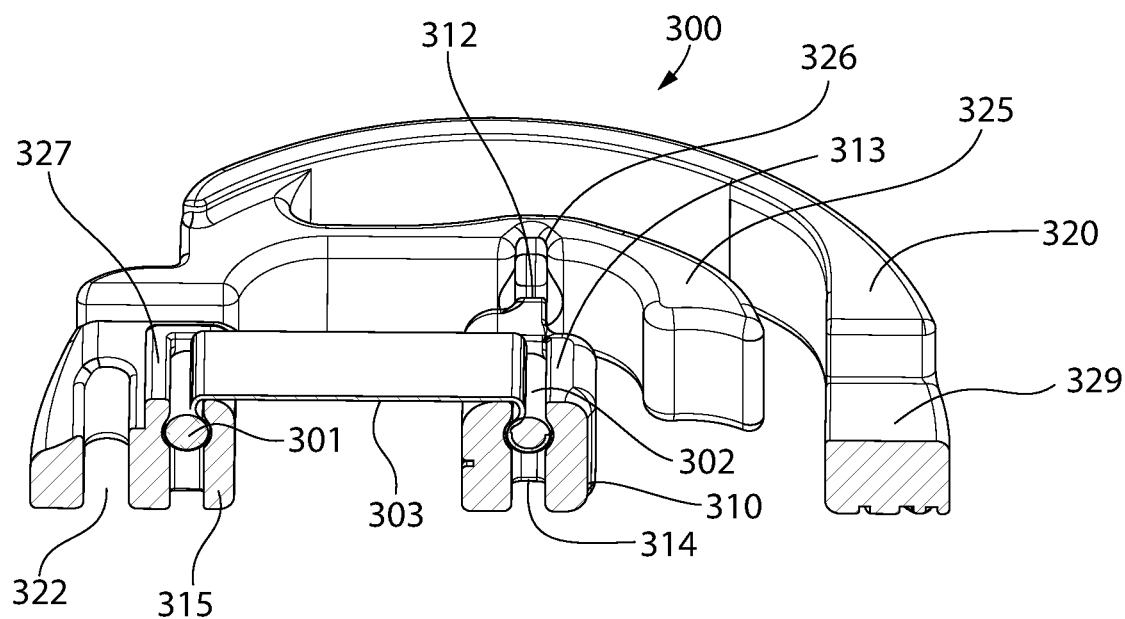

Referring to FIGS. 3A through 3C, the exemplified cassette 300 contains the tissue scaffold 303 supported by integral fixed clip 315 and detachable or floating clip 310. The detachable clip 310 may be selectively detached from the cassette 300 as shown in FIGS. 30A-31B when performing tensile testing of the tissue scaffold 303 and the grown tissue specimen thereon with testing instrument 2000. The detachable clip 310 is temporarily engaged with the cassette frame 320 to form a geometric lock designated as the first and second flexible arm lock (324 and 326 respectively) which are formed between the opposing edges or ends of both the first detachable clip arm 311 and second detachable clip arm 312 of the detachable clip 310 and two resiliently flexible and movable spring arms 323, 325 of the cassette 300 (See, for example, FIG. 3B). In the exemplified embodiment, the cassette 300 has two flexible spring arms 323, 325 but in other embodiments, the cassette 300 has at least one movable spring arm 323, 325.

A thin ribbon-like tissue scaffold 303 has one end connected to detachable clip locking slot 313 of the floating clip 310 and the other end connected to clip locking slot 327 (See, for example, FIG. 3A). The tissue scaffold may have a generally rectilinear configuration in some embodiments. The floating clip 310 itself is detachably coupled to the cassette 300, such as a flexible portion of the cassette frame 320 defined by spring arms 323, 325. At the opposite side of where the scaffold is inserted into the clip, there is a drainage path 314, 328 (See, for example, FIG. 3B). The base of the cassette frame 320 contains a grasping slot 322. This slot 322 could be used to easily transport the cassette 300 out of the support apparatus 400 of the bioreactor device 1000 and could be sized to allow engaging forceps to exert a positive outward force when the legs of the forceps are at their expanded rest position. In other embodiments, any other gripping device may be used such as a specialized tool created to fit into the grasping slot 322. The cassette frame 320 of the cassette 300 is configured to mount into biomedical tissue testing instrument 2000 (discussed below) as well as the seeding cup 400 of the bioreactor device 1000.

In some non-limiting embodiments, the cassette frame 320 may be made of a biodegradable or biocompatible material. Fully biodegradable material would allow for better recovery of matured tissue strips for surgical use, and fully biocompatible material would be suitable for implantation in mammals. In another embodiment, the cassette may be made of a memory alloy. The memory alloy could have stored configurations or indicate different states and chemical imbalances of the tissue.

In some embodiments, the cassette 300 may contain a radio frequency identification chip, RFID chip. The RFID chip could be used for wireless capabilities, passive reading, decoding, and/or tissue management. In other embodiments, the cassette 300 contains wireless integrated sensors. In a further embodiment, the wireless integrated sensors relay data to a central database. The sensors could relay data in real-time or at a set interval for live monitoring and automation to an electronic programmable controller.

The tissue scaffold 303 may be seeded with human or animal cells. It is understood that the cassette scaffold 303 could be seeded with any suitable cell, including but not limited to, primary cells, progenitor cells, pluripotent cells, stem cells, and other differentiable cells. The differentiable cells could be described by way of their origin such as embryonic stems cells, hematopoietic stem cells, adipose derived stem cells, bone marrow derived stem cells and other varieties. The cells could be differentiated into a variety of cells including, but not limited to, fibroblasts, osteocytes, epithelial cells, endothelial cells, myocytes and neurocytes. The preferred embodiment of the present invention is to seed human induced pluripotent stem cell-derived cardiomyocytes into the cassette scaffold 303, created from cryosectioned decellularized myocardium. However, one of ordinary skill in the art would be able to use the invention with any biological tissue or organ including but not limited to vascular, smooth muscle, skeletal, neural, skeletal muscle, epithelial, and connective tissue.

Seeding Cup

The seeding cup 400 may have a cylindrical configuration sized to fit in a cell of a standard twelve cell laboratory culture tray 700, similarly to that shown in FIG. 20B which shows a cassette 300 being inserted in the try. Accordingly, either the cup or cassette may be placed into the tray.

Figure 4A:
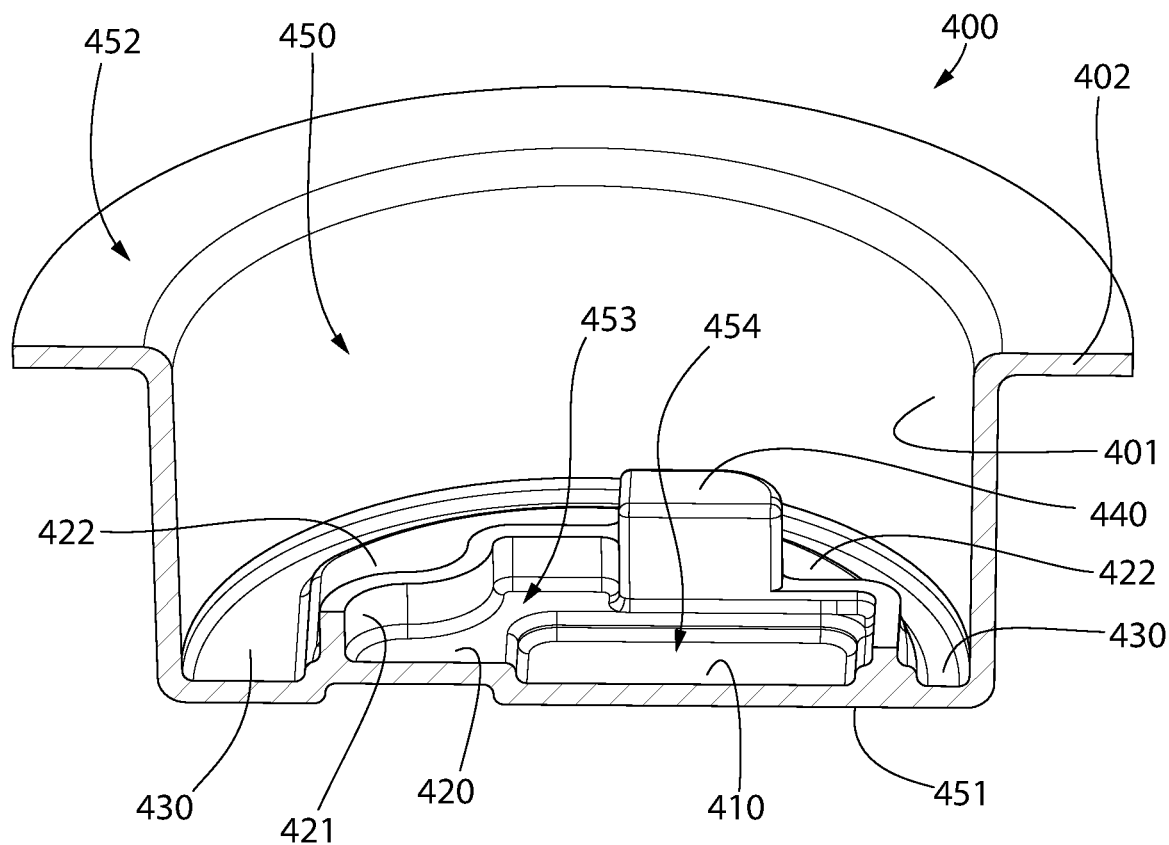
FIGS. 4A-4B depict a support apparatus according to one embodiment.
Figure 4B:
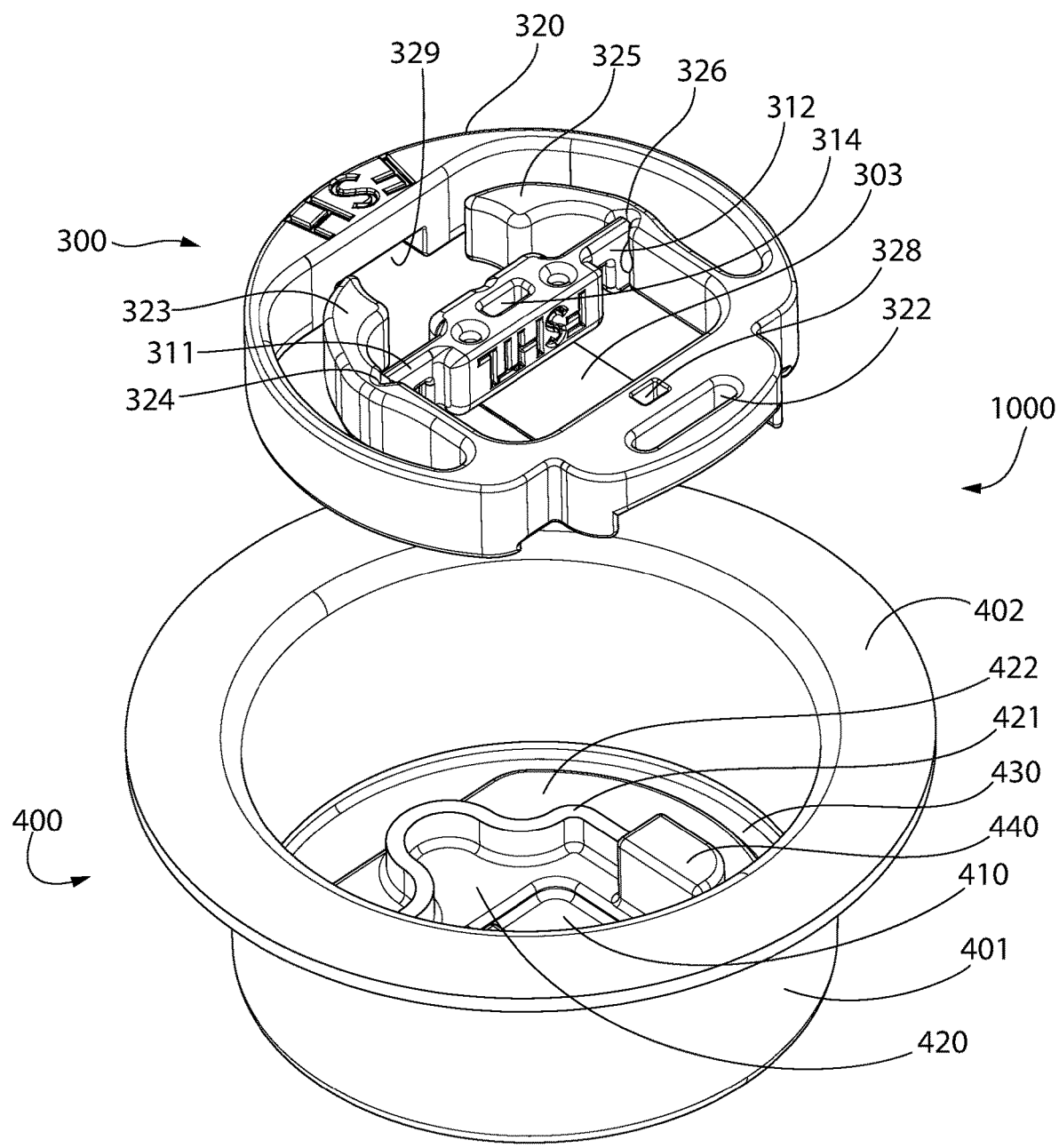
Figure 18:
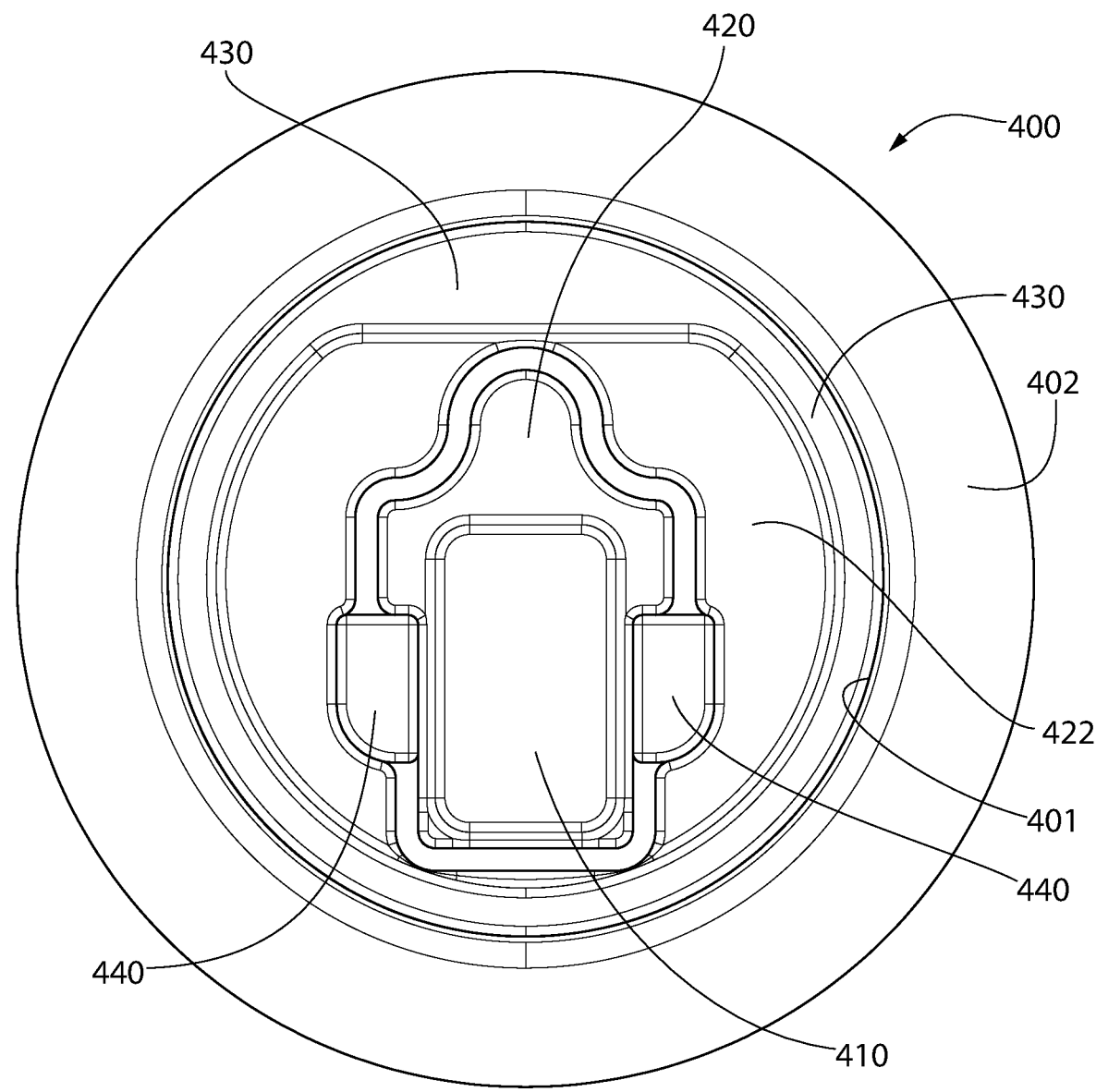
FIG. 18 depicts top down view of an embodiment of a bioreactor device. In this view, the cassette is not contained within the cup.

Referring particularly for the moment to FIGS. 4A and 18, the seeding cup 400 includes lower seeding trough 410, liquid media (fluid) exchange region 420, annular mounting détente or recess 430, and locking studs 440. The seeding trough is the lowest point of the bioreactor device 1000 and is configured to retain the media or fluid (e.g. buffered saline solution) after aspiration, as further described herein. This could prevent the scaffold 303 from decreasing in biological function and could increase the number of cells held against the scaffold 303. The seeding trough may have first floor 454 defining a lower fluid volume than second floor 453 surrounding the seeding trough inside the fluid retention wall 421; the second floor located at a higher elevation than the first floor. The immediate surrounding area beyond the seeding trough 410 is the media exchange region 420 which provides a region for media to be accessed while greatly reducing the risk of damaging the scaffold 303. The media exchange region 420 is surrounded by fluid retention wall 421 that reduces the flow of the sterile media or fluid and concentrates the fluid to the area around the scaffold 303. When the fluid is aspirated from the media exchange region 420, the lower seeding trough 410 still retains a portion of the fluid to keep the tissue scaffold 303 at least partially immersed and biologically intact and active. Cell seeding may be accomplished by inserting a pipette through the seeding hole 216 to access the tissue scaffold 303 and ejecting cell-containing solution onto the scaffold. In certain embodiments, the seeding hole 216 in the mask 200 is positioned directly above the tissue scaffold 303 for introducing cells to the scaffold through the seeding hole 216. The seeding hole 216 may be smaller than an aspiration hole. The mounting recess 430 surrounds the media exchange region 420 and may have a narrow spacing or width which constricts the size of the media exchange region 420 to restrict sterile fluid flow.

At least one upwardly extending locking stud 440 may be formed on the bottom wall 451 of the seeding cup 400 and is used to prevent movement of the cassette 300 and mask 200 within the seeding cup 400. In the non-limiting illustrated embodiment, a pair of spatially separated locking studs 440 are provided; one each on opposite lateral sides of the seeding trough 410. The locking studs 440 are the highest protrusions of the seeding cup 400 internal structures and rest against the bottom wall 210 of the mask 200 to prevent the mask from contacting and damaging the integrity of the scaffold 303. The locking studs 440 sit on either side of the mask downwardly extending bottom anti-rotation protrusions 217, 218 to prevent the cassette 300 from rotating in the cup 400 (see, e.g. FIG. 17). The inboard sides of the locking studs 440 may engage the outboard sides of the anti-rotation protrusions 217, 218 as shown to prevent the relative rotation between the mask and cup.

Around the edges of the seeding cup 400 is the annular mounting recess 430 which created a fluid flow dead zone of space. The bottom of the peripheral portion of cassette frame 320 fits within the mounting recess 430 to constrict flow and lock the cassette 300 into the proper orientation. This function is aided by the area surrounding the media exchange region 420 which may be generally flat and is a slightly elevated platform 422 (defined by a top surface of the fluid retention wall 421) that is designed to fit with the flexible spring arms of the cassette 323, 325.

Referring to FIG. 5A, the exemplified mask 200, cassette frame 320, and seeding cup 400 internal structures previously described herein nest or nestle into each other thereby forming a rotationally interlocked fit. The larger round media hole 215 is depicted as being above the media exchange region 420; laterally offset from and located to the side of the tissue scaffold 303. The smaller seeding hole 216 is shown positioned directly above tissue scaffold 303. A locking stud 440 can be seen behind the scaffold 303 and mask protrusion 217. In this embodiment, there is an empty pocket of space along the mounting recess 430 that is caused by the groove 329 formed in the bottom of the cassette frame 320 (see also FIG. 3A). This groove has importance once the cassette assembly is in the measurement device bath—it is intended to provide a flow path to allow convection/circulation of fluid under the tissue on the tissue scaffold 303 during testing in instrument 2000 to facilitate fluid transport into/out of the tissue.

Figure 5B:
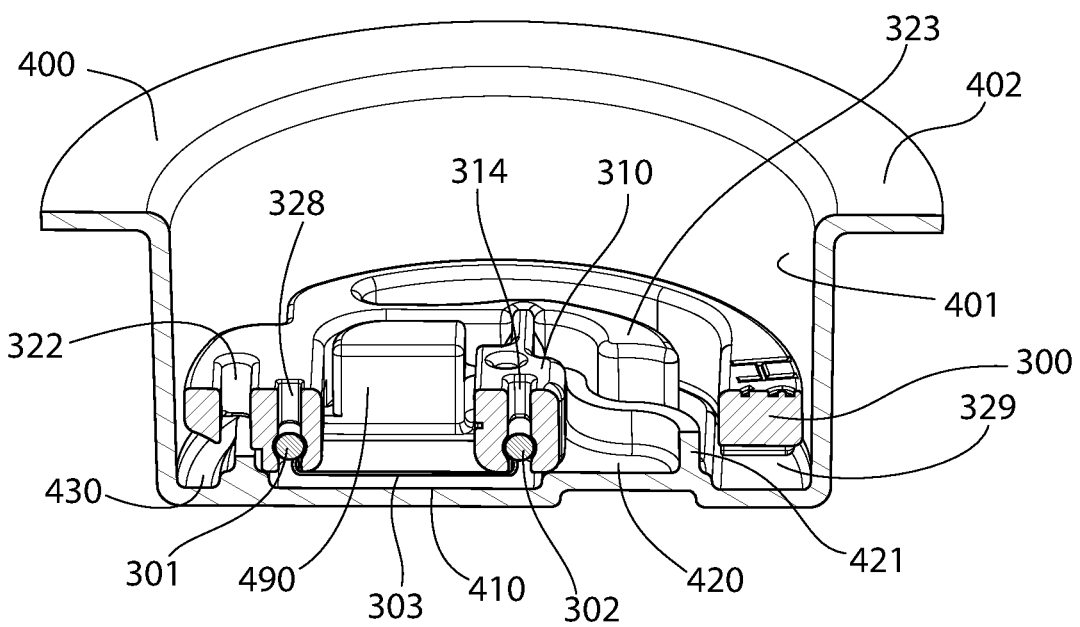
FIG. 5B depicts a cross section of a consumable bioreactor cup with a cassette and support apparatus according to one embodiment. A lid and mask have been omitted.

FIG. 5B depicts the same construction except the mask 200 has been removed.

Biomedical Instrument

Figure 6A:
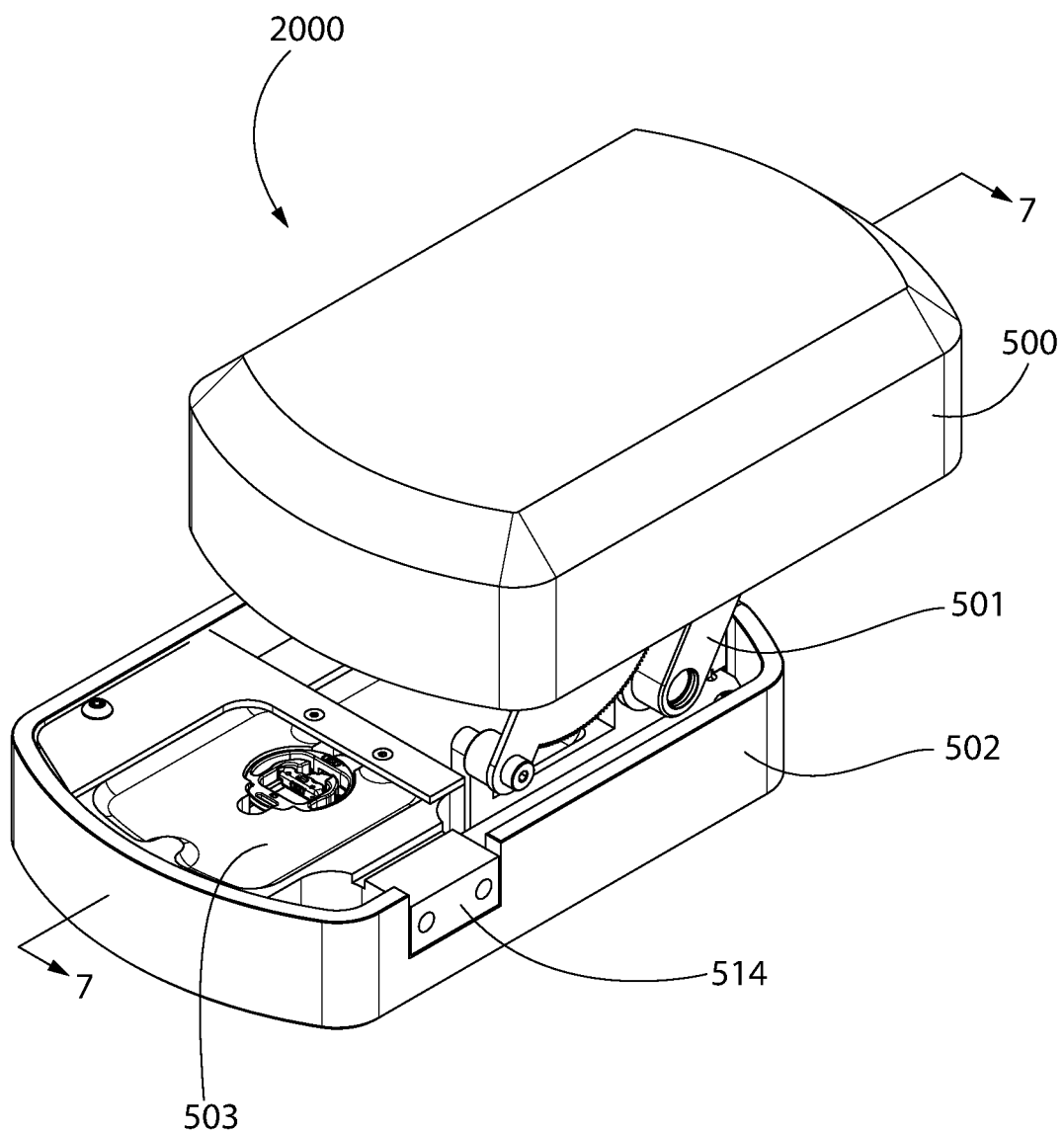
FIGS. 6A-6B depict a biomedical instrument, or biomechanical testing system, according to one embodiment.
Figure 6B:
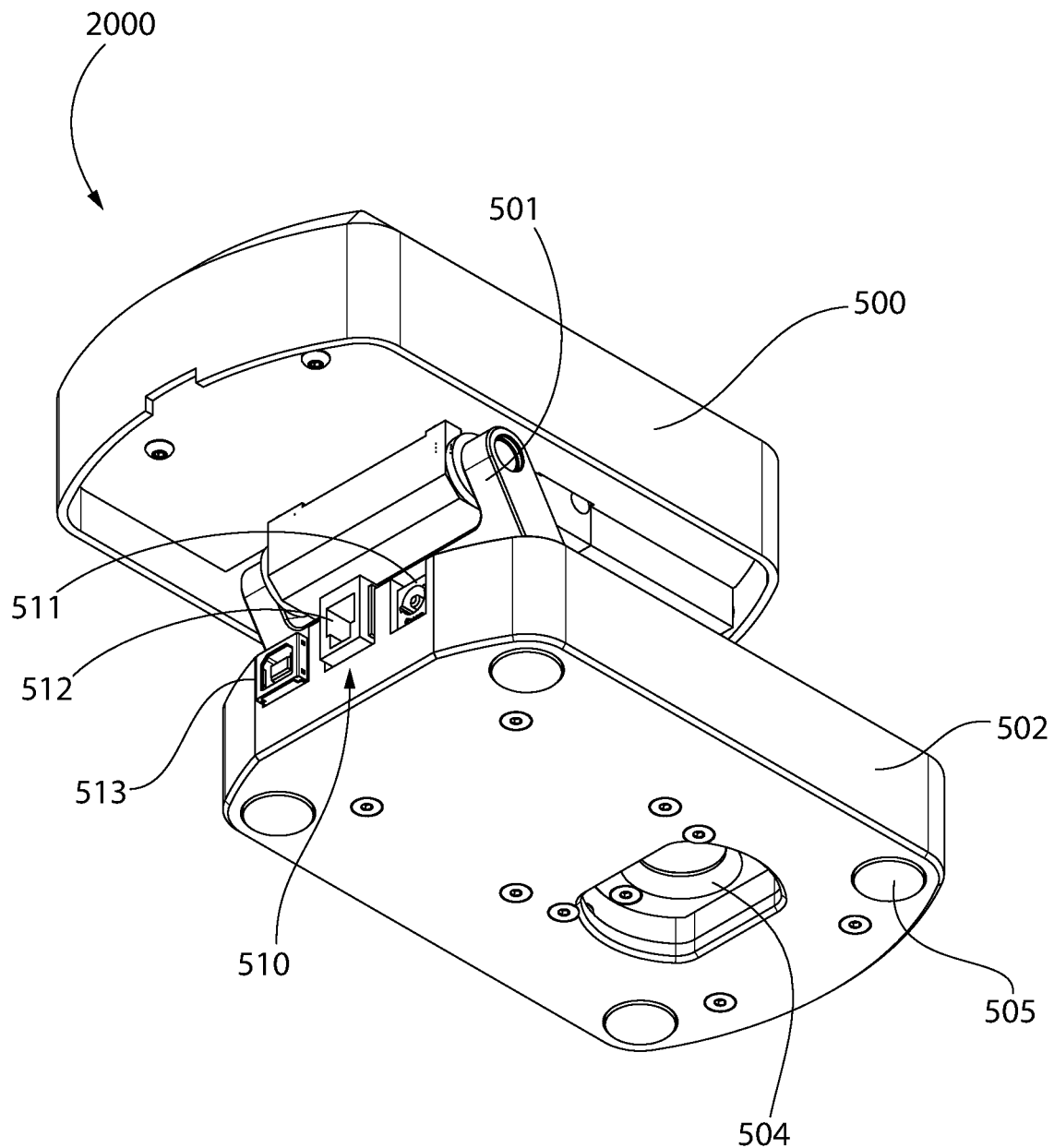

Referring generally to FIGS. 6A-10 and 21-35, a biomedical tissue testing instrument 2000 and components thereof according to one embodiment are shown. In certain embodiments, the instrument may be a bench-top instrument. In the exemplified embodiment, the instrument 2000 has a body comprising an upper housing 500 and a lower housing 502. The housings may be generally rectilinear (e.g. square or rectangular) in one non-limiting embodiment as shown; however, any suitable polygonal or non-polygonal shape (e.g. oval, circular, etc.) may be used. The upper housing 500 may define an upper cavity. The lower housing 502 may define a lower cavity. The lower housing 502 may comprise a testing bath block 503 including an upwardly open receptacle 506 configured for holding a fluid and removably receiving the cassette 300 therein for tissue analysis (See, for example, FIG. 6A). The upper housing 500 and lower housing 502 are movably coupled together.

In certain embodiments, the two housings may be hingedly connected together by a hinged closed chain linkage opening mechanism 501. The closed chain linkage opening mechanism 501 is operable to separate and close the upper housing 500 and lower housing 502, and in certain embodiments this mechanism is automated. The upper housing 500 may be movable between an open position spaced apart from the lower housing 502, and a closed position engaged with the lower housing 502.

Referring particularly to FIGS. 6-7 and 23-24, the chain linkage opening mechanism 501 in one configuration comprises a pair of elongated hinge links 520 each having a lower end pivotably coupled to the lower housing 502 via a pinned connection and an upper end pivotably coupled to the upper housing 500 via a pinned connection. One hinge link 520 may be provided on each opposing parallel long side of the housings 500, 502. This creates a dual pivoting action which in one embodiment is operable to keep each housing 500, 502 parallel to each other when the upper moves between the closed and open positions. Advantageously, this ensures that that testing devices supported by the upper housing (e.g. force transducer cantilever, electrode, etc.) remain vertical and enter the receptacle in the bath block 503 containing the cassette 300 in a downward insertion direction for precise insertion into the allocated space in the cassette, which avoids damaging the tissue scaffold 303 and tissue specimen grown thereon. Accordingly, the upper housing 500 translates horizontally relative the lower housing 502 and becomes vertically offset therefrom when moved from the closed position to the open position as shown. In the open position, no portion of the upper housing 500 may contact the lower housing 502 in some embodiments. It bears noting that either the upper or lower housing may be moveable to engage the other half. Alternately, in yet other possible constructions, neither the upper or lower housing may be moveable with respect to each other in which the cassette 300 may be loaded through a slot loading tray, or rotating tray into testing instrument 2000.

Figure 24:
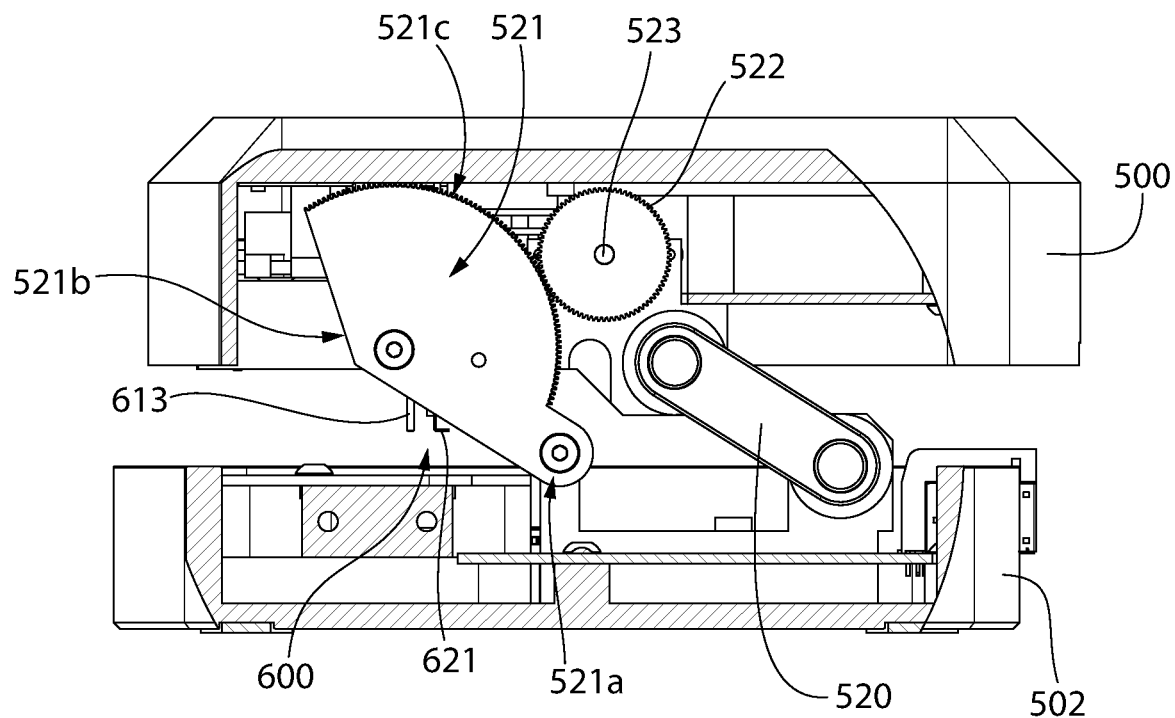
FIG. 24 depicts a cross sectioned right side view of the instrument in an open position. This view portrays positioning of certain components within the instrument.
Figure 25:
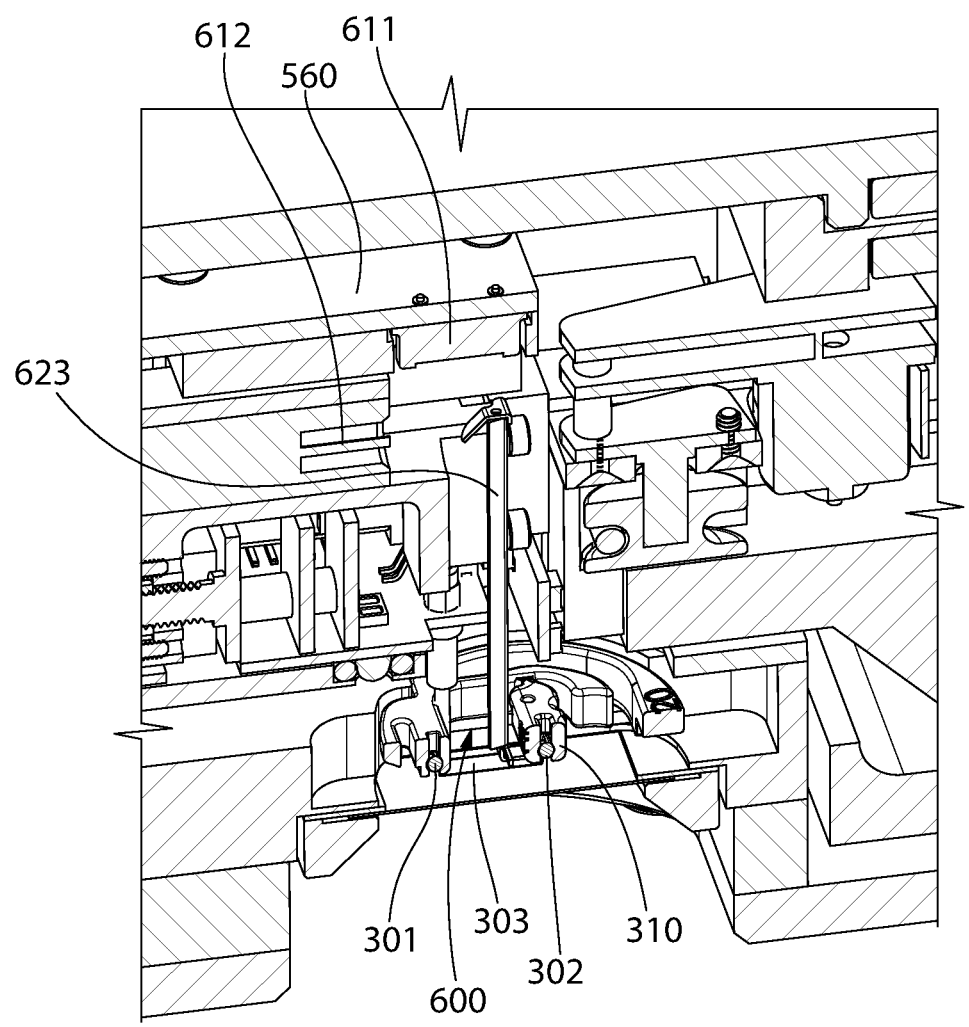
FIG. 25 depicts cassette interface components of the instrument.
Figure 26:
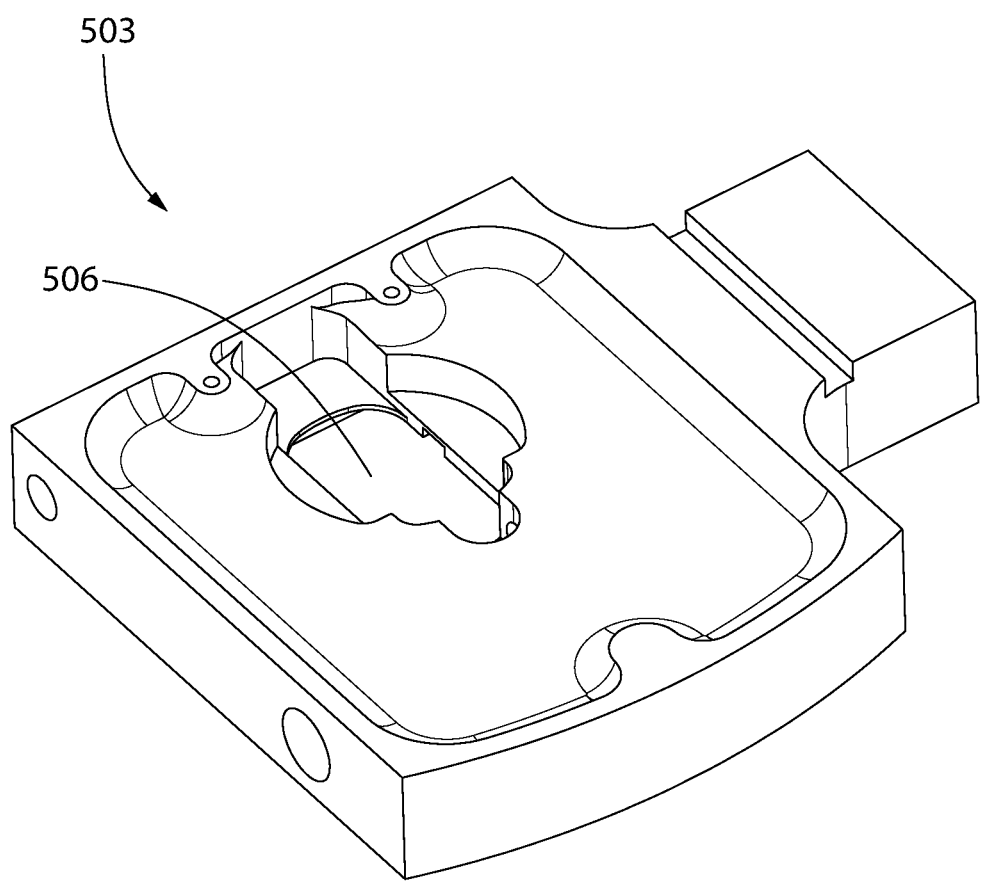
FIG. 26 depicts a bath block component. In this embodiment, the block has a modular design.

The instrument chain linkage opening mechanism 501 further comprises an elongated gear bar 521 having a lower end 521a pivotably coupled to the lower housing 502 and an upper enlarged end 521b pivotable coupled to the upper housing 500. The enlarged end 521b in one embodiment includes a gear rack 521c operably meshed with a drive gear 522 mounted on the drive shaft of electric housing drive motor 523 fixedly mounted to the upper housing 500. The gear rack may be arcuately curved in one as best shown in FIG. 24, which forms a gear segment. As the motor rotates in opposing directions as selected, the drive gear 522 which remains in a fixed position relative to the upper housing 500 closes or opens the upper housing of instrument 2000 by engaging and advancing or retracting along the gear rack 521c. Operation of the housing drive motor 523 may be controlled in one embodiment by microcontroller 560 which is operably coupled to the drive motor.

The instrument 2000 can be locked in either the open or closed positions. When the biomedical instrument 2000 is in the open position (See FIGS. 6A and 6B), the user has access to the bath block 503 for placing the cassette 300 in the receptacle 506 (see, e.g. FIG. 26). When the instrument 2000 is closed (See FIG. 22), the chain linkage opening mechanism 501 would keep the upper housing 500 and lower housing 502 parallel and aligned to each other for secure closure. This would allow the cassette interface 600 to be kept in a near vertical position as it enters the bath block 503. This also prevents any disturbance of the sample and allows the biomedical instrument 2000 to initiate sample characterization and analysis.

Figure 30A:
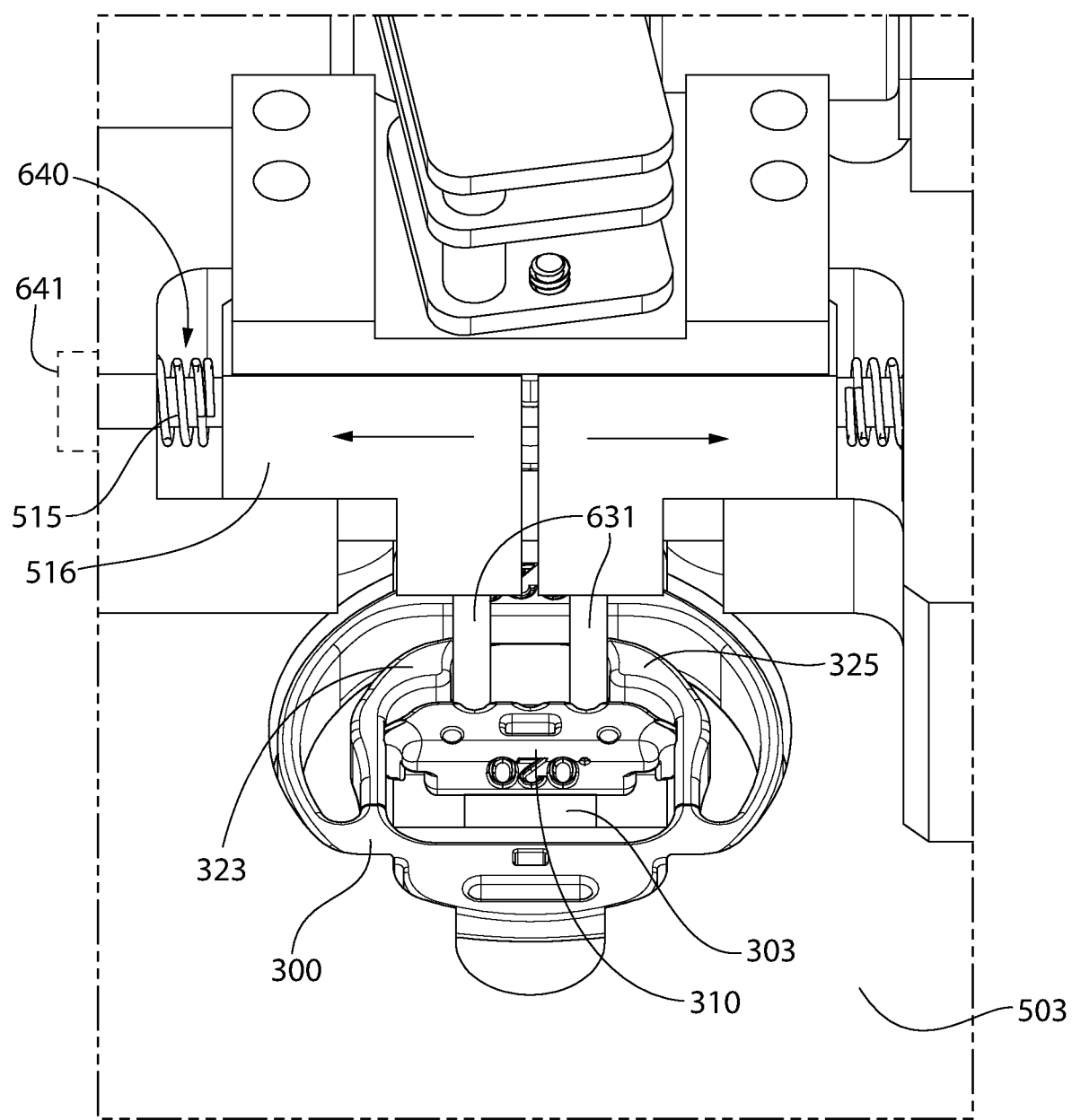
FIG. 30A depicts the spreader pins cantilevered moving in an outward motion to grab the spring arms of the cassette.
Figure 30B:
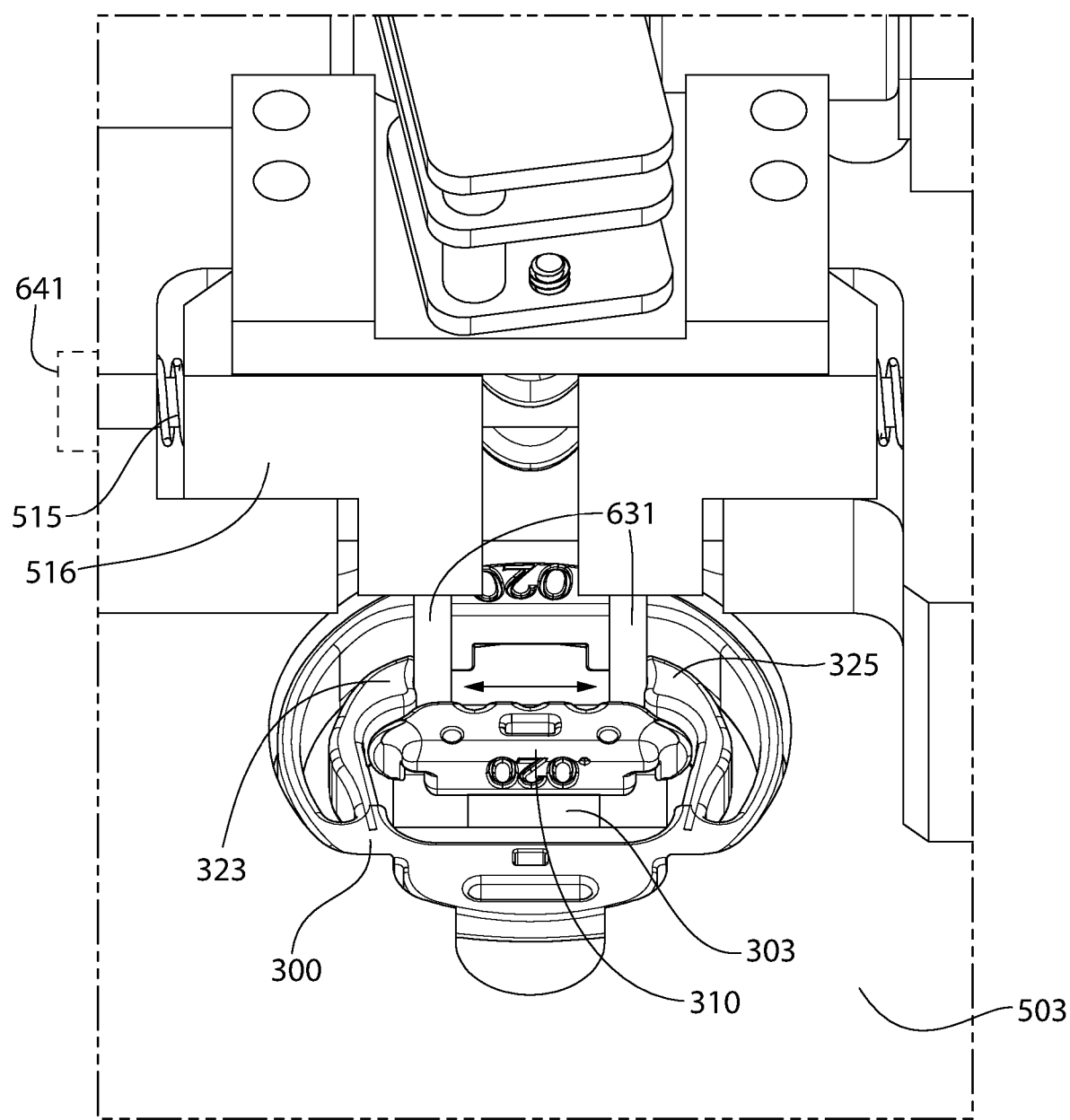
FIG. 30B depicts the spreader pins in outward positions which enable them to push out the cantilevered spring arms which effects the release of the floating clip from the cassette.
Figure 31A:
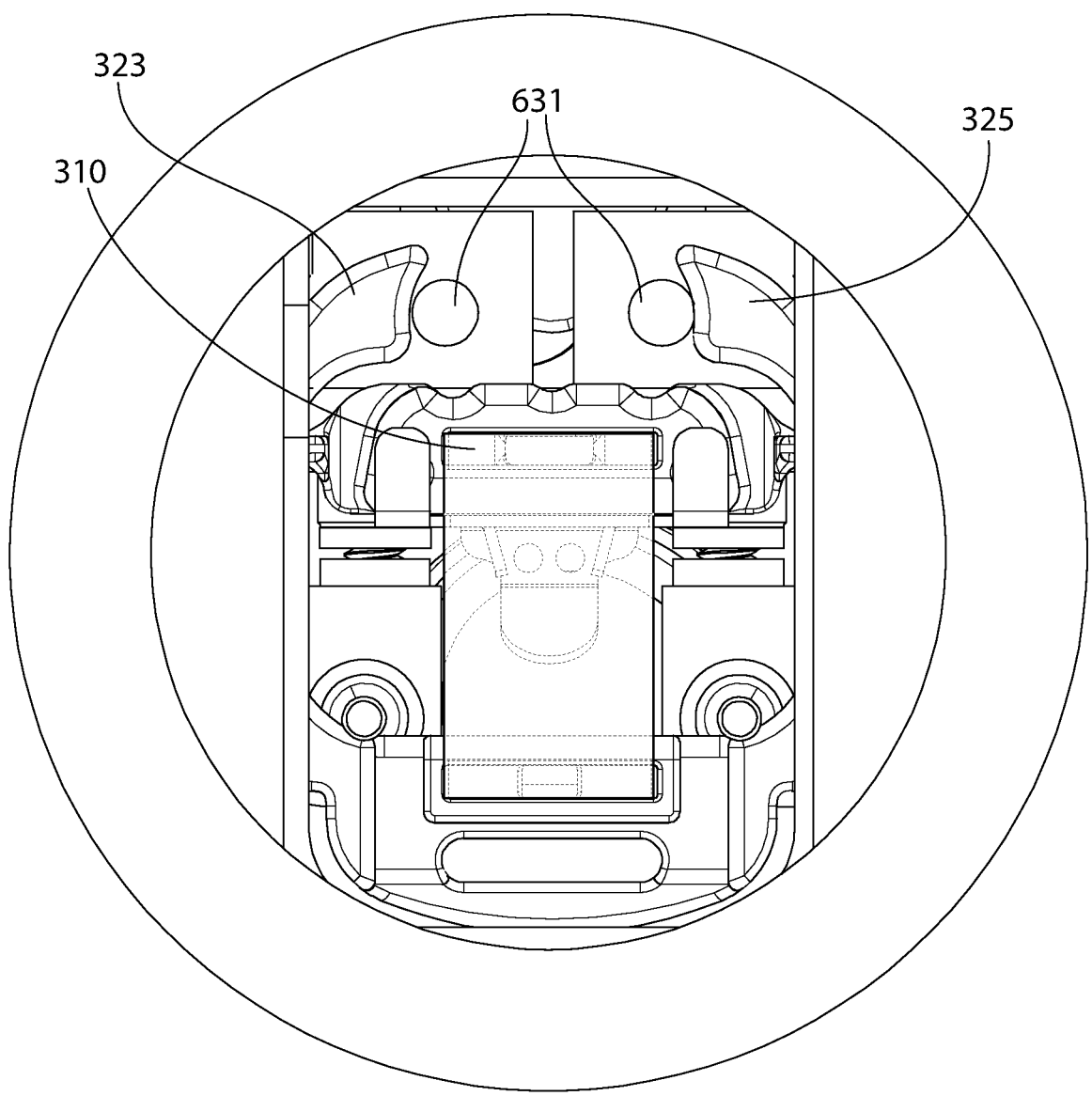
FIG. 31A depicts a bottom view through the glass window of the instrument. In this depiction, the spreader pins are grabbed with the cantilever spring arms. The floating clip is still engaged with the cassette frame.
Figure 31B:
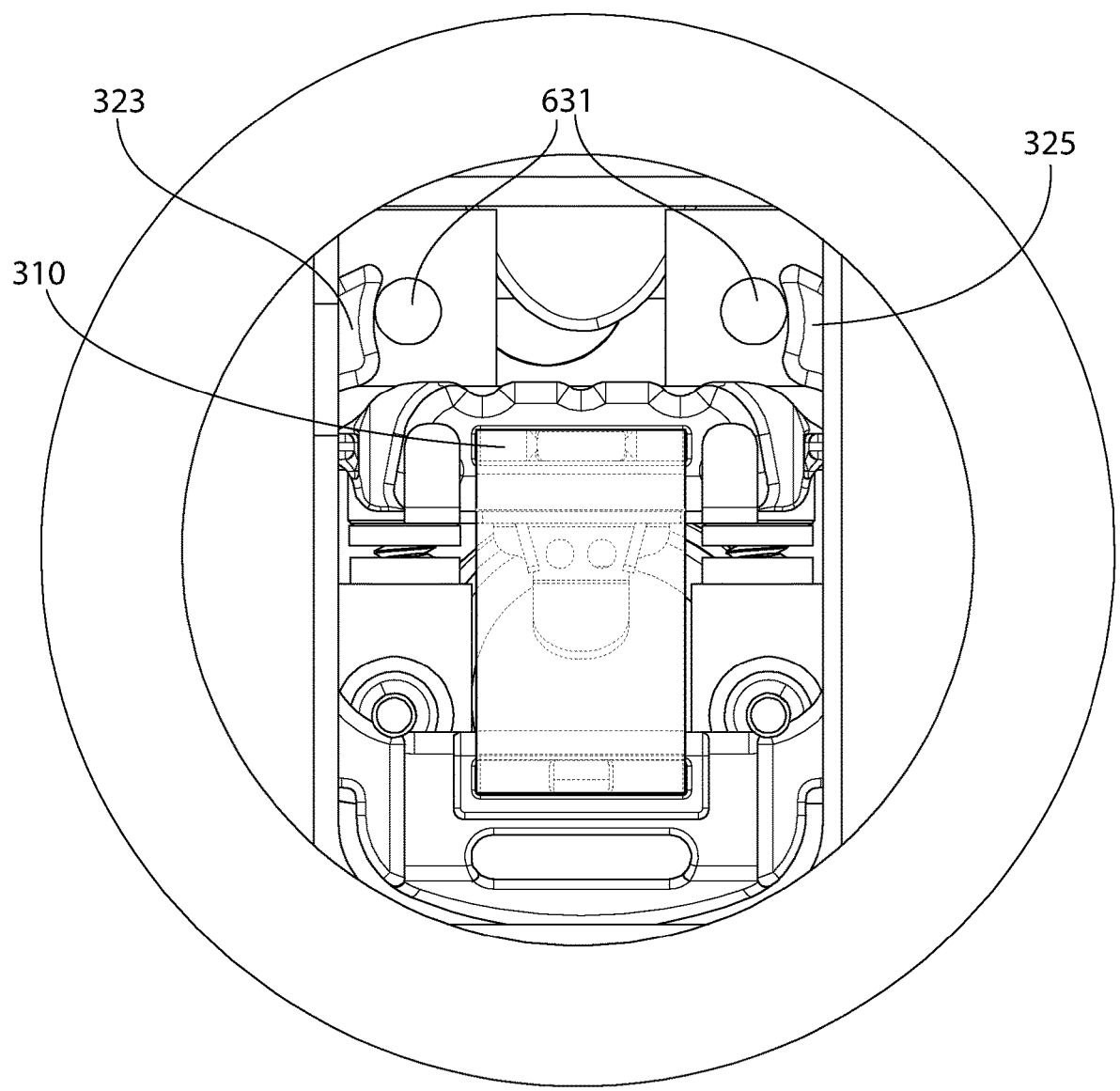
FIG. 31B depicts a bottom view through the glass window of the instrument. In this depiction, the spreader pins have pushed apart the cantilever spring arms. Under these conditions, the floating clip fully is released from the cassette frame and rests on the cantilever.
Figure 32:
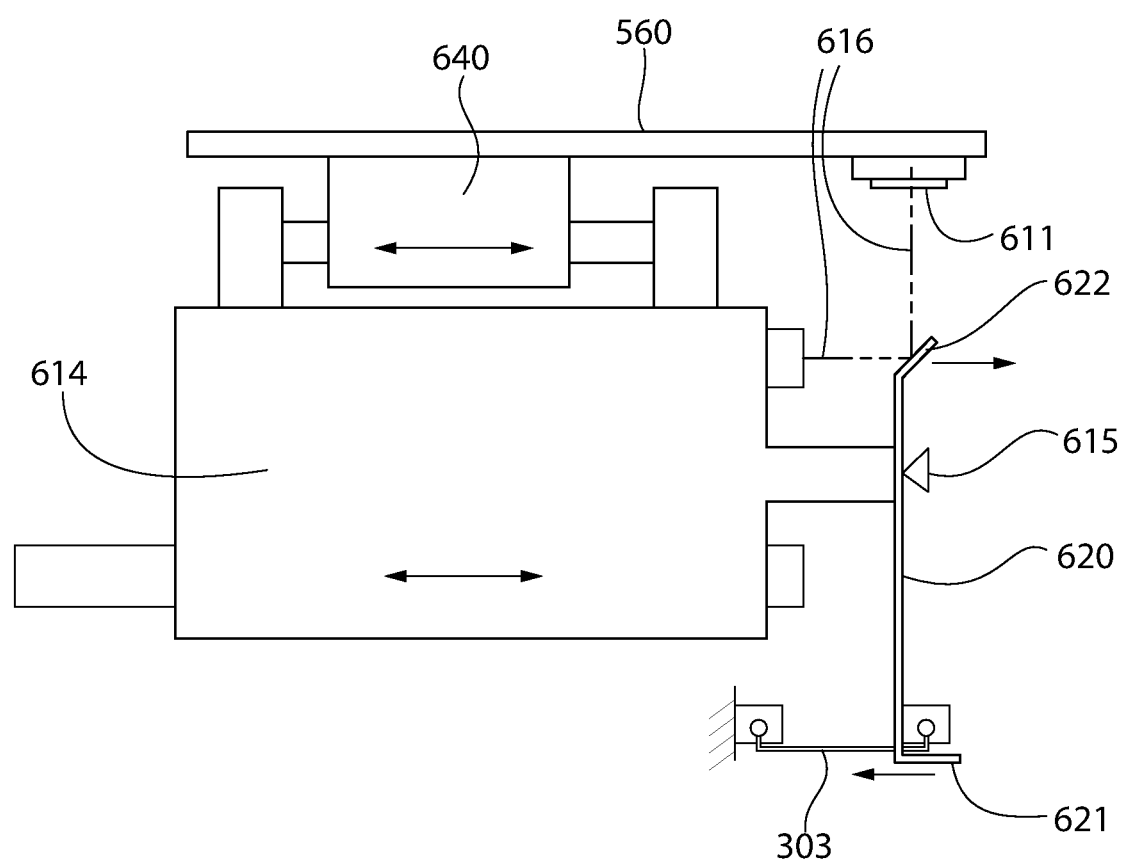
FIG. 32 depicts a side view of the force transducer component.
Figure 33A:
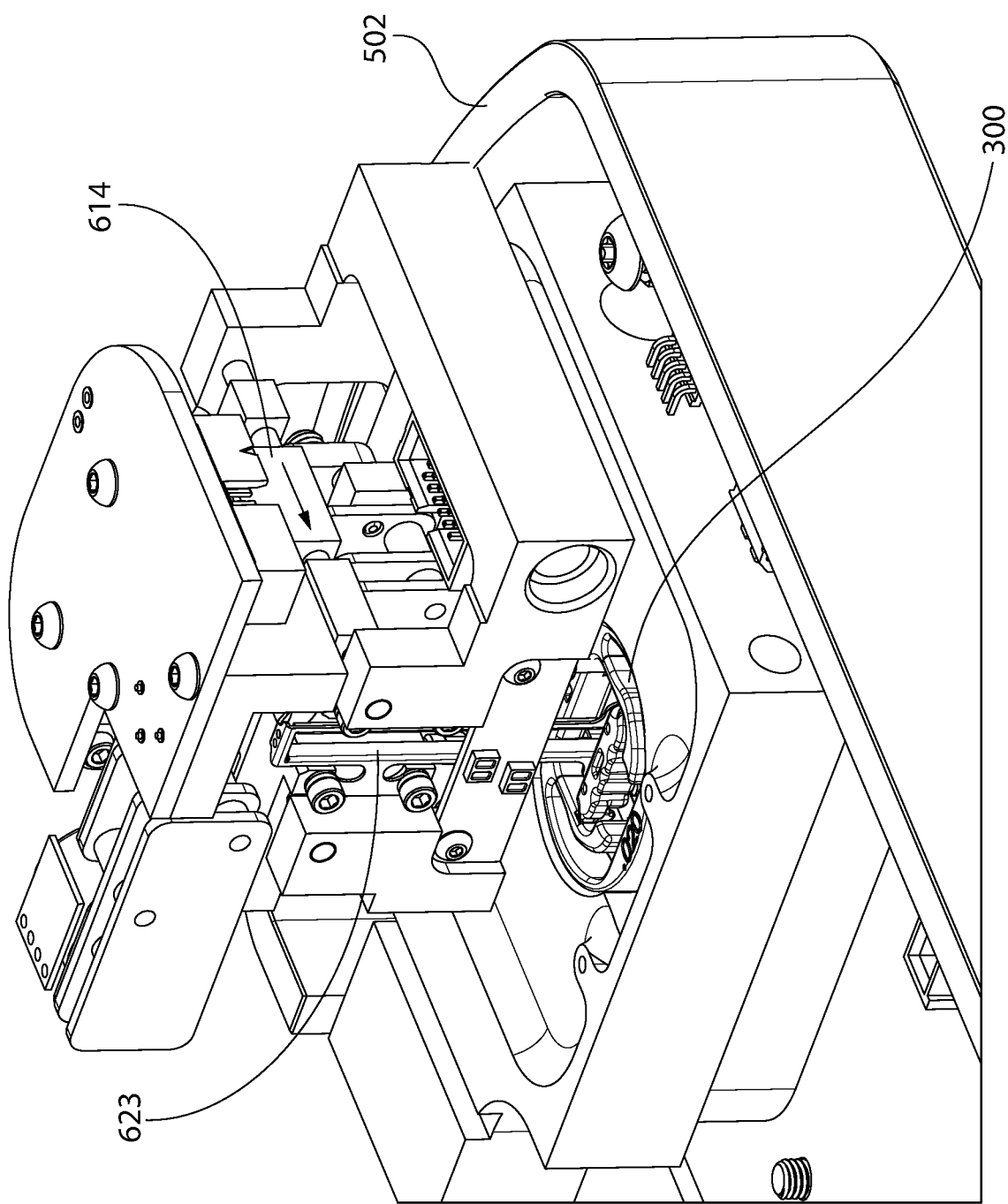
FIGS. 33A-33B depict a front-side view of the sensor and batch components within the biomechanical testing system.
Figure 33B:
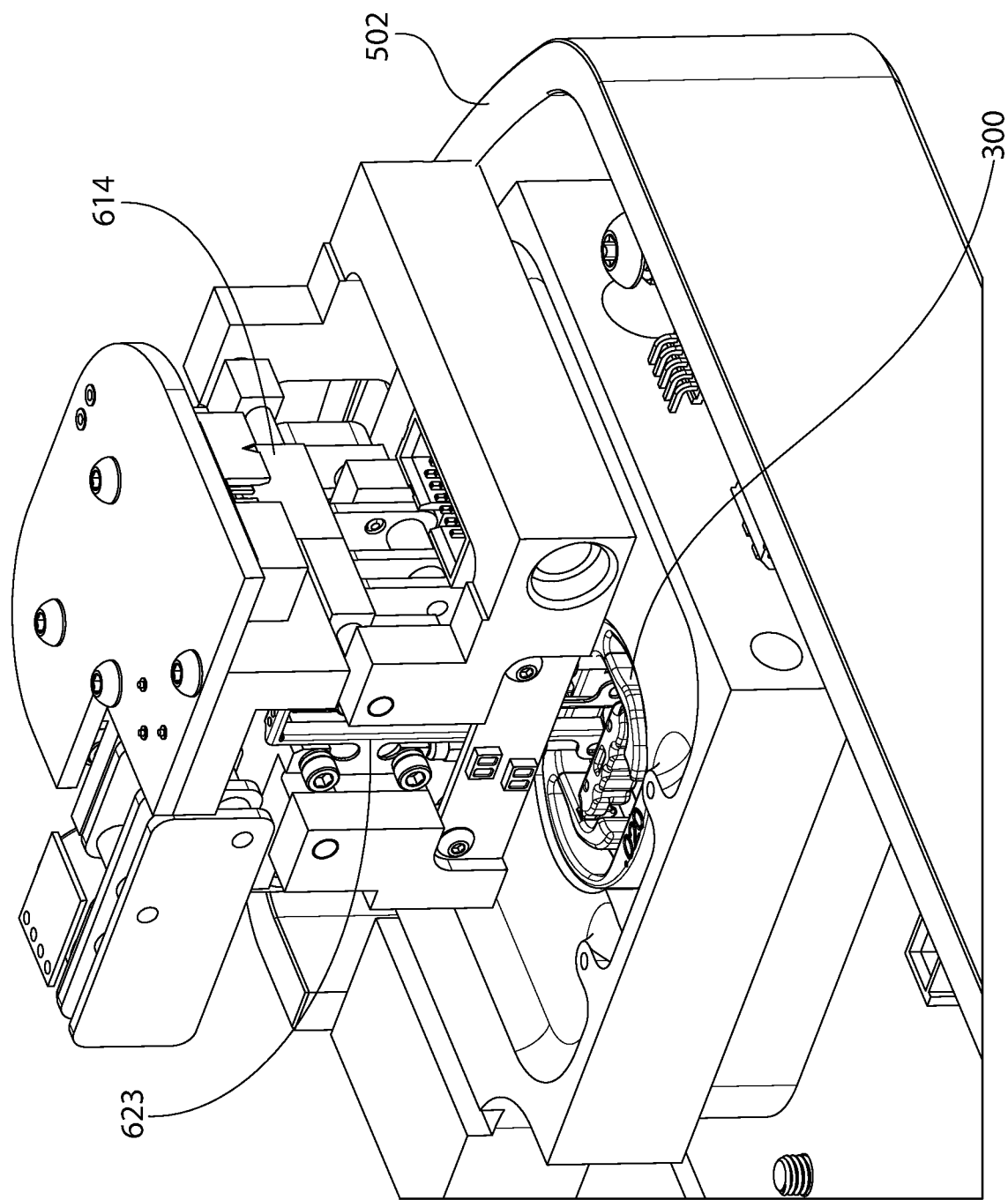
Figure 34:
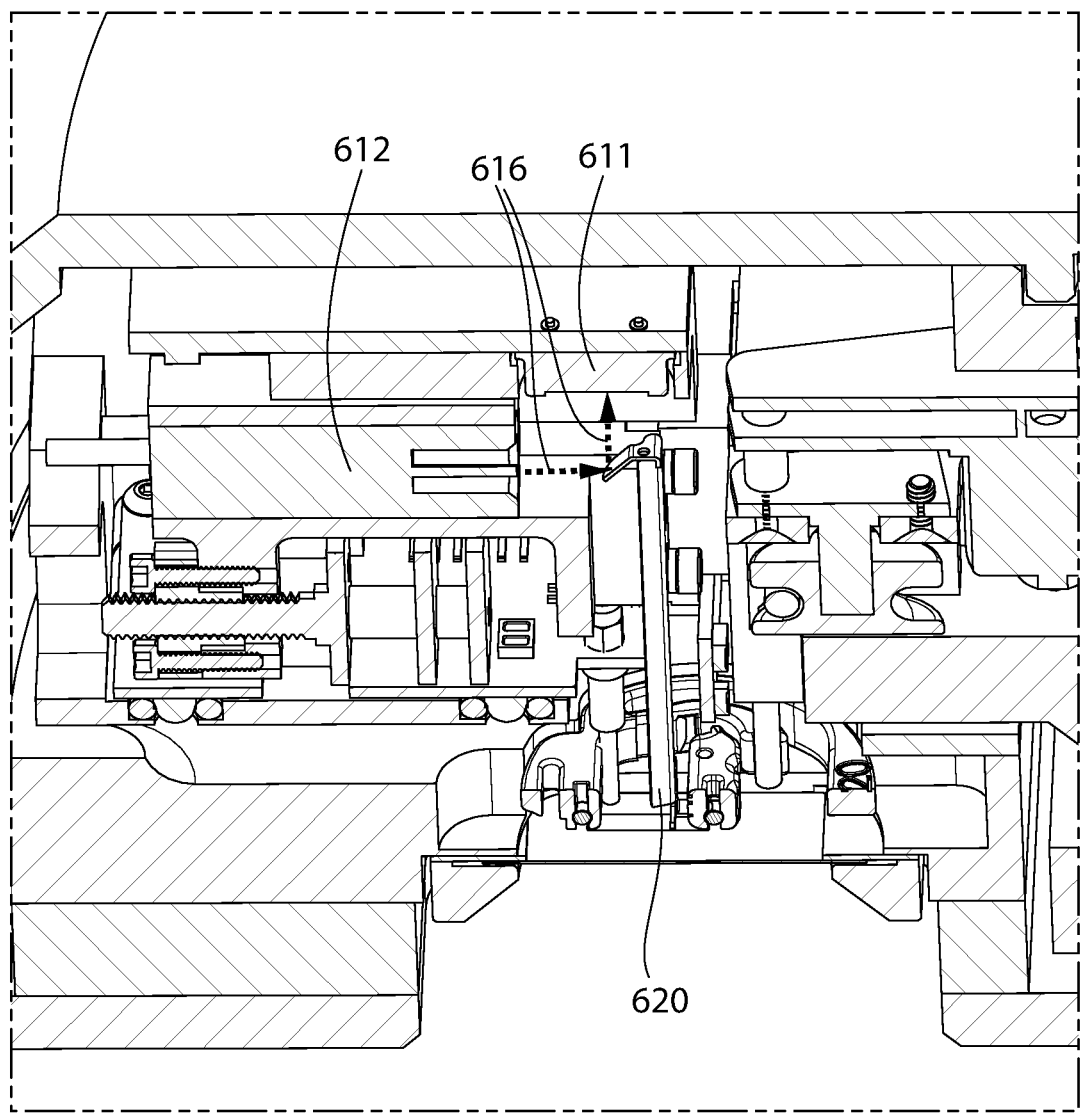
FIG. 34 is a close-up view of the cassette interface and laser components of the instrument.

Referring to FIGS. 30A-B, the biomedical tissue testing instrument 2000 may further comprise a pin drive mechanism 640 comprising a pair of spreader pins 631 operably engageable with the resiliently flexible cantilevered spring arms 323, 325 of cassette 300 when positioned in the receptacle 506 in the lower housing 502. As noted elsewhere herein, the spring arms selectively retain detachable floating clip 310 of the tissue scaffold 303 assembly to the cassette frame 320 depending on whether the arms are together or spread apart. Programmable microcontroller 560 may be operably linked to and control operation of the pin drive mechanism 640. The pin drive mechanism 640 may comprise a threaded drive shaft 515 which operably engages a pair of pin mounting blocks 516 each movably supporting one of the spreader pins 631. Acme type drive threads may be used in one embodiment which engage mating threaded openings in the mounting blocks 516. The drive shaft 515 is coupled at one end to electric drive motor 641 (shown schematically in dashes lines in the above referenced figures).

The microcontroller 560 may be configured to selectively control operation of drive motor 641 to move the pins 631 together and apart in opposing directions (See, for example FIGS. 30A and 30B). Accordingly, rotating the drive shaft in one direction via operation of the drive motor moves or spreads the mounting blocks 516 and concomitantly pins 631 apart, while rotating the drive shaft in the opposite direction draws the blocks and pins together. The pin drive mechanism 560 may be mounted in the upper housing and the pins protrude vertically downwards therefrom (See also FIG. 7). The pins 631 may project at least partially into the cassette receptacle 506 in the lower housing 502 of testing instrument 2000 to engage the spring arms 323, 325 of the cassette when the upper housing 500 is moved to the closed position. As shown in FIGS. 30A-B, the spring arms 323, 325 of cassette 300 may be moveable via operation of the pin drive mechanism 640 between a collapsed position which locks the floating clip 310 of the tissue scaffold assembly to the cassette, and an expanded position which unlocks the clip from the cassette.

In the exemplified embodiment, the lower housing 502 of instrument 2000 may also include shock absorbing feet 505 for resting on a flat support surface. Under the bath block 503, the instrument 2000 may include a polymeric or glass window 504 that could provide microscope access for examining the tissue specimen held by the cassette 300 in the receptacle 506 of the batch block. In other embodiments, the window 504 is made of any transparent material.

Outer Shell

In a preferred embodiment, the outer shell of the upper and lower housings 500, 502 may be made of metal, though the invention is not so limited. In other embodiments, for example, the outer shell is made from a memory alloy, plastic, or derivatives thereof. In some embodiments, the outer metal shell of lower housing 502 has at least one external port 510. In the embodiment depicted in FIG. 6B, the outer metal shell of the lower housing may include a first power port 513 for connecting an external power source, a second communication port 512 corresponding to serial communication port 2001 of the microcontroller 560 for connection to an external computing device such as personal electronic device 2003, a third pump control port 511 for a fluid pump control under control of microcontroller 560, and a pair of fluid exchange ports 514 for fluid exchange between the pumps and fluid retained in the cassette receptacle 506 of the lower housing. In some embodiments, a single port may be used for all necessary inputs and outputs. This single connection could include both electric lines, fluid lines, communications, or any other resource needed to operate the instrument 2000. In some embodiments the single port uses a quick connect/disconnect cable that could be configured and constructed to create a watertight seal.

Control System with Microcontroller

In some embodiments, the testing instrument 2000 has a control system which includes a configurable management unit in the form of microcontroller 560. Microcontroller 560 is configured and operable to direct operation of the instrument and tissue testing protocols. As examples, the microcontroller can be programmed to automatically conduct a series of physical tests on the tissue sample supported on tissue scaffold 303, and further store, heat, and mix a solution to be used for fluid exchange. In certain embodiments, the microcontroller could be configured to clean the instrument and dispose of waste. Further, the microcontroller could have functions such as data processing and imaging capabilities. In some embodiments, the microcontroller could be configured to perform other laboratory tests including but not limited to histological staining, calcium imaging, genotyping, fluorescence imaging, immunoassays, spectrophotometry, and electrophoresis. It will be appreciate that the microcontroller can be programmed to control an direct numerous other functions of the testing instrument 2000.

Programmable microcontroller 560 for controlling operation of the testing instrument 2000 may include the customary components and appurtenances necessary for a fully functional electronic device, including generally, for example, without limitation a programmable processor, a bus, input/output devices, graphical user interfaces, wired and/or wireless communication interface devices (e.g., Wi-Fi, Bluetooth, and/or LAN) volatile memory, non-volatile memory, electric power supply (e.g. hardwired line or transformed voltage or battery power), etc. The non-volatile memory may be any type of non-removable or removable semi-conductor non-transient computer readable memory or media. Both the volatile memory and the non-volatile memory may be used for saving data received by the microcontroller via various sensors or from other devices, for storing program instructions (e.g. control logic or software) implemented by the microcontroller, and storing operating parameters (e.g. baseline parameters or set points) associated with operation of the actuator control system. Microcontrollers described herein may be any central processing unit (CPU), microprocessor, computational, or programmable device or circuit configured for executing computer program instructions (e.g., code). Various microcontrollers may be embodied in a computer and/or server hardware of any suitable type (e.g., desktop, laptop, notebook, tablets, cellular phones, etc.). In one embodiment, the microcontroller may be the ARM Cortex M3 from ST Microelectronics (STM32F103VGT), though the invention is not so limited.

Figure 21:
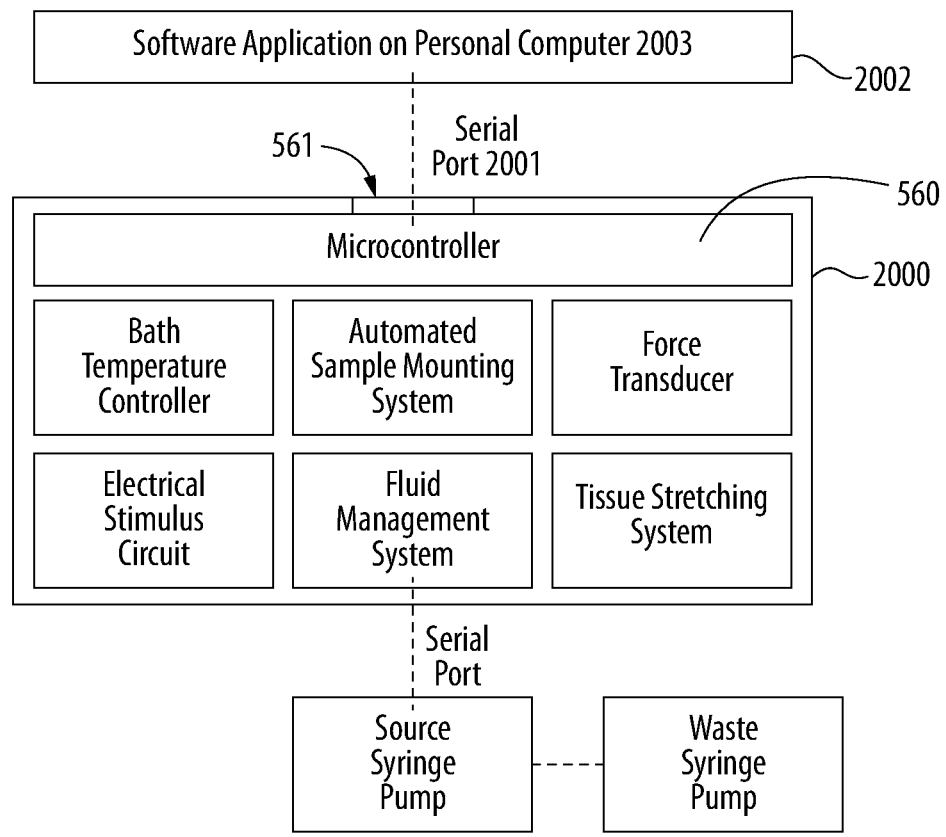
FIG. 21 depicts the connectivity between the instrument, software location on a personal computer, and syringe pumps.
Figure 22:
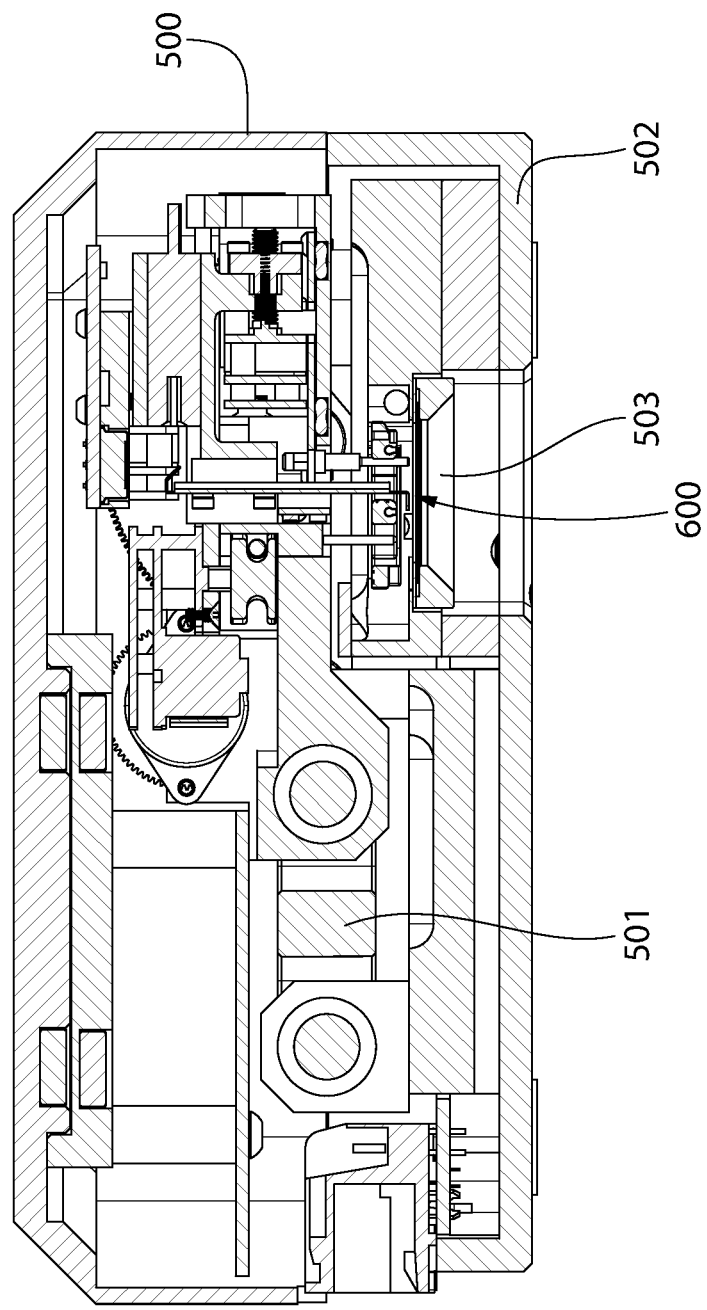
FIG. 22 depicts a cross sectioned side view of the biomechanical testing system in a closed position. This view portrays positioning of certain components within the instrument.
Figure 23:
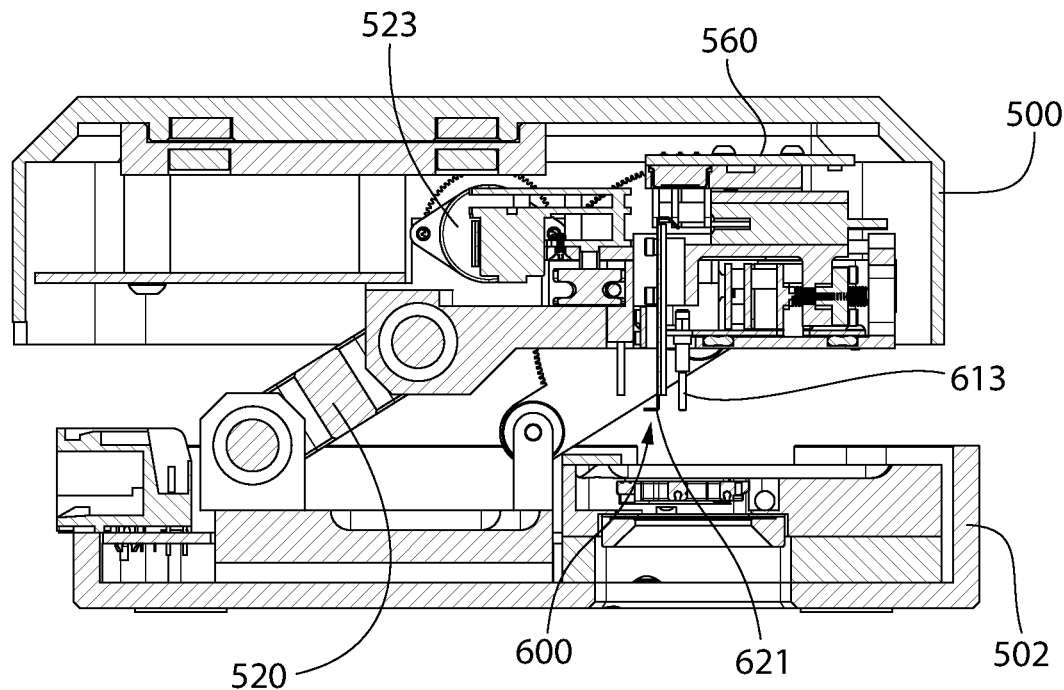
FIG. 23 depicts a cross sectioned left side view of the biomechanical testing system in an open position. This view portrays positioning of certain components within the instrument.

As shown in FIG. 21, the programmable microcontroller 560 may be communicably and operably coupled to an external processor-based personal electronic device 2003 (e.g. personal desktop/laptop computer, tablet, smart phone, etc.) via a communication interface or module 561 configured for wired and/or wireless two-way communications. The communication module 561 comprises a serial communication port 2001 as shown thereby providing an input/output interface which is configured to enable two-way communications between the external personal electronic device 2300 and the microcontroller 560 and tissue testing system of the testing instrument 2000. The communication module 561 may further be configured to enable the programmable microcontroller 560 to communicate via wireless or wired communication protocols with additional remote electronic devices directly and/or over a wide area network.

Reference is generally made in the discussion which follows to FIGS. 6A-10 and 21-35 which show the testing instrument 2000 and various components thereof.

Cassette Interface

Referring to FIGS. 6A-10 and 22-34, the exemplified tissue testing instrument 2000 includes a testing cassette interface 600 including various testing components and devices which interact with and measure various properties of the tissue specimen on tissue scaffold 303 of the cassette 300. The testing cassette interface components generally comprises an electrode 613 for electrically testing the tissue specimen, force transducer cantilever 620 configured to interact with the cassette 300 shown in FIGS. 3A-C, and a support frame 623 attached to and supporting the cantilever 620 from the upper housing 500.

The cassette 300 with tissue specimen grown on tissue scaffold 303 may be loaded into receptacle 506 of the bath area or block 503, found on the lower housing 502, which has corresponding mounting features. The bath block 503 may contain a physiological buffer such as a sterile liquid or fluid (e.g. buffered saline solution) which helps maintain a constant pH. In some embodiments, the sterile fluid may be pumped in a fluid exchange closed flow loop through a fluid exchange port 514 in the lower housing to receptacle 506, as further described herein in additional detail. This buffer could be used to maintain the viability and function of the tissue specimen held in the cassette 300 while positioned in the bath block 503 for testing. In some embodiments, the bath block 503 is interchangeable and could be specialized in configuration to support a variety of tissue types.

Sensors

In certain embodiments, the bath block 503 contains one or more sensors. The sensors may be positioned at any part of the bath block 503 or other parts of testing instrument 2000 either in the upper or lower housings 500, 502 depending on the purpose and type of sensing required. These sensors could be used for example and may include, but are not limited to, position and/or proximity sensors monitoring the position of the cassette interface components 600 described above during operation to confirm actual movement of the components, fluid lever sensors 800 monitoring the level of the fluid in the receptacle 506, and temperature sensor 645 monitoring the temperature of the sterile fluid. In certain embodiments, at least a level sensor 800 and temperature sensor 645 may be used as further described below.

The sensor data is transmitted by the various sensors to microcontroller 560 of the tissue testing instrument control system. The biomedical tissue testing instrument 2000 (microcontroller 560) may in turn relay the sensor data to one or more of an external computing devices (e.g. personal computer, tablet, smart phone, etc.), a data storage device, a data aggregation service in the cloud, or an internet based remote data aggregation service.

Fluid Heating System

Figure 35:
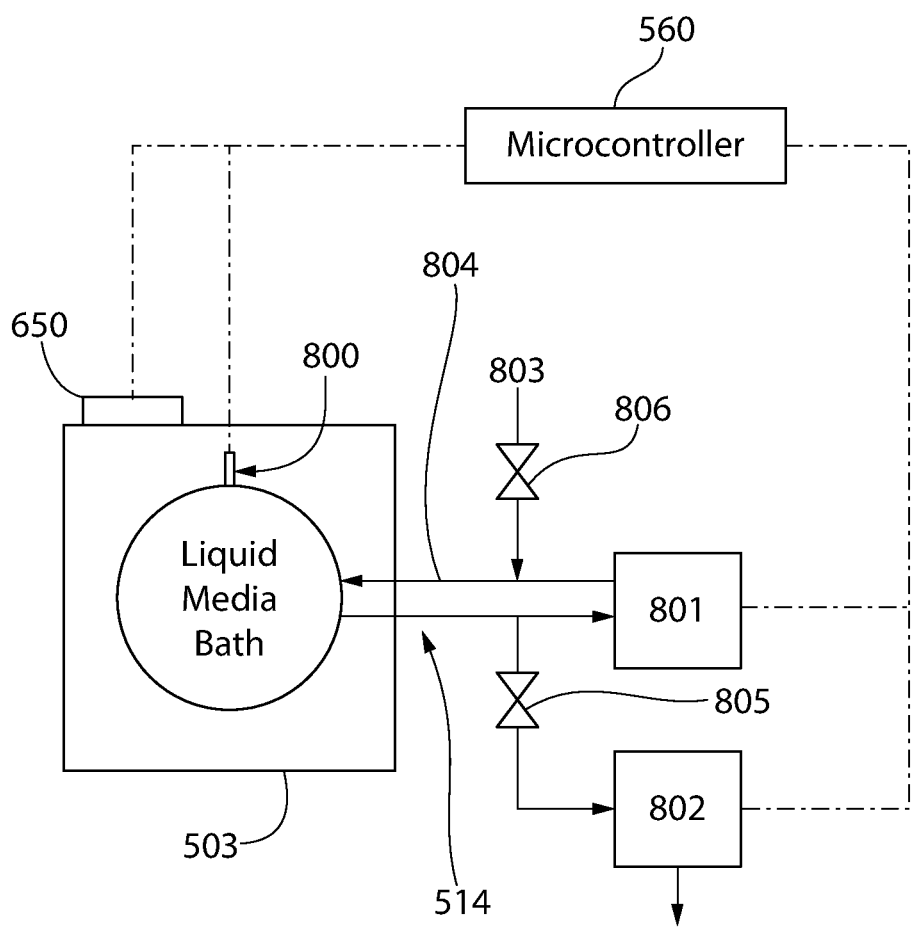
FIG. 35 is a system flow schematic of the microcontroller, bath, liquid/fluid pumps and sensors which form a level control system.

In certain embodiments with reference to FIG. 35, the bath block 503 may further include a heater 650 which heats the block, and in turn the sterile buffer fluid in the receptacle 506 which holds the cassette 300 with tissue specimen for testing. The heater 650 may be operably linked to and controlled by the microcontroller 560, which is operable to heat the bath block to maintain a preprogrammed setpoint temperature of the fluid when contained in the bath block receptacle. Maintaining the proper temperature of the fluid is important for preserving the viability of the tissue specimen.

The bath block 503 may be made of a suitable preferably biologically inert and thermally conductive metal amenable to heating. In one embodiment, the heater 650 may be an electrical resistance heating element; however, other types of heaters may be used (e.g. It a thermoelectric heater to maintain temperature control in a broad range of environmental temperatures).

The heating system may further comprise temperature sensor 645 operably linked to the microcontroller 560. The microcontroller may be configured to sense a temperature indicative of a temperature of the fluid in the bath block (e.g.

receptacle 506) and regulate the temperature of the fluid via controlling the heat output from the bath block heater 650. For example, the microcontroller compared the real-time actual temperature of the fluid measured by the tempt sensor 645, compares the actual temperature to the preprogrammed setpoint temperature, and increase or decrease the heat output from heater 650 as needed to achieve the setpoint temperature. In some embodiments, the setpoint temperature may be a temperature range which represents a range of acceptable temperatures of the fluid necessary to preserve the viability of the tissue specimen.

Fluid Level Control System

Referring to FIGS. 21 and 35, the tissue testing system embodied in testing instrument 2000 may further comprise a fluid level management or control system comprising a circulating pump 801 fluidly coupled to the bath block 503; more specifically cassette receptacle 506 in the lower housing 502. The fluid level control system may be configured to circulate the sterile fluid through the receptacle in a closed flow loop 804 (See, for example, FIG. 35). The lower housing may further comprise a pair of fluid exchanged ports 514 (e.g. inlet and outlet ports) fluidly coupled to the closed flow loop and receptacle for circulating the fluid. The fluid level control system may further comprise a level sensor 800 operable to measure a surface level of the fluid in the receptacle. The level sensor 800 and circulating pump 801 may be operably linked to the microcontroller 560 which is configured via programming to regulate the surface level of fluid in the receptacle to maintain a preprogrammed level setpoint. The level sensor 800 may be a filtered infrared reflectance sensor positioned above the surface level of fluid in the receptacle in one non-limiting embodiment. In certain embodiments, the system may further comprise a waste pump 802 which may be under the control of microcontroller 560 for removing excess fluid from the closed flow loop 804, and an injection port 803 for adding fluid to the closed flow loop. The injection port may be used to introduce various chemicals or drugs to the sterile fluid for testing the response of the tissue specimen thereto. The injection port access to the closed flow loop may be controlled by an injection valve 806 operably linked to microcontroller 560. In operation when a high fluid level in the batch block cassette receptacle 506 is detected by microcontroller 560, the microcontroller will open waste valve 805 and operate the waste pump 802 to remove excess fluid from the closed flow loop until the preprogrammed level setpoint is reached. In certain embodiments, the circulating and waste pumps 801, 802 may be a syringe pump; however, any other suitable type pumps for this application may be used.

The system may further comprise a force transducer cantilever 620 mounted to the upper housing 500 and operably linked to the microcontroller 560 of the testing instrument 2000. The force transducer cantilever 620 may be insertable into the cassette 300 to engage the floating clip 310 of the tissue scaffold assembly and operable to measure a tensile force of the tissue specimen when stretched. The force transducer cantilever 620 may be linearly movable and configured to stretch the tissue specimen for obtaining the tensile force measurement. In preferred embodiments, the force transducer cantilever 620 is configured to engage and linearly translate the floating clip 310 to stretch the tissue specimen. In certain embodiments, the floating clip 310 is supported between a pair of resiliently flexible cantilevered spring arms 323 and 325 disposed on the cassette 300, and moving the spreader pins 631 apart displaces the spring arms 323 and 325 to uncouple and release the floating clip 310 from the cassette 300 such that the force transducer cantilever 620 can linearly translate the floating clip 310. The spring arms 323 and 325 are movable between an inward collapsed configuration which retains the floating clip 310 to the cassette and an outward spread apart configuration which releases the floating clip 310.

Figure 7:
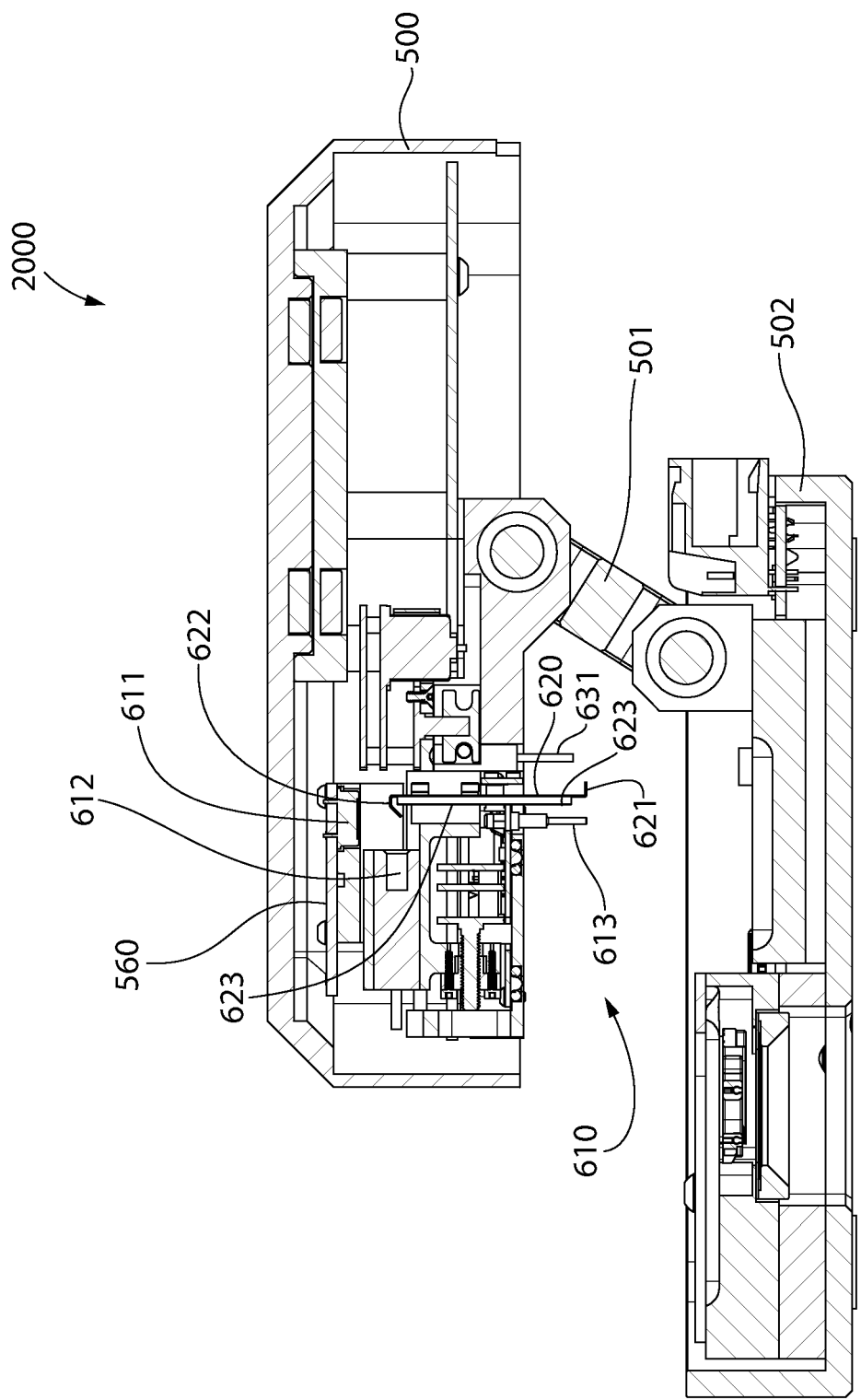
FIG. 7 depicts a side view layout of a biomechanical testing system according to one embodiment.
Figure 27:
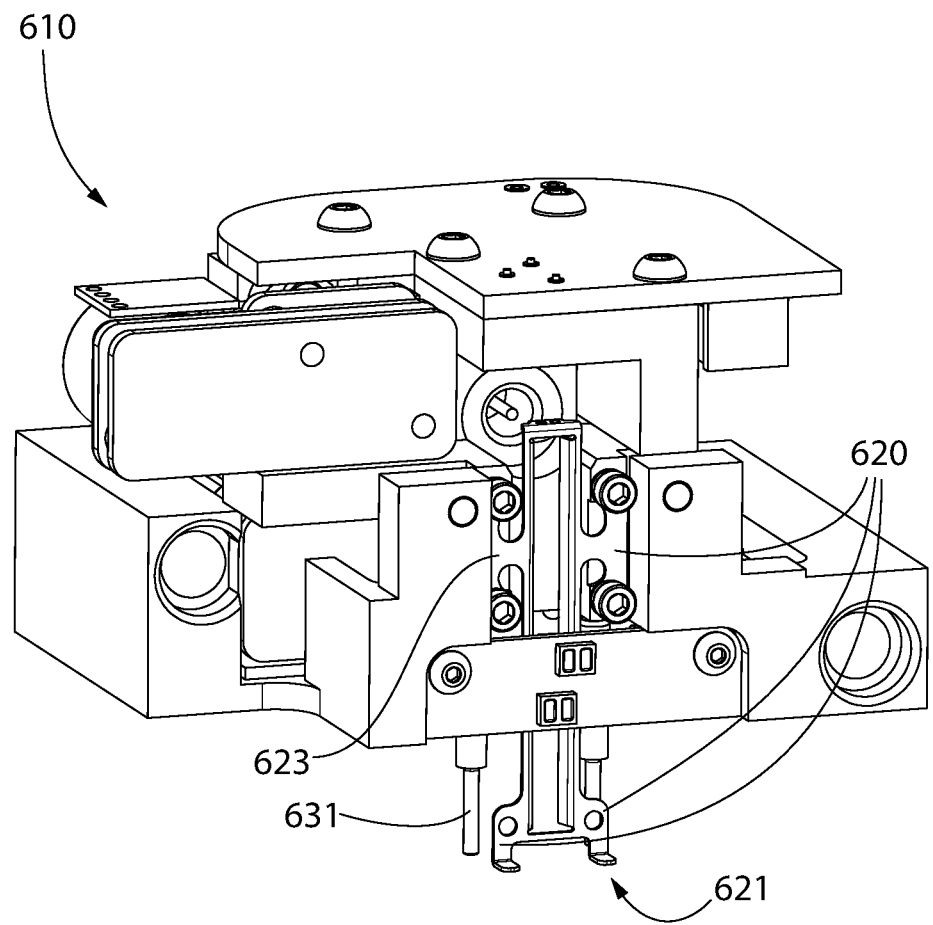
FIG. 27 depicts a side view of the force transducer carrier block component.
Figure 28A:
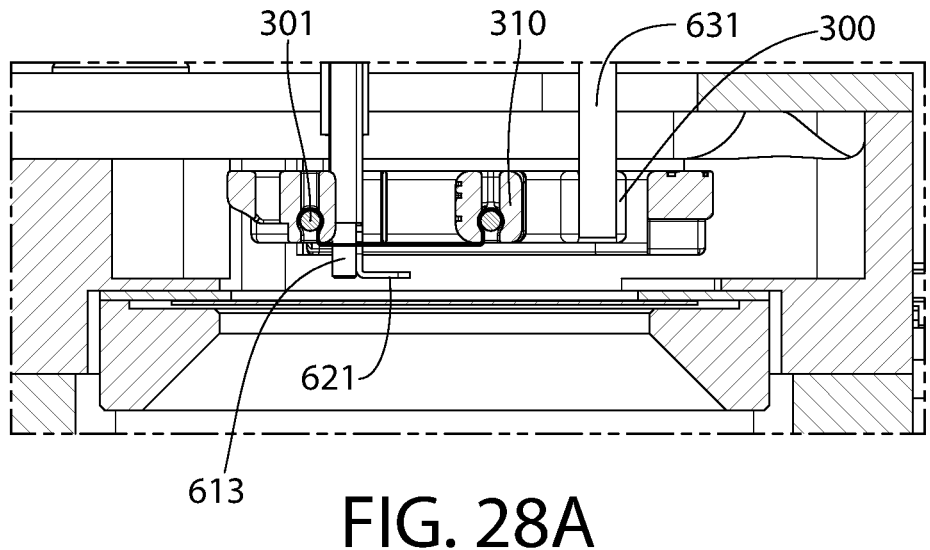
FIGS. 28A-28C depict the interface between the cassette, detachable clip and cantilever. The cantilever is shown traversing across the cassette.
Figure 28B:
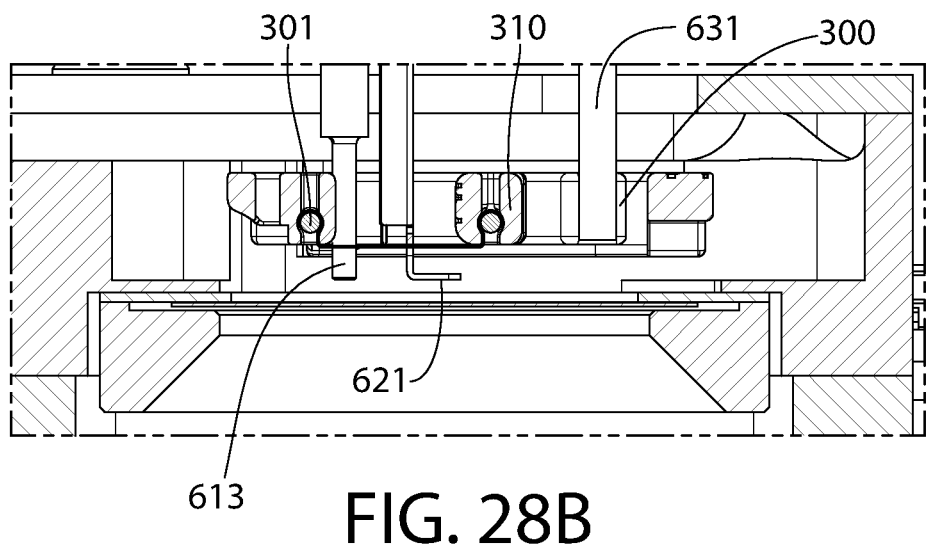
Figure 28C:
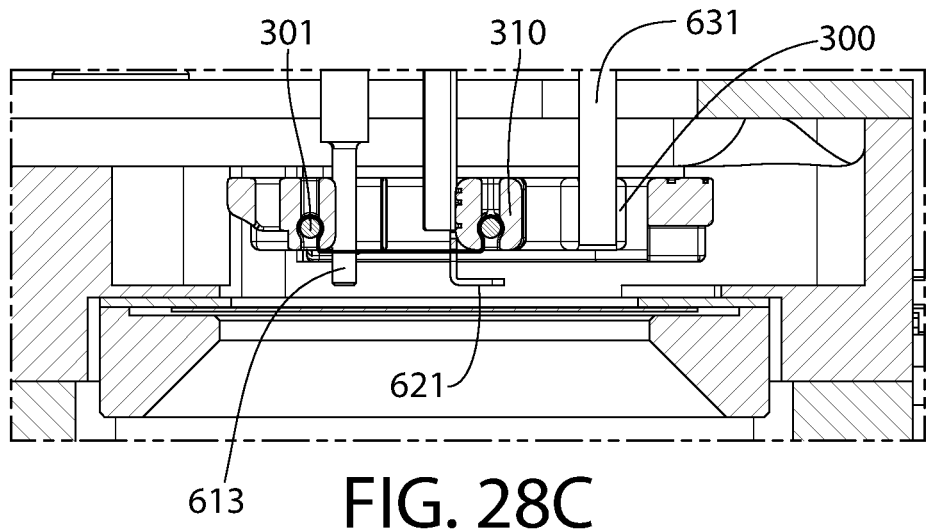

Referring specifically to FIGS. 7 and 27, the upper housing 500 contains force transducer cantilever 620 that is attached to movable carriage frame 623 and the two spreader pins 631 previously described herein. These components in turn are each mounted onto a force transducer carrier block 610 which movably supports the spreader pins 631 and the force transducer 614. The force transducer cantilever 620 mounted to the upper housing 500 may be operably linked to the microcontroller. The force transducer cantilever 620 is insertable into the cassette 300 and operable to measure a tensile force of the tissue specimen when stretched. More specifically, the cantilever 620 in one embodiment as shown may have a bifurcated configuration comprising a pair of spaced apart and downwardly extending L-shaped vertical legs configured and arranged to engage the floating clip on each opposite side of the tissue scaffold 303 to avoid damage thereto. The terminal end of each leg may include a horizontally extending prong 621 insertable beneath and supporting the floating clip 310 of the tissue scaffold assembly somewhat tantamount to the prongs on a forklift. When engaged, the floating clip rests against the L-shaped cantilever. The force transducer cantilever 620 may be linearly movable and configured to stretch the tissue specimen for obtaining the tensile force measurement. In some preferred embodiments, the force transducer cantilever 620 is configured to engage and linearly translate the floating clip to stretch the tissue specimen. In certain embodiments, the floating clip 310 is supported between a pair of resiliently flexible cantilevered spring arms 323 and 325 disposed on the cassette 300, and moving the spreader pins 631 apart displaces the spring arms 323 and 325 to uncouple and release the floating clip 310 from the cassette 300 such that the force transducer cantilever 620 can linearly translate the floating clip 310. The spring arms 323 and 325 are movable between an inward collapsed configuration which retains the floating clip 310 to the cassette and an outward spread apart configuration which releases the floating clip 310.

Force Transducer Measurement System for Tensile/Contractive Force Measurement

Figure 8:
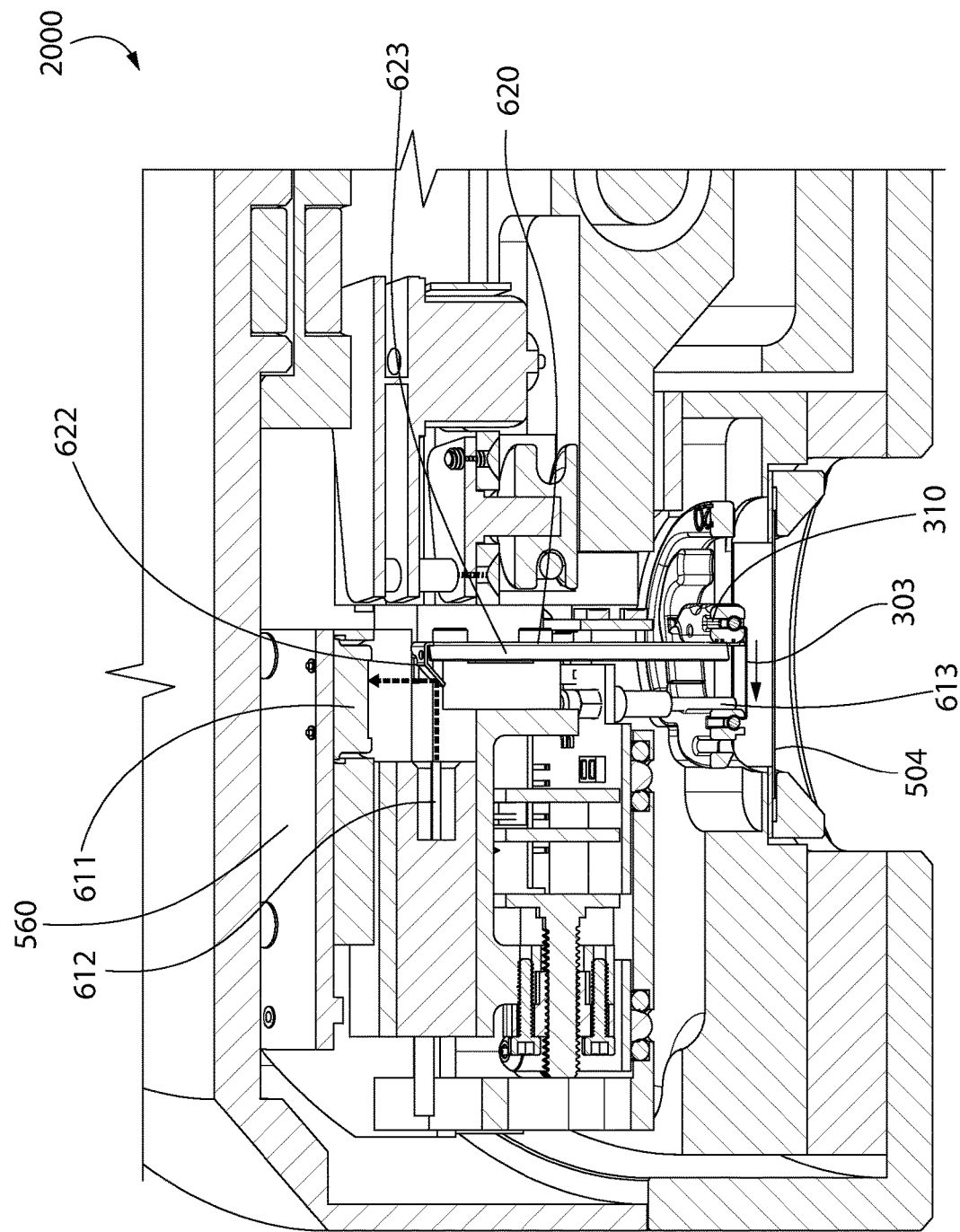
FIG. 8 depicts a force transducer carrier area and a cassette interface area according to one embodiment.
Figure 9:
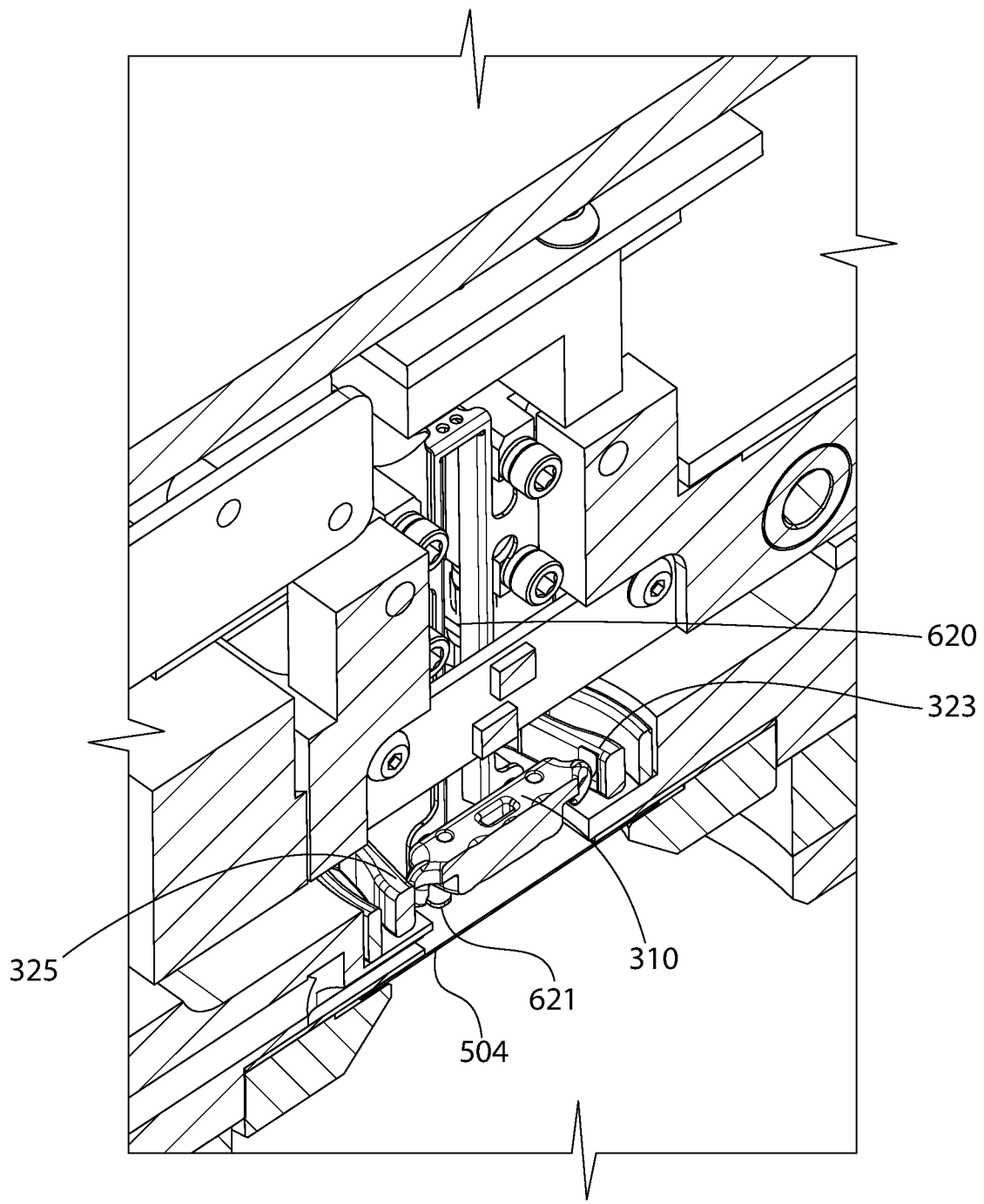
FIG. 9 depicts the interaction between the detachable and cantilever according to one embodiment.

The force transducer cantilever force measurement system is operable to both measure tensile force and contraction of the tissue specimen grown on tissue scaffold 303 when the floating clip 310 is detached from the cassette 300 and fully supported by the force transducer cantilever 620. As illustrated in FIG. 8, the force transducer cantilever assembly includes a laser 612 arranged to direct and emit a laser beam 616 at a top reflective surface or mirrored end (i.e. reflector 622 in FIG. 8) of the force transducer cantilever carriage frame 623 which in turn reflects the laser onto a commercially-available bi-cell photosensor 611 (see laser beam directional arrow). A photodiode may be used in some embodiments. In certain embodiments, a quad cell, single cell photo sensitive device, or other sensor types may be used.

In operation, the laser 612 is aligned so that, under no-load conditions on the cantilever arm 620 when the tissue scaffold/specimen is not stretched by the force transducer cantilever 620 or contracted via electrical stimulation caused by energizing electrode 613, the laser spot reflected from the reflective or mirrored surface of the cantilever (e.g. reflector 622, FIG. 8) strikes the gap between the photosensor cells of the bi-cell photosensor 611. This is the baseline/steady-state cantilever condition which reflects laser light at a 90-degree angle from the laser directly to the gap in the bi-cell photosensor component. Then, the tissue stretches or contracts along direction of tissue force when either stretched by translating force transducer cantilever 620 or applying electrical stimulation to the tissue specimen. As the tissue specimen stretches or contracts, the cantilever bends about its point of rotation on carriage frame 623. The bent cantilever now deflects the laser beam at some other angle resulting in a shifted laser spot across the bi-cell photosensor 611. The shifted spot correlates to different analog voltage outputs of the two sensor cells of the photosensor when compared to the baseline. This analog voltage output is amplified and differentiated through a voltage follower differential amplifier circuit before being converted to a digital signal and output from the testing instrument to the user's personal electronic device. Periodically, sensor may require realignment through shifting the cantilever and photodiode position to recreate the baseline reading of the laser spot in the gap between the sensor cells of the bi-cell photosensor 611.

In other embodiments, alternative mechanisms of sensing tissue reaction or contraction may be used including but not limited to, a motion detection camera, a physical sensor attached to the end of the cantilever 620, or a device the produces or senses other types of emissions. The cassette interface 600 may include at least one electrode pair 613 and one sensor, such as a bi-cell photosensor 611. The electrode pair 613 is used to electrically stimulate the excitable tissue, which can cause the tissue to react or contract.

The instrument 2000 can measure any longitudinal movement of the detached floating clip 310 caused by stretching the tissue scaffold and specimen thereon longitudinally (i.e. along the length of the tissue scaffold 303 between clips 310, 315) by using the bi-cell photosensor 611 to measure the change in the angle of the laser beam 616, produced by the laser 612, reflecting off of the upper reflective or mirrored end (e.g. reflector 622) of the cantilever 622. In addition, the cantilever 620 can be used to manipulate the tissue sample 303 to a specified length. In some embodiments, the force transducer carrier block 610 is interchangeable to allow different sensors and manipulators to be placed within the instrument 2000 for different types of testing. In some embodiments, the cantilever 620 is used to support the detached clip 310 as previously described herein. As demonstrated in FIG. 9, the cantilever 620 can entirely support the detached clip 310 when detached from cassette 300 by going around the scaffold 303 and under the sides of the clip 311, 312 to prevent damage to the tissue specimen on the scaffold.

Figure 10:
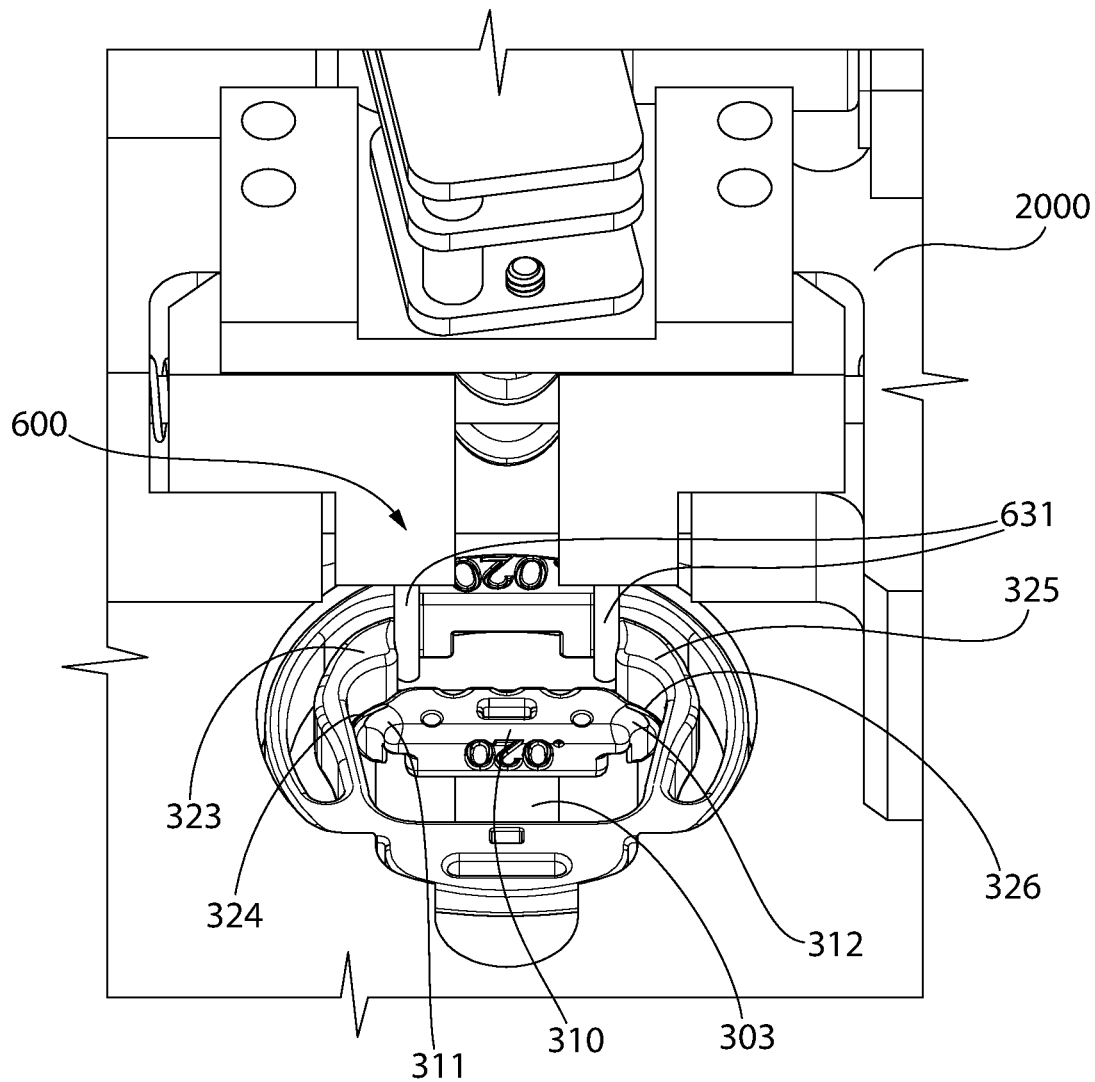
FIG. 10 depicts an example of how the detachable is disengaged from the cassette.
Figure 29A:
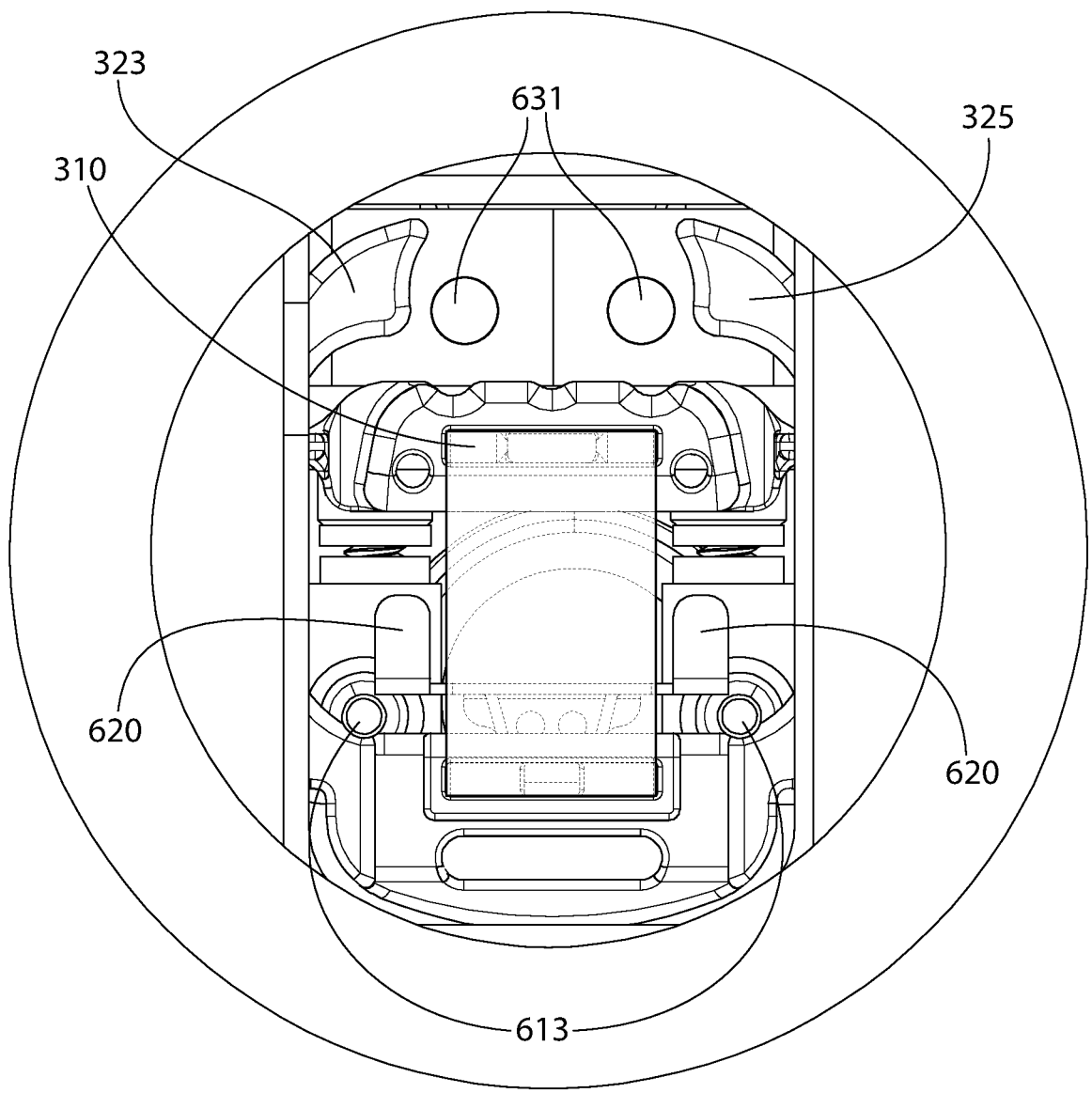
FIG. 29A depicts a bottom view through the glass window of the instrument. In this depiction, the cassette is resting within the bath block and the cantilever is not engaged to the clip.
Figure 29B:
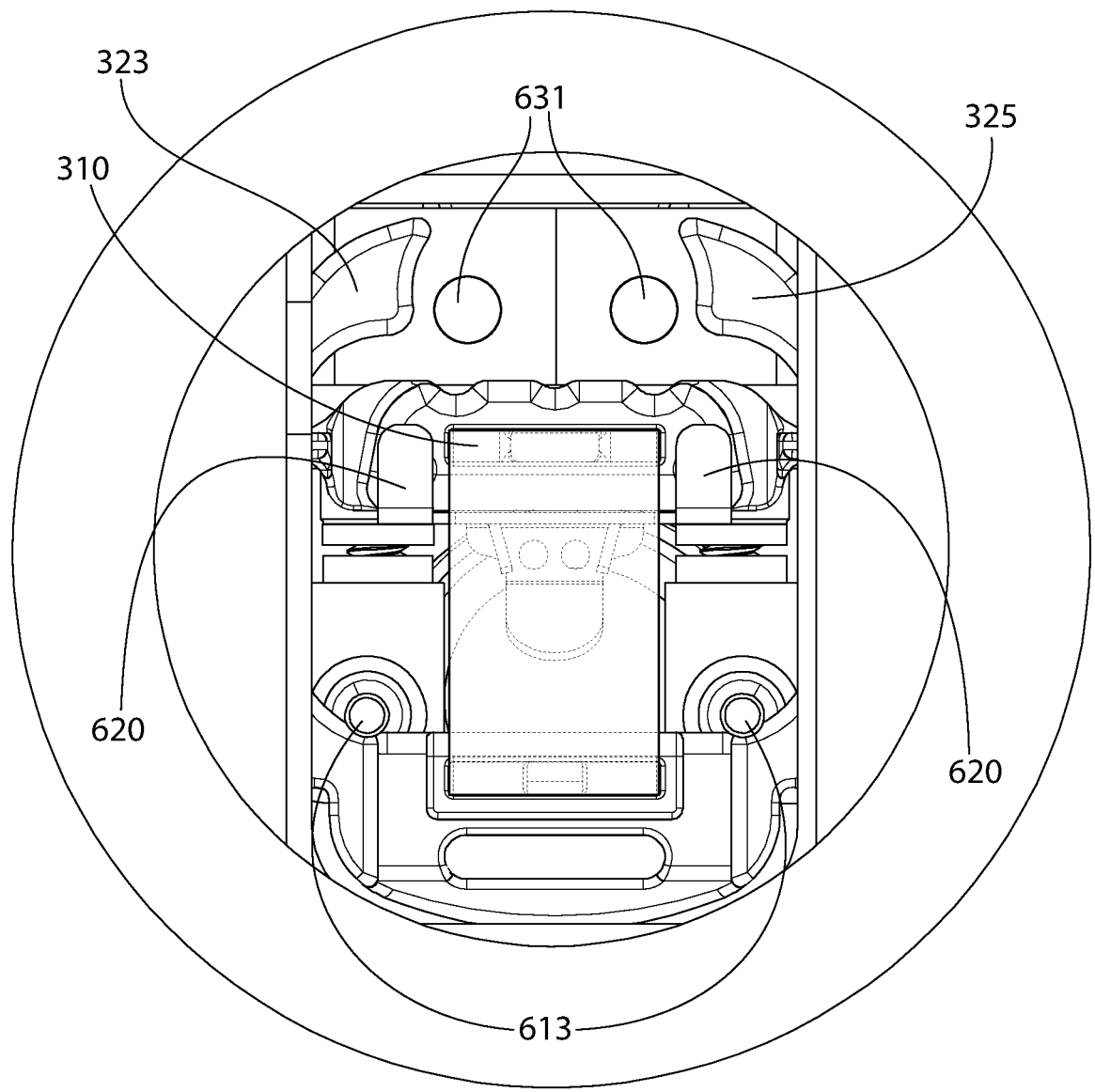
FIG. 29B depicts a bottom view through the glass window of the instrument. In this depiction, the clip is engaged, or grabbed, with the cantilever.

FIGS. 10, 30A and 30B depict the two spreader pins 631 of the instrument 2000 that are used to disengage the detachable floating clip 310 from the cassette 300. In the exemplified embodiment of FIG. 10, the two pins 631 push outwards and remove the geometric lock formed between the flexible spring arms 623, 625 of the cassette and the floating 310. In some embodiments, the cassette interface contains at least one spring arm. Further, the pins 631 could be used to reengage the detachable 310 to the cassette 300. FIGS. 30A and 30B show shows a bottom view through the glass window 504 of the instrument 2000. The spreader pins 631 push the first and second flexible spring arms (323 and 325) outward, which releases the geometric fit which keeps the detachable clip 310 into place. This can take place after the force transducer cantilever 620 grabs the detachable clip 310 (See FIGS. 29A-29B). FIG. 29A shows a bottom view through the glass window 504 of the instrument 2000. In this depiction, the cassette 300 is resting within the bath block 503 and the cantilever 620 is not engaged to the detachable clip 310. FIG. 29B depicts a bottom view through the glass window 504 of the instrument 2000. In this depiction, the clip is engaged with and fully supported by the cantilever 620. At this point, the detachable clip 310 may be released from the cassette 300 without any potential dropping or damage to the tissue scaffold 303 and tissue specimen thereon.

In some embodiments, the tissue scaffold 303 can be recovered for additional incubation and further testing. This would allow a single tissue source to be used repeatedly. If the tissue was harvested from a patient such as through a biopsy, this would reduce the amount of pain and suffering for a patient. In some embodiments, the instrument 2000 has a secondary attachment to seed the scaffold 303 in the cassette 300. In a further embodiment, the seeding process is automated. In some embodiments, the instrument 2000 has an internal incubator or a stand-alone device that could be automated to incubate and grow the cells on the scaffold 303 or an array of scaffolds.

Fluid Exchange Functionality

During the course of physiological testing, having the capability to exchange the fluid of the tissue bath allows for greater variability in analysis of tissue response to environmental conditions. For example, it may be desirable to exchange solution in order to expose the tissue to different substances (e.g. drug compounds) and change compound concentrations during testing.

In certain embodiments, the biomechanical tissue testing system provides fresh physiological buffer solutions to the tissue and carries away metabolic byproducts that build up during testing. The biomechanical testing system may be equipped to enable precise fluid management by virtue of a fluid level control system previously described herein. This system may comprise inflow/inlet and outflow/outlet tubing fittings 514 (See FIG. 6A) that provide fluid access to the cassette receptacle 506 in the sample bath block 503, a fluid level electronic sensing board, and two pumps, which may be syringe pumps such as a source or circulating syringe pump 801 and a waste syringe pump 802, which may be connected via RS-232 digital communication protocol to the microcontroller 560 (See for example FIGS. 21 and 35). A feedback control algorithm uses the fluid level measurement value to either add or remove fluid until the desired fluid level is attained. A continuous superfusion control program may also be implemented that involves infusion and withdrawal of fluid from the bath at a constant rate, with feedback from the fluid level sensor used to reconcile small differences in inflow/outflow that can cause unwanted changes in fluid level over time. The fluid level may be sensed by an active, filtered infrared reflectance sensor positioned above the fluid in the bath. The reflectance value returned by the sensor results in a highly accurate short-range measurement of the position of the fluid surface.

Biomechanical/Physiological Testing System Setup

The biomechanical testing system is designed to contain all required software, firmware, and hardware required to conduct physiological tissue testing in a compact, integrated form (See, for example, FIGS. 28A through 33B). It may be comprised of the previously described equipment an devices such as biomechanical testing machine or instrument 2000, syringes and tubing, OEM syringe pumps, etc., and the personal electronic device 2003 such as a computer running a custom software application and communicating with microcontroller 560 to coordinate the testing procedures and data collection. Together, these elements enable the user to perform complex physiological tissue performance testing in an automated fashion, with a high degree of efficiency and reproducibility.

FIG. 21 shows the arrangement of software application (e.g. program instructions/control logic) which may comprise firmware stored on and executed by microcontroller 560, and other system controllers and systems included within the biomedical instrument 2000 package. The software application 2002 is used for example without limitation to control the instrument's settings, program measurement procedures, log measurement data collected through the instrument, and analyze/visualize data. It is connected to the instrument via serial communication port 2001.

The tissue testing system comprises the digital microcontroller 560 of testing instrument 2000 that operates the firmware to coordinate and run at least several functions: (1) serial communications with the host PC/software application, (2) force transducer operation and data collection, (3) control of the sample bath temperature, (4) management of the sample bath fluid level and solution flow, including digital communication with attached syringe pumps via serial port, (5) control of the sample bath's electrical stimulus circuit, (6) control of the automatic sample mounting system, and (7) control of the sample tissue length. The instrument 2000 may also contain other components such as, but not limited to, electrical circuits, stepper motors, actuator/drive mechanisms for the various testing components, fluid level sensor 800, temperature sensor 645, and others where each component may be managed and controlled by the microcontroller.

Method of Use

In some embodiments, the present invention can be used to diagnose organ pathologies and certain embodiments can be used to create a treatment plan. The uses of the present invention can include, but are not limited to, analyzing and/or assessing the effectiveness of drugs, assessing the interactions between the tissue sample and an added drug, genotyping, and identifying biomarkers. All methods of analysis could be done through an automated process.

In some embodiments, the present invention can analyze various tissue sources including but not limited to harvested patient tissue, commercially grown samples, or 3D printed tissue. Tissue types include but are not limited to, cardiac tissue, skeletal tissue, nervous tissue, and connective tissue. In some embodiments, the tissue source is obtained from a biopsy. The biopsy method could be done though any standard method. In some embodiments, heart cells are obtained through a minimally invasive biopsy.

Figure 11:
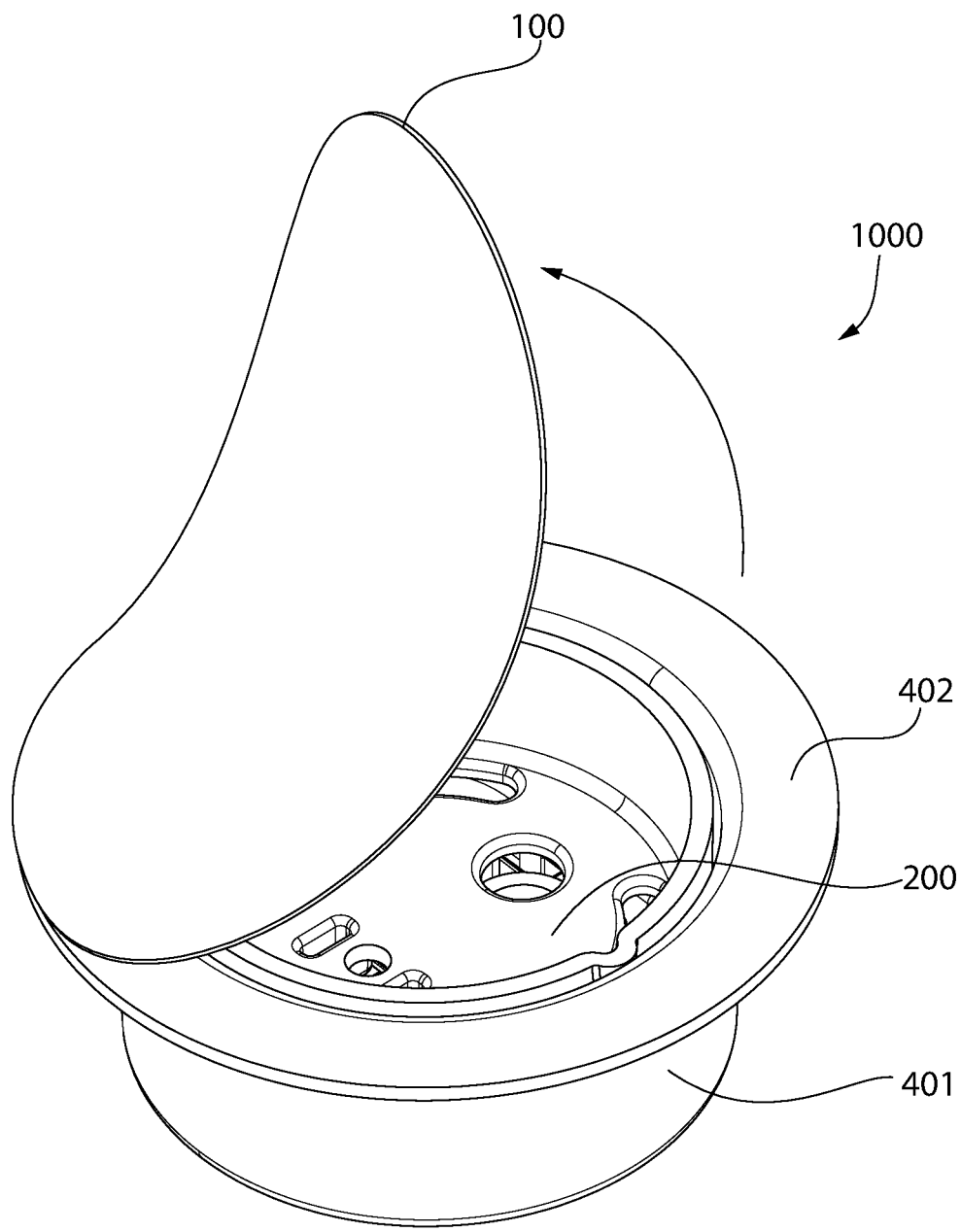

A possible method for using the bioreactor device of the present invention is illustrated in FIGS. 11 through 16. As shown in FIG. 11, the lid 100 of the bioreactor device 1000 is first removed. Referring to FIGS. 12A and 12B, a pipette tip is inserted through the larger media or aspiration hole 215 in mask 200, into the media exchange region 420, and aspirates/extracts 1122 the sterile liquid/fluid 1120 as further depicted in FIGS. 13A and 13B. Notably, the liquid 1120 found in the seeding trough 410, however, remains intact due to its greater depth and prevents the scaffold 303 from decreasing in biological function by remaining at least partially immersed in the sterile fluid (shown in FIG. 13B). The cassette frame 320 is configured to prevent access to the seeding trough 410 by the pipette.

Figure 14A:
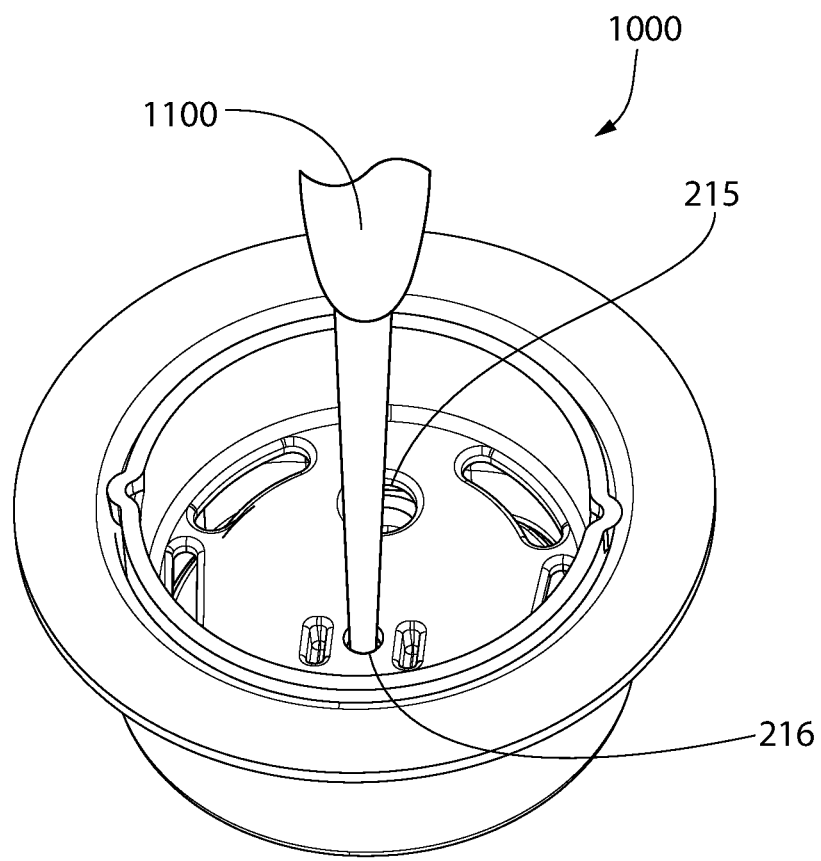
FIG. 14A depicts a top perspective view of the bioreactor device according to one embodiment having a pipette tip inserted into the seeding hole.
Figure 14B:
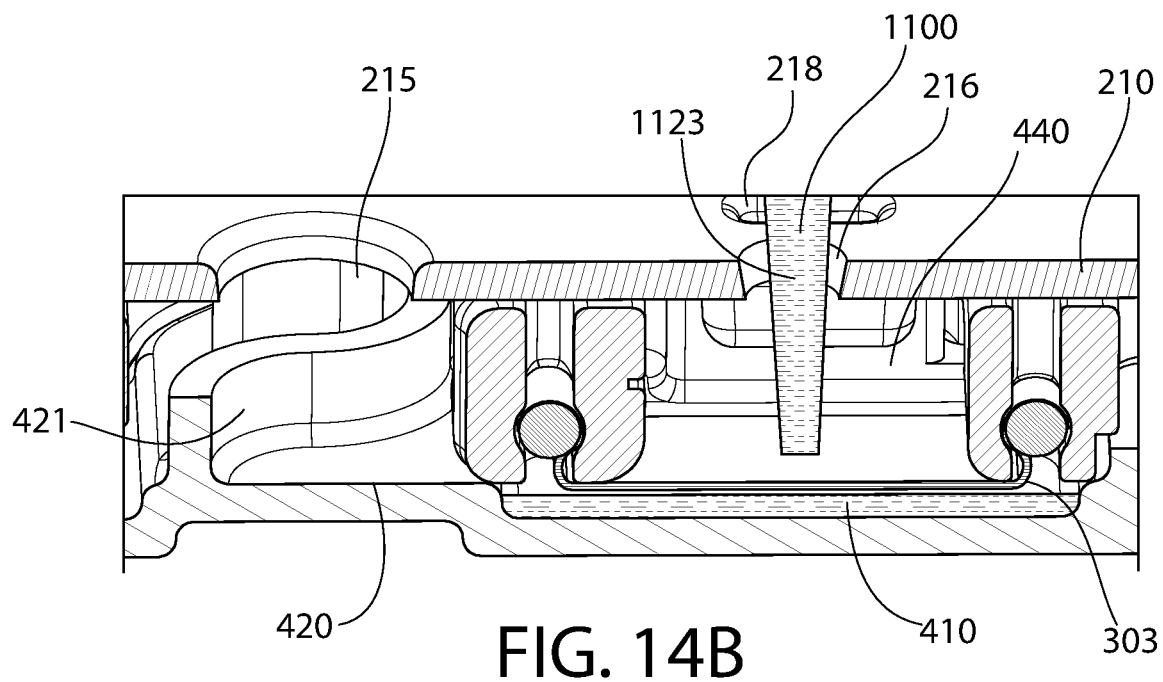
FIG. 14B depicts an exploded side perspective view of the bioreactor device according to one embodiment having a pipette tip inserted into the seeding hole and containing seeding liquid.
Figure 14C:
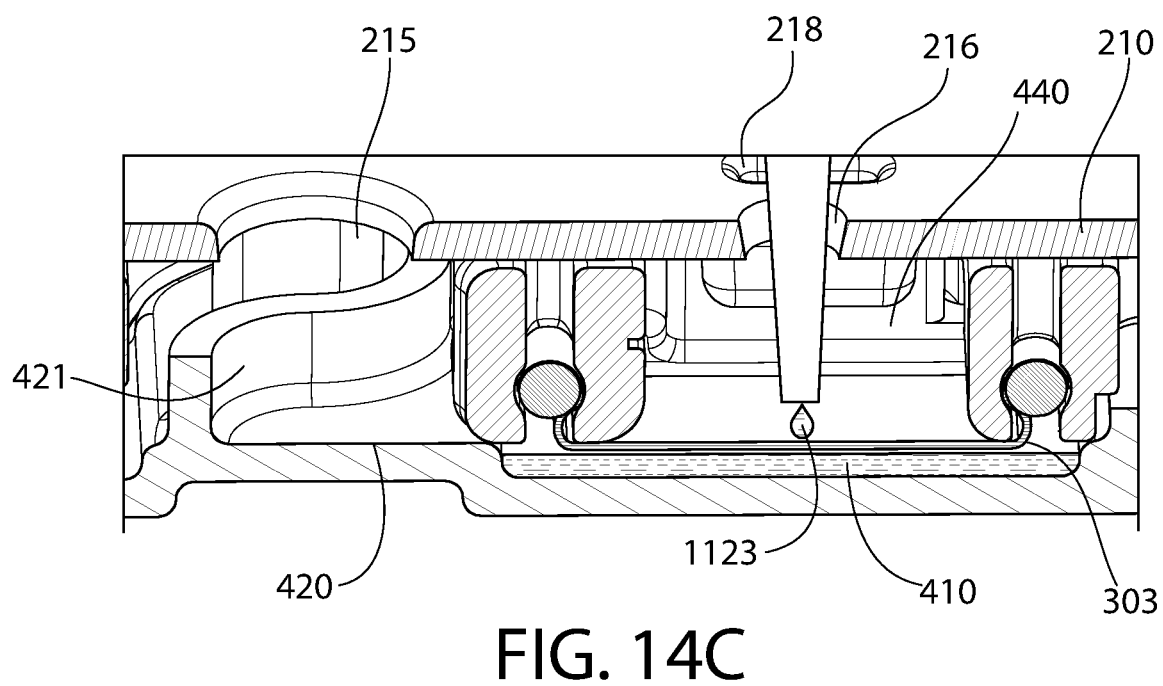
FIG. 14C depicts an exploded side perspective view of the bioreactor device according to one embodiment having a pipette tip inserted into the seeding hole and dispensing seeding liquid.

Following to FIGS. 14A and 14B, next a pipette with seeding liquid containing cells 1123 is inserted into the smaller seeding hole 216 of mask 200 to drop the cells onto the tissue scaffold 303 which is directly below. As previously stated, the smaller seeding hole 216 could be sized to hold a specific standard pipette size at a set height over the scaffold 303 for an optimized seeding region. Because the tip of the pipette is slightly frustoconical in shape as seen, the diameter of the seeding hole 216 may be selected to engage the tip at a point which prevent the terminal end of the tip from contacting the tissue scaffold 303. In this exemplified embodiment, the bioreactor device 1000, now without the lid, may be incubated for about 24 hours (or shorter/longer as required) to allow cells to attach to the scaffold 303.

Figure 15:
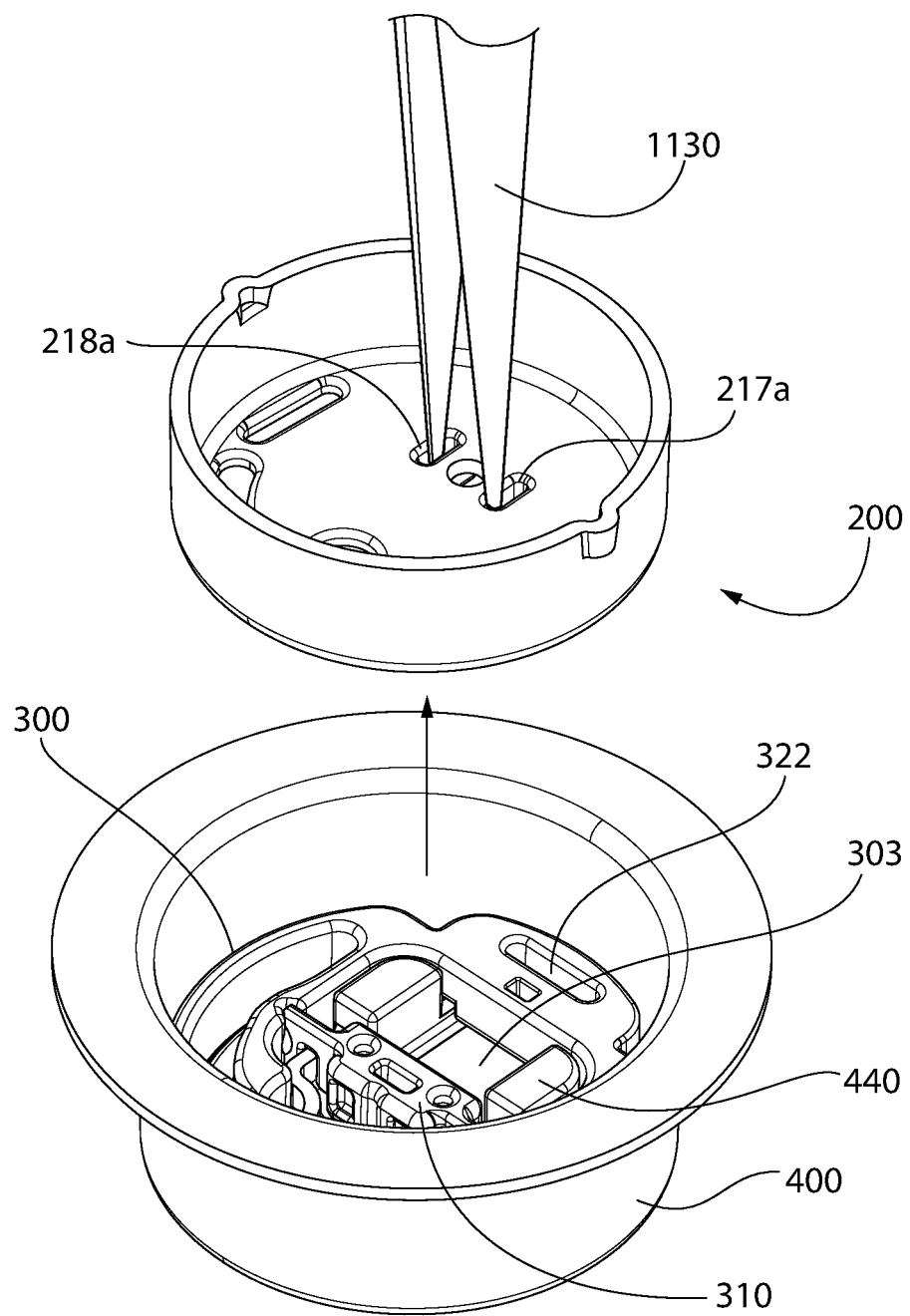
Figure 16:
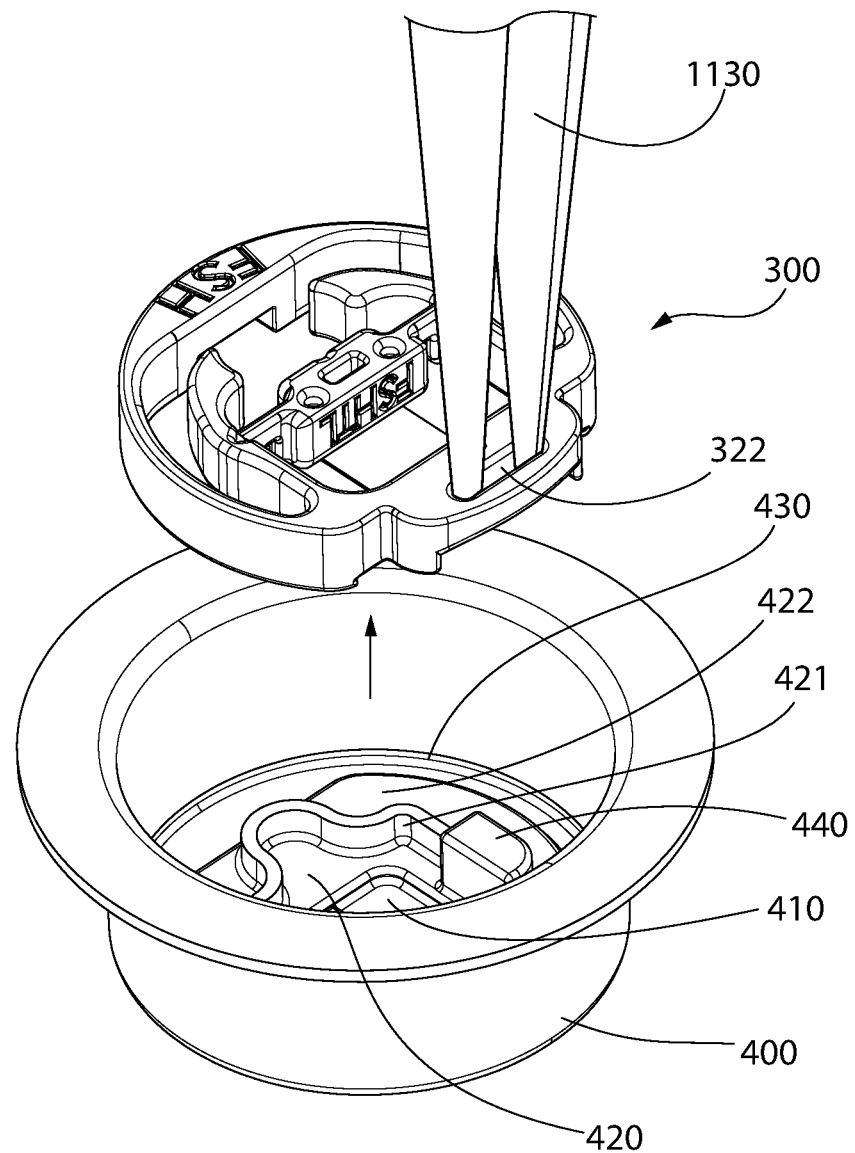
Figure 17:
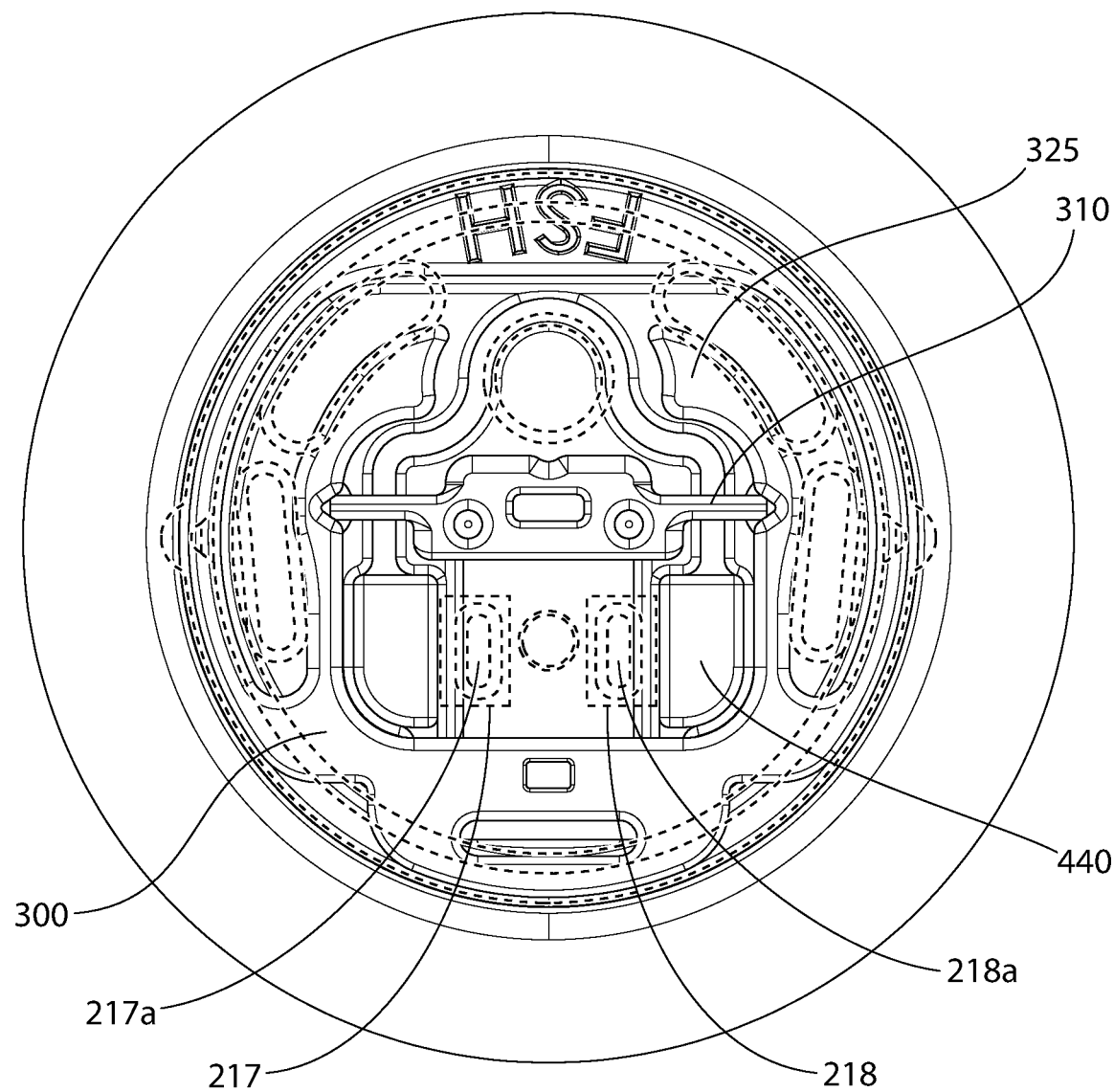
FIG. 17 depicts a top down view of an embodiment of a bioreactor device. In this view, cassette is contained within the cup.

After allowing cells to integrate onto the scaffold 303, the mask 200 may be removed from the bioreactor device 1000. Referring to FIG. 15, forceps 1130 are inserted into the two open recesses 217a, 218a formed by protrusions 217, 218 on either side of the seeding hole 216 in the mask. The protrusions 217, 218 are sized to allow the forceps to exert an outward pressure when at an expanded rest position. The mask 200 is then removed from seeding cup 400 revealing the cassette 300 with seeded tissue scaffold 303 below. Referring to FIG. 16, forceps 1130 are inserted into the grasping slot 322 of the cassette 300, which is sized to allow the forceps to exert an outward force when at an expanded rest position. The cassette 300 is removed from the bioreactor device 1000 and can be placed in a standard 12-well plate 700 for further incubation and tissue growth. After the necessary incubation period expires, the cassette 300 can now be analyzed and physiologically tested with the testing instrument 2000 and may be transferred thereto using the same cassette grasping hole 322 and a forceps. The cassette 300 is placed in receptacle 506 in the testing instrument's lower housing 502 which contains the sterile fluid bath. The instrument may then be closed to begin the tissue testing protocols including electrical excitation via electrode 613 to measure contraction of the tissue to an electrical stimulus, and tensile force measurement by stretching the tissue with the force transducer cantilever 620 assembly.

Summary of the Claimed Embodiments

In certain embodiments, a packaged bioreactor device 1000 may comprise: a cup 400 including a bottom, a top, and an internal cavity extending between the bottom and the top; a lid 100 sealing the top of the cup and being removable to access the cavity; a tissue scaffold 303 supported in the cavity; and a mask 200 removably disposed in the cavity above the tissue scaffold 303, the mask 200 including a plurality of through holes (e.g. round media hole 215, seeding hole 216) to access the tissue scaffold 303 and portion of the cavity below the mask. In certain embodiments, the device according may further comprise a sterile fluid disposed in the cavity of cup at least below the mask, the tissue scaffold at least partially immersed in the fluid. In further embodiments, the fluid below the mask is accessible for aspiration through an aspiration hole of the through holes which is laterally offset in position on the mask from the tissue scaffold. In certain embodiments, the through holes include a seeding hole in the mask which is positioned directly above the tissue scaffold for introducing cells to the scaffold through the seeding hole. The seeding hole may be smaller than the aspiration hole. The through holes may include a pair of elongated removal slots configured for grasping with a tweezers to remove the mask from the cup. In certain embodiments, the seedling hole is located between and proximate to the removal slots.

In certain embodiments of the device, the cup has a cylindrical configuration sized to fit in a cell of a standard twelve cell laboratory culture dish or tray. In certain embodiments, the mask may comprise a bottom wall and an upstanding cylindrical sidewall configured to slideably engage a cylindrical sidewall of the cup when the mask is inserted therein. In certain embodiments, the mask includes a pair of laterally projecting retention protrusions which frictionally engage sidewall surfaces of the cup for removably retaining the mask in the cup.

In certain embodiments of the device, the tissue scaffold is supported by a cassette removably disposed in the cavity of the cup below the mask. In certain embodiments, the cassette includes a fixed clip engaging a first end of the tissue scaffold, and a second floating clip engaging a second end of the tissue scaffold, the floating clip detachably coupled to the cassette. In certain embodiments, the floating clip is supported between a pair of resiliently flexible cantilevered spring arms, the spring arms spreadable to disengage and release the floating clip. In certain embodiments, the spring arms are movable between an inward collapsed configuration which retains the floating clip to the cassette and an outward spread apart configuration which releases the floating clip. In certain embodiments, the first and second ends of the tissue scaffold are each fixedly coupled to the fixed and floating clips by a hydrogel locking peg arranged in a light bulb shaped locking slot formed in the clips. In certain embodiments, the locking slots include a narrow throat portion and a diametrically enlarged circular seating portion in which the locking pegs are positioned when the tissue scaffold is locked to the clips. In certain embodiments, the locking pegs are changeable from a shrunken diameter when the pegs are in a dehydrated condition to a larger enlarged diameter when the pegs are hydrated. In certain embodiments, the locking pegs can pass through the throat portion when in the dehydrated condition with the shrunken diameter, but cannot pass through the throat portion when in the hydrated condition with the enlarged diameter. In certain embodiments, the locking pegs are in the hydrated condition when positioned in the circular seating portion of the locking slots.

In certain embodiments of the device, the cassette is configured to hold the tissue scaffold in an inverted suspended manner stretched between each clip in which the tissue scaffold is located below the clips. In further embodiments, the mask includes a pair of downwardly extending first anti-rotation protrusions arranged to engage a mating pair of upwardly extending second anti-rotation protrusions formed on a bottom wall of the cup within the cavity, the mating anti-rotation protrusions preventing relative rotation between the mask, cassette, and cup. In certain embodiments, the anti-rotation protrusions define a pair of upwardly open removal slots configured for grasping with a tweezers to remove the mask from the cup.

In certain embodiments of the device, the cassette includes a peripheral frame having a generally circular configuration dimensioned to fit in the cavity of the cup. In certain embodiments, the peripheral frame includes a removal slot configured for lifting the cassette into and out of the cup.

In certain embodiments of the device, the cup comprises a bottom wall, a cylindrical exterior sidewall extending upwards from the bottom wall, and an interior fluid retention wall extending upwards from the bottom wall and surrounding the tissue scaffold 303. In certain embodiments, the fluid retention wall has a continuous structure for retaining fluid. In certain embodiments, the fluid retention wall is spaced radially inwards from the sidewall and defines an annular mounting recess formed between the sidewall of the cup and retention wall which receives a peripheral frame, also referred to as a cassette frame 320, of the cassette at least partially therein. In certain embodiments, the device further comprises a recessed seeding trough formed in the bottom wall and arranged directly beneath the tissue scaffold within the fluid retention wall. In certain embodiments, the seeding trough has a first floor defining a lower fluid volume than a second floor surrounding the seeding trough inside the fluid retention wall, the second floor located at a higher elevation than the first floor.

In certain embodiments, of the device, when the seeding trough is filled with a fluid media, the tissue scaffold contacts at least a surface of the fluid media. In certain embodiments, the lid comprises a peel-able foil film adhesively adhered to the top of the cup to hermetically seal and enclose the cavity. In certain embodiments, the top of the cup comprises an outwardly turned lip to which the foil film is adhered.

In certain embodiments of the device, the fluid is buffered saline solution. In certain embodiments, the cup includes a pair of upstanding locking protrusions insertable into an opening in the cassette on each side of the tissue scaffold to prevent rotation between the cup and cassette.

In other embodiments, a biomechanical testing system for tissue analysis is provided comprising: a cassette containing a tissue scaffold supporting a tissue specimen; and an instrument comprising: an upper housing defining an upper cavity; a lower housing movably coupled to the upper housing and defining a lower cavity, the upper housing movable between an open position and a closed position engaged with the lower housing; the lower housing comprising a testing bath block including a receptacle configured for holding a fluid and removably receiving the cassette therein for analysis; a pin drive mechanism comprising a pair of spreader pins operably engageable with the cassette when positioned in the receptacle, and a programmable microcontroller operably linked to the pin drive mechanism, the microcontroller configured to move the pins together and apart in opposing directions.

In certain embodiments of the system, the pin drive mechanism is mounted in the upper housing and the pins protrude downwards therefrom. In further embodiments, the pins project at least partially into the receptacle to engage the cassette when the upper housing is moved to the closed position. In certain embodiments, the pins are operable to engage and spread a pair of resiliently flexible cantilevered spring arms of the cassette in the receptacle which support the tissue scaffold. In certain embodiments, the spring arms are moveable via operation of the pin drive mechanism between a collapsed position which locks the tissue scaffold to the cassette, and an expanded position which unlocks the tissue scaffold from the cassette. In certain embodiments, the system further comprises a heater which heats the bath block. In certain embodiments, the heater is controlled by the microcontroller, the microcontroller operable to cause the heater to heat the bath block to maintain a preprogrammed minimum temperature setpoint of the fluid when contained in the bath block receptacle. In certain embodiments, the bath block is metal and the heater is an electrical resistance heater element. In certain embodiments, the system further comprises a temperature sensor operably linked to the microcontroller, the microcontroller configured to determine a temperature indicative of a temperature of the fluid in the bath block and regulate the temperature of the fluid. In certain embodiments, the system further comprises a fluid level control system comprising a pump fluidly coupled to the bath block, the fluid level control system configured to circulate the fluid through the receptacle in a closed flow loop. In certain embodiments, the lower housing further comprises a pair of fluid exchanged ports fluidly coupled to the closed flow loop and receptacle for circulating the fluid. In certain embodiments, the fluid level control system further comprises a level sensor operable to measure a surface level of the fluid in the receptacle. In certain embodiments, the level sensor and pump are operably linked to the microcontroller, the microcontroller configured to control the pump to regulate the surface level of fluid in the receptacle to maintain a preprogrammed level setpoint. In certain embodiments, the level sensor is a filtered infrared reflectance sensor positioned above the surface level of fluid in the receptacle. In certain embodiments, the pump is a syringe pump. In certain embodiments, the system further comprises a waste pump for removing fluid from the closed flow loop, and an injection port for adding fluid to the closed flow loop.

In further embodiments, the system further comprises a force transducer cantilever mounted to the upper housing and operably linked to the microcontroller, the force transducer cantilever insertable into the cassette and operable to measure a tensile force of the tissue specimen when stretched. In certain embodiments, the force transducer cantilever is linearly movable and configured to stretch the tissue specimen for obtaining the tensile force measurement. In certain embodiments, the tissue scaffold is attached to a floating clip detachably coupled to the cassette, and the force transducer cantilever is configured to engage and linearly translate the floating clip to stretch the tissue specimen. In certain embodiments, the floating clip is supported between a pair of resiliently flexible cantilevered spring arms disposed on the cassette, and moving the spreader pins apart displaces the spring arms to uncouple and release the floating clip from the cassette such that the force transducer cantilever can linearly translate the floating clip.

In certain embodiments of the biomechanical testing system, the spring arms are movable between an inward collapsed configuration which retains the floating clip to the cassette and an outward spread apart configuration which releases the floating clip. In certain embodiments, the force transducer cantilever comprises a movable carriage frame defining a pair of spaced apart and downwardly extending legs configured and arranged to engage the floating clip on each side of the tissue scaffold. In certain embodiments, the force transducer cantilever comprises a drive mechanism operably coupled to the frame to translate the frame in opposing linear directions.

In certain embodiments, the system further comprises a laser directed to a reflective surface of the force transducer cantilever which reflects the laser onto a bi-cell photosensor, the photosensor operable to measure movement of the floating clip.

In certain embodiments, the system further comprises an electrode mounted to the upper housing and operably linked to the microcontroller, the electrode operable to electrically stimulate the tissue specimen to elicit contraction thereof.

In certain embodiments, the upper and lower housings are hingedly coupled together by a chain linkage opening mechanism operable to keep each housing parallel to each other when the upper moves between the closed and open positions. In certain embodiments, the spreader pins remain in a vertical position when the upper housing moves between the open and closed positions.

In certain embodiments, the system further comprises a pair of elongated hinge links each having a lower end pivotably coupled to the lower housing and an upper end pivotably coupled to the upper housing. In certain embodiments, the hinge links elevate the upper housing above the lower housing when in the open position such that the upper housing does not contact the lower housing. In certain embodiments, the upper housing translates horizontally relative the lower housing when moved from the closed position to the open position. In certain embodiments, the chain linkage opening mechanism further includes an elongated gear bar having a lower end pivotably coupled to the lower housing and an enlarged end comprising a gear rack operably meshed with a gear on a housing drive motor mounted to the upper housing. In certain embodiments, the gear rack is arcuately curved. In certain embodiments, the microcontroller is operably coupled to the housing drive motor, the microcontroller configured to control the housing drive motor to selectively move the upper housing between the open and closed positions.

In certain embodiments of the system, the instrument further includes an electrical power supply connection, a computer interface connection, and a pump control connection all operably coupled to the microcontroller.

In certain embodiments, the system further comprises a transparent window arranged on the lower housing which provides a view of bath block receptacle and tissue scaffold.

In other embodiments, the invention is a biomechanical testing system 2000 for tissue analysis comprising: a cassette 300 comprising: a peripheral frame 320; a tissue scaffold 303 supporting a tissue specimen, the tissue scaffold 303 being attached to a floating clip 310 detachably coupled to the peripheral frame 320; the floating clip 310 being supported between a pair of resiliently flexible cantilevered spring arms 323 and 325 disposed on the cassette 300, the spring arms 323 and 325 movable between an inward collapsed configuration which retains the floating clip 310 to the cassette 300 and an outward spread apart configuration which releases the floating clip 10; an instrument comprising: an upper housing 500 defining an upper cavity; a lower housing 502 movably coupled to the upper housing 500 and defining a lower cavity, the upper housing 500 movable between an open position and a closed position engaged with the lower housing 502; the lower housing 502 comprising a testing bath block 503 including a cassette receptacle 506 configured for holding a sterile fluid and removably receiving the cassette therein for analysis; a pin drive mechanism comprising a pair of spreader pins 631 operably engageable with the spring arms 323 and 325 of the cassette 300 when positioned in the receptacle 506, and a programmable microcontroller operably linked to the pin drive mechanism, the microcontroller configured to move the pins between the inward collapsed and outward spread apart configurations for releasing the floating clip 310. In certain embodiments, the biomechanical testing system further comprises a force transducer cantilever 620 mounted to the upper housing 500 and operably linked to the microcontroller, the force transducer cantilever 620 insertable into the cassette 300 and operable to engage and linearly translate the floating clip 310 to stretch the tissue specimen when the floating clip 310 is detached from the peripheral frame 320 of the cassette 300. In certain embodiments, the force transducer cantilever is configured to measure a tensile force created in the tissue specimen when stretched and transmit the measured tensile force to the microcontroller. In certain embodiments, the biomechanical testing system further comprises an electrode mounted to the upper housing and operably linked to the microcontroller, the electrode operable to electrically stimulate the tissue specimen to elicit contraction thereof which is measured by the microcontroller. In further embodiments, the biomechanical testing system further comprises a fluid level control system comprising a pump fluidly coupled to the bath block, the fluid level control system configured to circulate the fluid through the receptacle in a closed flow loop, and a level sensor operable to measure a surface level of the fluid in the receptacle. In certain embodiments, the level sensor and pump are operably linked to the microcontroller, the microcontroller configured to cause the pump to regulate the surface level of fluid in the receptacle to maintain a preprogrammed level setpoint. In certain embodiments, the upper housing is moved to the closed position, the microcontroller is configured to automatically initiate the pin drive mechanism and the force transducer cantilever to stretch the tissue specimen and measure the tensile force in the tissue specimen. In certain embodiments, the microcontroller is further configured to activate an electrode operable to electrically stimulate the tissue specimen to elicit contraction thereof which is measured by the microcontroller.

In certain embodiments, the invention is a method for preparing an engineered tissue specimen, the method comprising: providing a packaged bioreactor including a seeding cup containing a cassette supporting a tissue scaffold immersed in a sterile fluid, the tissue scaffold supported inside the cup beneath an internal mask, and a lid sealing the cup; removing the sealed lid; inserting a first pipette through an aspiration hole in the mask to access the fluid; aspirating the cup to draw at least a portion of the fluid out; inserting a first pipette through a seeding hole in the mask to access the tissue scaffold; and seeding the tissue scaffold with tissue cells. In certain embodiments, the seeding hole is located in the mask over the tissue scaffold and the aspiration hole is laterally offset from the seeding hole. In certain embodiments, the method further comprises a step of placing the seeding cup in a cell of a standard twelve cell laboratory culture tray. In certain embodiments, the method further comprises the steps of: removing the cassette from the culture tray; removing the mask from seeding cup to access the cassette; and transferring the cassette with tissue specimen to a testing instrument. In certain embodiments, the method further comprises placing the cassette in a fluid bath of the instrument having a temperature controlled closed flow loop. In certain embodiments, the removing step includes peeling a foil seal adhered to a top of the seeding cup to access an internal cavity of the cup.

In certain embodiments, the invention is a method for automatically testing a tissue specimen, the method comprising providing a cassette containing a tissue specimen supported by a tissue scaffold having a floating clip detachably coupled to a frame of the cassette; opening a testing instrument comprising a microcontroller; inserting the cassette in a receptacle of the instrument containing a sterile fluid; closing the instrument; the microcontroller activating a decoupling mechanism which uncouples the floating clip from the cassette; the microcontroller activating a movable force transducer cantilever which engages and translates the floating clip; stretching the tissue specimen by the force transducer cantilever translating the floating clip in a first direction; and measuring a tensile force in the tissue specimen with the force transducer cantilever which transmits the tensile force measurement to the microcontroller. In certain embodiments, the step of the microcontroller activating the decoupling mechanism comprises moving a pair of spreader pins of the instrument apart which expands a pair of spring arms of the cassette to detachably couple the floating clip to the frame of the cassette. In certain embodiments, the method further comprises the microcontroller activating an electrode which electrically stimulates the tissue specimen to elicit a contraction, and measuring a degree of the contraction via the microcontroller. In certain embodiments, the method further comprises: circulating the fluid through the receptacle; measuring a temperature of the fluid via a temperature sensor operably linked to the microcontroller; and the microcontroller regulating the temperature of the fluid via a heater to maintain a preprogrammed setpoint temperature. In certain embodiments, the method further comprises a level sensor operably coupled to the microcontroller, the microcontroller controlling a level of the fluid in the receptacle (bath) via regulating a pumping system which circulates the fluid through the receptacle.

In certain embodiments, the method for automatically testing a tissue further comprises: bending the force transducer cantilever about its point of rotation via stretching the tissue specimen; shining a laser beam on a reflective surface of the force transducer cantilever; reflecting the laser beam onto a light detector operably linked to the microcontroller; the microcontroller comparing a shift of a spot produced by the reflected laser beam on the light detector against a preprogrammed baseline spot with the force transducer cantilever in an unbent condition; and the microcontroller correlating the shift of the reflected laser beam to a tensile force in the tissue specimen. In certain embodiments, the light detector is a bi-cell photodiode.

In certain embodiments, the method for automatically testing a tissue specimen further comprises: moving the force transducer cantilever in a second direction opposite to the first direction to return the floating clip to an initial starting position before the tissue specimen is stretched; moving the pair of spreader pins together which return the pair of spring arms to an original collapsed position; and recoupling the floating clip to the frame of the cassette. In certain embodiments, the method further comprises removing the cassette with tissue specimen from the instrument and storing the cassette in a cell of a tissue culture tray.

In overview, the biomedical tissue generation and testing system may generally comprise a bioreactor device 1000 including a cassette 300 comprising a specially designed tissue cassette frame 320, and a tissue testing instrument 2000, which is configured to interface with the cassette frame. Advantageously, the system eliminates the process of manual tissue mounting and the more advanced skills typically required for successfully handling tissue specimens. A scaffold 303 may be mounted within the cassette 300 between two anchoring locking slots 313 and 327, which may be also referred to as insert slots (see, for example, FIGS. 3A and 19A-C). One of these anchor points is disposed on a free-floating detachable clip 310 mounted to the cassette frame 320. Two spring arms, first flexible spring arm 323 and second flexible spring arm 325, within the cassette 300 engage with the ends of the clip (the first detachable clip arm 311 and second detachable clip arm 312) thereby holding the scaffold 303 stationary during cellular seeding, culture, and transport of the scaffold 303. The other tissue scaffold anchor point is formed by a fixed clip 315, which in one non-limiting embodiment may be integrally formed as a unitary structural part of the cassette frame 320.

The cassette 300 may be placed into a tissue culture dish, such as a standard 12 well cell culture dish 700, for incubation of tissue specimen, such as the seeded cells deposited, onto the scaffold 303. Incubation allows the tissue specimen to attach to the scaffold 303. At the time of biomechanical testing, the cassette/tissue assembly containing the tissue specimen can be removed from the tissue culture dish and placed into the testing bath block 503 (See, for example, FIG. 6A) in a manner that requires very little dexterity or practice. Once the specimen is in place, the user may initiate sample measurement by use of the graphical user interface, such as a software application on a computer 2002. The system may automatically (via motorized actuators) close the upper housing 500 of the machine, which brings elements of the upper housing 500 into precise position with regard to the tissue cassette 300 (See, for example FIGS. 7 and 8). Such elements include the force transducer cantilever 620 and spreader pins 631. Motorized actuators then translate the transducer cantilever 620 laterally until the horizontal prongs 621 thereof are fully under the floating clip 310 and the vertical face of the clip is securely engaged with the transducer cantilever 620 (See, for example, FIG. 9). Once the clip 310 and force transducer cantilever 620 are successfully engaged, the clip 310 is disengaged from the cassette 300 by the motorized actuation of the spreader pins 631 (See, for example, FIGS. 10, 30A and 30B). The spreader pins 631 may move laterally, engaging with the cassette's spring arms (323 & 325) and bending them outwards such that the clip is released. At this point, the tissue is ready for mechanical testing, since the clip 310 is free of the cassette 300 and any forces originating from the tissue are transmitted through the clip 310 without loss to the force-sensing cantilever 620.

While the present invention has been described with respect to specific examples, or embodiments, including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present invention.

What is claimed is:

1. A packaged bioreactor device comprising:
 a cup including a bottom, a top, and an internal cavity extending between the bottom and the top;
 a lid sealing the top of the cup and being removable to access the cavity;
 a tissue scaffold supported in the cavity; and
 a mask removably disposed in the cavity above the tissue scaffold, the mask including a plurality of through holes to access the tissue scaffold and a portion of the cavity below the mask;
 wherein the tissue scaffold is supported by a cassette removably disposed in the cavity of the cup below the mask; and
 wherein the cassette includes a fixed clip engaging a first end of the tissue scaffold, and a second floating clip engaging a second end of the tissue scaffold, the floating clip detachably coupled to the cassette.

2. The device according to claim 1, wherein floating clip is supported between a pair of resiliently flexible cantilevered spring arms, the spring arms spreadable to disengage and release the floating clip.

3. The device according to claim 2, wherein the spring arms are movable between an inward collapsed configuration which retains the floating clip to the cassette and an outward spread apart configuration which releases the floating clip.

4. The device according to claim 1, wherein the first and second ends of the tissue scaffold are each fixedly coupled to the fixed and floating clips by a locking peg arranged in a light bulb shaped locking slot formed in the clips.

5. The device according to claim 4, wherein the locking slots include a narrow throat portion and a diametrically enlarged circular seating portion in which the locking pegs are positioned when the tissue scaffold is locked to the clips, wherein the locking pegs are comprised of hydrogel and changeable from a shrunken diameter when the pegs are in a dehydrated condition to a larger enlarged diameter when the pegs are hydrated, and wherein the locking pegs can pass through the throat portion when in the dehydrated condition with the shrunken diameter, but cannot pass through the throat portion when in the hydrated condition with the enlarged diameter.

6. The device according to claim 1, wherein the cassette is configured to hold the tissue scaffold in an inverted suspended manner stretched between each clip in which the tissue scaffold is located below the clips.

7. The device according to claim 1, wherein the cassette includes a peripheral frame having a generally circular configuration dimensioned to fit in the cavity of the cup, and wherein the peripheral frame includes a removal slot configured for lifting the cassette into and out of the cup.

8. The device according to claim 1, wherein the cup comprises a bottom wall, a cylindrical exterior sidewall extending upwards from the bottom wall, and an interior fluid retention wall extending upwards from the bottom wall and surrounding the tissue scaffold.

9. The device according to claim 8, wherein the fluid retention wall is spaced radially inwards from the sidewall and defines an annular mounting recess formed between the sidewall of the cup and retention wall which receives a peripheral frame of the cassette at least partially therein.

10. The device according to 8, further comprising a recessed seeding trough formed in the bottom wall and arranged directly beneath the tissue scaffold within the fluid retention wall.

11. The device according to claim 10, wherein the seeding trough has a first floor defining a lower fluid volume than a second floor surrounding the seeding trough inside the fluid retention wall, the second floor located at a higher elevation than the first floor.

12. The device according to claim 11, wherein when the seeding trough is filled with a fluid media, the tissue scaffold contacts at least a surface of the fluid media.

13. The device according to claim 1, wherein the cup includes a pair of upstanding locking protrusions insertable into an opening in the cassette on each side of the tissue scaffold to prevent rotation between the cup and cassette.

14. A packaged bioreactor device comprising:
 a cup including a bottom, a top, and an internal cavity extending between the bottom and the top;
 a lid sealing the top of the cup and being removable to access the cavity;
 a tissue scaffold supported in the cavity; and
 a mask removably disposed in the cavity above the tissue scaffold, the mask including a plurality of through holes to access the tissue scaffold and a portion of the cavity below the mask;
 wherein the tissue scaffold is supported by a cassette removably disposed in the cavity of the cup below the mask;
 wherein the cassette includes a fixed clip engaging a first end of the tissue scaffold, and a second floating clip engaging a second end of the tissue scaffold, the floating clip detachably coupled to the cassette;
 wherein the mask includes a pair of downwardly extending first anti-rotation protrusions arranged to engage a mating pair of upwardly extending second anti-rotation protrusions formed on a bottom wall of the cup within the cavity, the mating anti-rotation protrusions preventing relative rotation between the mask, cassette, and cup.

15. The device according to claim 14, wherein the anti-rotation protrusions define a pair of upwardly open removal slots configured for grasping with a tweezers to remove the mask from the cup.

\* \* \* \* \*